United States Patent
Taugerbeck et al.

(10) Patent No.: US 9,096,795 B2
(45) Date of Patent: Aug. 4, 2015

(54) LIQUID CRYSTAL DISPLAY

(75) Inventors: Andreas Taugerbeck, Darmstadt (DE); Alexander Hahn, Biebesheim (DE); Achim Goetz, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 800 days.

(21) Appl. No.: 13/321,962

(22) PCT Filed: Apr. 19, 2010

(86) PCT No.: PCT/EP2010/002374
§ 371 (c)(1),
(2), (4) Date: Nov. 22, 2011

(87) PCT Pub. No.: WO2010/133278
PCT Pub. Date: Nov. 25, 2010

(65) Prior Publication Data
US 2012/0069289 A1 Mar. 22, 2012

(30) Foreign Application Priority Data

May 22, 2009 (DE) .......................... 10 2009 022 309

(51) Int. Cl.
| | | |
|---|---|---|
| C09K 19/32 | (2006.01) | |
| C09K 19/30 | (2006.01) | |
| C07C 25/22 | (2006.01) | |
| C07D 307/91 | (2006.01) | |
| C07D 311/80 | (2006.01) | |
| C09K 19/34 | (2006.01) | |
| C09K 19/04 | (2006.01) | |
| C09K 19/54 | (2006.01) | |
| G02F 1/1333 | (2006.01) | |
| G02F 1/137 | (2006.01) | |

(52) U.S. Cl.
CPC ................. *C09K 19/32* (2013.01); *C07C 25/22* (2013.01); *C07D 307/91* (2013.01); *C07D 311/80* (2013.01); *C09K 19/3402* (2013.01); *C09K 19/3477* (2013.01); *C09K 19/3491* (2013.01); *C07C 2103/18* (2013.01); *C07C 2103/26* (2013.01); *C09K 2019/0448* (2013.01); *C09K 2019/3422* (2013.01); *C09K 2019/3425* (2013.01); *C09K 2019/548* (2013.01); *G02F 2001/13775* (2013.01); *G02F 2001/133397* (2013.01)

(58) Field of Classification Search
CPC .... C07D 30/91; C07D 311/807; C07C 25/22; C07C 2103/18; C07C 2103/26; C09K 19/32; C09K 19/3402; C09K 19/3477; C09K 19/3491; C09K 2019/0448; C09K 2019/3422; C09K 2019/3425; C09K 2019/548; G02F 2001/13775; G02F 2001/133397

USPC ............ 252/299.61, 299.62, 299.63; 428/1.1; 349/183; 560/76, 80
See application file for complete search history.

(56) References Cited

U.S. PATENT DOCUMENTS

| | | | |
|---|---|---|---|
| 5,648,021 A | 7/1997 | Wingen et al. | |
| 5,674,576 A | 10/1997 | Gotoh et al. | |
| 6,824,709 B2 | 11/2004 | Shundo | |
| 8,246,855 B2 * | 8/2012 | Hirai | ........................ 252/299.66 |
| 8,394,468 B2 | 3/2013 | Ito et al. | |
| 8,883,230 B2 | 11/2014 | Wu | |
| 2002/0110650 A1 | 8/2002 | Sekine et al. | |
| 2003/0203128 A1 | 10/2003 | Shundo | |
| 2005/0255258 A1 | 11/2005 | Schmidt et al. | |
| 2007/0257230 A1 | 11/2007 | Cherkaoui et al. | |
| 2008/0146853 A1 | 6/2008 | Midorikawa et al. | |
| 2009/0137761 A1 | 5/2009 | Irisawa et al. | |
| 2009/0214681 A1 | 8/2009 | Wu | |
| 2012/0092608 A1 | 4/2012 | Ito et al. | |

FOREIGN PATENT DOCUMENTS

| | | | |
|---|---|---|---|
| DE | 10 2006 057 250 A1 | 8/2007 | |
| DE | 10 2008 036 248 A1 | 3/2009 | |
| EP | 0 397 418 A1 | 11/1990 | |
| EP | 1 837 324 A1 | 9/2007 | |
| EP | 1 944 287 A1 | 7/2008 | |
| JP | 63-233952 A | 9/1988 | |
| JP | 2003-238491 A | 8/2003 | |
| JP | 2009-114247 A | 5/2009 | |
| JP | 2011-513316 A | 4/2011 | |
| WO | WO 2005/054406 A1 | 6/2005 | |
| WO | WO 2009/030322 A1 | 3/2009 | |
| WO | WO 2009/030352 A1 | 3/2009 | |
| WO | 2010/131600 A1 | 11/2010 | |

OTHER PUBLICATIONS

International Search Report of PCT/EP2010/002374 (Jun. 10, 2010).
J.W. Cornforth et al., "Experiments on the Synthesis of Substances Related to the Sterols. The Preparation of 2:7-Dihydroxyphenanthrene and Certain Derivatives. Further Observations on the Reduction of 1-gamma-Ketobutyl-2-Naphthol", Journal of the Chemical Society (Jun. 27, 1942) XP008122950 pp. 684-689.
D.E. Pearson et al., "Phosphoric Acid Systems, Part 7. The Halogenation or Nitration of Aryl Compounds in Trialkyl Phosphates", Synthesis (Sep. 1, 1976) XP008122907 pp. 621-623.
Japanese Examination Procedure dated Nov. 25, 2014 issued in corresponding application JP 2013-265131 (pp. 1-4).
English Translation Abstract of JP 2009-114247 published May 28, 2009.

* cited by examiner

*Primary Examiner* — Geraldina Visconti
(74) *Attorney, Agent, or Firm* — Millen, White, Zelano & Branigan, P.C.

(57) ABSTRACT

The present invention relates to polymerisable compounds, to processes and intermediates for the preparation thereof, and to the use thereof for optical, electro-optical and electronic purposes, in particular in liquid-crystal (LC) media and LC displays, especially in LC displays of the PS (polymer stabilised) and PSA (polymer sustained alignment) type.

17 Claims, No Drawings

LIQUID CRYSTAL DISPLAY

The present invention relates to polymerisable compounds, to processes and intermediates for the preparation thereof, and to the use thereof for optical, electro-optical and electronic purposes, in particular in liquid-crystal (LC) media and LC displays, especially in LC displays of the PS (polymer-stabilised) or PSA (polymer-sustained alignment) type.

The liquid-crystal displays (LC displays) used at present are usually those of the TN ("twisted nematic") type. However, these have the disadvantage of a strong viewing-angle dependence of the contrast. In addition, so-called VA ("vertical alignment") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the electrodes, a realignment of the LC molecules parallel to the electrode surfaces takes place. Furthermore, OCB (optically compensated bend) displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays. Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane. Furthermore, so-called FFS ("fringe-field switching") displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of an electrode which is structured in a comb-shaped manner, and the other electrode is unstructured. A strong, so-called "fringe field" is thereby generated, i.e. a strong electric field close to the edge of the electrodes, and, throughout the cell, an electric field which has both a strong vertical component and also a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes. In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slotted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In the so-called PVA (patterned VA), protrusions are rendered completely superfluous in that both electrodes are structured by means of slits on the opposite sides, which results in increased contrast and improved transparency to light, but is technologically difficult and makes the display more sensitive to mechanical influences (tapping, etc.). For many applications, such as, for example, monitors and especially TV screens, however, a shortening of the response times and an improvement in the contrast and luminance (transmission) of the display are demanded.

A further development are the so-called PS or PSA (polymer sustained [alignment]) displays, which are also known under the term "polymer stabilised". In these, a small amount (for example 0.3% by weight, typically <1% by weight) of a polymerisable compound is added to the LC medium and, after introduction into the LC cell, is polymerised or cross-linked in situ, usually by UV photopolymerisation, with or without an electrical voltage applied between the electrodes. The addition of polymerisable mesogenic or liquid-crystalline compounds, also known as reactive mesogens or "RMs", to the LC mixture has proven particularly suitable.

In the meantime, the PSA principle is being used in diverse classical LC displays. Thus, for example, PSA-VA, PSA-OCB, PS-IPS/FFS and PS-TN displays are known. The polymerisation of the polymerisable compound(s) preferably takes place with an applied electrical voltage in the case of PSA-VA and PSA-OCB displays, and with or without, preferably without, an applied electrical voltage in the case of PSA-IPS displays. As can be demonstrated in test cells, the PSA method results in a pretilt in the cell. In the case of PSA-OCB displays, it is therefore possible for the bend structure to be stabilised so that an offset voltage is unnecessary or can be reduced. In the case of PSA-VA displays, this pretilt has a positive effect on response times. For PSA-VA displays, a standard MVA or PVA pixel and electrode layout can be used. In addition, however, it is possible, for example, to manage with only one structured electrode side and no protrusions, which significantly simplifies production and at the same time results in very good contrast at the same time as very good transparency to light.

PSA-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs"), while in the case of passive-matrix displays, individual pixels are usually addressed by the multiplex method, as known from the prior art.

In particular for monitor and especially TV applications, optimisation of the response times, but also of the contrast and luminance (thus also transmission) of the LC display continues to be demanded. The PSA method can provide crucial advantages here. In particular in the case of PSA-VA, a shortening of the response times, which correlate with a measurable pretilt in test cells, can be achieved without significant adverse effects on other parameters.

In the prior art, use is made, for example, of polymerisable compounds of the formula 1

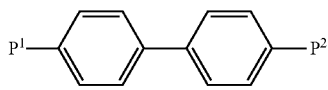

in which P denotes a polymerisable group, usually an acrylate or methacrylate group, as described, for example, in U.S. Pat. No. 7,169,449.

However, the problem arises that not all combinations consisting of LC mixture (also referred to as "LC host mixture" below)+polymerisable component (typically RMs) are suitable for PSA displays since, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerisation by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce particularly small pretilt angles. Preferred materials here are those which produce a lower pretilt angle during polymerisation for the same exposure time than materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerised RMs, in particular after the polymerisation step for production of the pretilt angle in the display. For example, unreacted RMs of this type may adversely affect the properties of the display by, for example, polymerising in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they reduce the effective applied voltage. This effect can also be observed in conventional LC displays without a polymer component.

In addition, an additional "image sticking" effect caused by the presence of unpolymerised RMs is often observed in PSA displays. Uncontrolled polymerisation of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerisation of the RMs to proceed as completely as possible during production of the PSA display and for the presence of unpolymerised RMs in the display to be excluded as far as possible or reduced to a minimum. To this end, materials are required which enable highly effective and complete polymerisation. In addition, controlled reaction of these residual amounts would be desirable. This would be simpler if the RM polymerises more quickly and effectively than the materials known to date.

There is thus still a great demand for PSA displays, in particular of the VA and OCB type, and LC media and polymerisable compounds for use in such displays, which do not exhibit the disadvantages described above or only do so to a small extent and have improved properties. In particular, there is a great demand for PSA displays, and materials for use in PSA displays, which enable a high specific resistance at the same time as a large working-temperature range, short response times, even at low temperatures, and a low threshold voltage, a low pretilt angle, a multiplicity of grey shades, high contrast and a broad viewing angle, and have high values for the "voltage holding ratio" (VHR) after UV exposure.

The invention is based on the object of providing novel suitable materials, in particular RMs and LC media comprising same, for use in PSA displays, which do not have the disadvantages indicated above or do so to a reduced extent, polymerise as rapidly and completely as possible, enable a low pretilt angle to be established as quickly as possible, reduce or prevent the occurrence of "image sticking" in the display, and preferably at the same time enable very high specific resistance values, low threshold voltages and short response times.

A further object of the invention is the provision of novel RMs, in particular for optical, electro-optical and electronic applications, and of suitable processes and intermediates for the preparation thereof.

In particular, the invention is based on the object of providing polymerisable compounds which produce a greater maximum pretilt after photopolymerisation, which results in the desired pretilt being achieved more quickly and thus in significantly shortened times for production of the LC display.

This object has been achieved in accordance with the invention by the provision of materials, processes and displays as described in the present application. In particular, it has been found, surprisingly, that some or all of the objects described above can be achieved by using PSA displays according to the invention which contain a polymerised compound containing a structural element of the formula 2

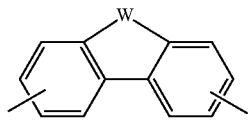

2 in which W denotes a carbyl bridge or a heteroatom. Compared with the compounds of the formula 1 given above which are known from the prior art, the introduction of a bridging element into the biaryl skeleton restricts the mobility around the central bond and thus gives a rigid and more sterically hindered skeleton.

The use of polymerisable compounds of this type in LC media and PSA displays according to the invention results in the desired pretilt being achieved particularly quickly and in significantly shortened times for production of the display. This has been demonstrated in connection with an LC medium by means of exposure time-dependent pretilt measurements in VA tilt measurement cells. In particular, it was possible to achieve a pretilt without the addition of photoinitiator.

Since the polymerisable compounds in the displays according to the invention exhibit a significantly higher polymerisation rate, fewer unreacted residual amounts also remain in the cell, causing an improvement in the electro-optical properties thereof, and the controlled reaction of these residual amounts becomes simpler.

Polymerisable compounds containing a structural element of the formula 2 have already been described for other purposes in the prior art. Thus, U.S. Pat. No. 6,824,709 discloses polymerisable compounds containing a central fluorene group (i.e. of the formula 2 in which W=$CH_2$) for use in anisotropic polymer films, such as, for example, alignment layers, retardation films or polarisers.

U.S. Pat. No. 5,674,576 discloses LC displays of the PSCT ("polymer stabilised cholesteric texture") type or PDLC ("polymer dispersed liquid crystal") type, containing a chiral nematic or cholesteric LC medium (i.e. having a helical twist of the LC molecules) and a polymer. The polymer is obtainable by polymerisation of a fluorene diacrylate or dimethacrylate, or a derivative thereof containing an O or NH bridge instead of the $CH_2$ bridge. By application of a voltage, the display is switched between various states in which the chiral LC medium either exhibits light scattering, transparency or selective reflection of coloured light. However, U.S. Pat. No. 5,674,576 does not disclose any displays of the PSA type as described in the present invention in which the polymerisation of the polymerisable component takes place with application of a voltage and a pretilt angle is thus produced in the LC medium. In addition, the LC displays described in U.S. Pat. No. 5,674,576 contain relatively large amounts of polymerisable compounds, preferably 0.5 to 8% by weight, in order to facilitate visible scattering effects or reflection. By contrast, such large amounts of RMs and the scattering effects or selective reflection caused thereby are undesired in the PSA displays of the present invention. The long polymerisation times of 150-180 minutes described in the examples of U.S. Pat. No. 5,674,576 are also unsuitable for production of LC displays on an industrial scale.

However, the use of polymerisable fluorene derivatives in low-molecular-weight LC media for PSA displays for rapid establishment of a tilt angle through in-situ polymerisation in an electric field has to date neither been described nor proposed in the prior art.

The invention thus relates to the use of compounds of the formula I

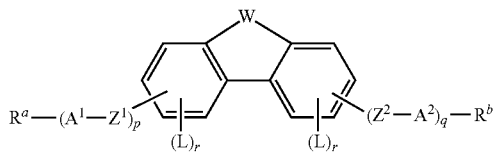

I in which the individual radicals have the following meanings:
W denotes —$C(R^cR^d)$—, —$CH_2CH_2$—, —$CH_2$—O—, —O—, —CO—, —CO—O—, —S— or —$N(R^c)$—,
$R^c$, $R^d$ each, independently of one another, denote P-Sp-, H, F, Cl, Br, I, —CN, —$NO_2$, —NCO, —NCS, —OCN, —SCN, $SF_5$, straight-chain or branched alkyl having 1 to 25 C atoms, in which, in addition, one or more non-adjacent $CH_2$ groups may each be replaced, independently of one another, by arylene, —$C(R^0)$=$C(R^{00}$—, —C≡C—, —$N(R^0)$—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, or aryl or heteroaryl, preferably having 2 to 25 C atoms, which may also contain two or more fused rings and which is optionally mono- or polysubstituted by L,
$R^a$, $R^b$ each, independently of one another, have one of the meanings indicated for $R^c$, where at least one of the radicals $R^a$ and $R^b$ denotes or contains a group P-Sp-,
P on each occurrence, identically or differently, denotes a polymerisable group,
Sp on each occurrence, identically or differently, denotes a spacer group or a single bond,
$A^1$, $A^2$ each, independently of one another, denote an aromatic, heteroaromatic, alicyclic or heterocyclic group, preferably having 4 to 25 C atoms, which may also contain fused rings and which is optionally mono- or polysubstituted by L,
L on each occurrence, identically or differently, denotes P-Sp-, H, OH, $CH_2OH$, halogen, $SF_5$, $NO_2$, a carbon group or hydrocarbon group,
$Z^1$, $Z^2$ each, independently of one another, denote —O—, —S—, —CO—, —CO—O—, —OCO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CH_2)_n$—, —$CF_2CH_2$—, —$CH_2CF_2$—, —$(CF_2)_n$—, —CH=CH—, —CF=CF—, —CH=CF—, —CF=CH—, —C≡C—, —CH=CH—COO—, —OCO—CH=CH—, —$CH_2$—$CH_2$—COO—, —OCO—$CH_2$—$CH_2$—, —$C(R^0R^{00})$—, —$C(R^yR^z)$— or a single bond,
$R^0$, $R^{00}$ each, independently of one another and identically or differently on each occurrence, denote H or alkyl having 1 to 12 C atoms,
$R^y$, $R^z$ each, independently of one another, denote H, F, $CH_3$ or $CF_3$, n on each occurrence, identically or differently, denotes 1, 2, 3 or 4, p, q each, independently of one another, denote 0, 1, 2 or 3, r on each occurrence, identically or differently, denotes 0, 1, 2 or 3, in liquid-crystal (LC) media and LC displays of the PS (polymer stabilised) or PSA (polymer sustained alignment) type.

The invention furthermore relates to an LC medium comprising one or more polymerisable compounds of the formula I and one or more additional compounds, which may also be mesogenic, liquid-crystalline and/or polymerisable.

The invention furthermore relates to an LC medium comprising a polymer obtainable by polymerisation of one or more compounds of the formula I and one or more additional compounds, which may also be mesogenic, liquid-crystalline and/or polymerisable.

The invention furthermore relates to an LC medium comprising
- a polymerisable component A) comprising one or more polymerisable compounds of the formula I, and
- a liquid-crystalline component B), also referred to below as "LC host mixture", comprising one or more, preferably two or more, low-molecular-weight (monomeric and unpolymerisable) compounds as described above and below.

The invention furthermore relates to a process for the preparation of an LC medium as described above and below in which one or more low-molecular-weight liquid-crystalline compounds, or an LC host mixture as described above and below, are mixed with one or more polymerisable compounds of the formula I or sub-formulae thereof, and optionally with further liquid-crystalline compounds and/or additives.

The invention furthermore relates to the use of compounds of the formula I and LC media according to the invention in PS and PSA displays, in particular the use in PS and PSA displays containing an LC medium, for the production of a tilt angle in the LC medium through in-situ polymerisation of the compound(s) of the formula I in the PSA display with application of an electric or magnetic field.

The invention furthermore relates to an LC display containing one or more compounds of the formula I or an LC medium according to the invention, in particular a PS or PSA display, particularly preferably a PSA-VA, PSA-OCB, PS-IPS, PS-FFS or PS-TN display.

The invention furthermore relates to an LC display of the PS or PSA type containing an LC cell having two substrates, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium with application of an electrical voltage to the electrodes, where at least one of the polymerisable compounds is selected from formula I.

The invention furthermore relates to a process for the production of an LC display as described above and below in which an LC medium comprising one or more low-molecular-weight liquid-crystalline compounds or an LC host mixture as described above and below and one or more polymerisable compounds of the formula I or sub-formulae thereof is introduced into an LC cell having two substrates and two electrodes as described above and below, and the polymerisable compounds are polymerised with application of an electrical voltage to the electrodes.

The PS and PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-IPS or PSA-FFS displays according to the invention.

The invention furthermore relates to novel processes for the preparation of compounds of the formula I and to the novel intermediates used or obtained in these processes.

The invention furthermore relates to novel compounds of the formula I.

The following meanings apply above and below:

The term "PSA" is, unless indicated otherwise, used to represent PS displays and PSA displays.

The terms "tilt" and "tilt angle" relate to a tilted alignment of the LC molecules of an LC medium relative to the surfaces of the cell in an LC display (here preferably a PS or PSA display). The tilt angle here denotes the average angle (<90°) between the longitudinal molecular axes of the LC molecules (LC director) and the surface of the plane-parallel outer plates which form the LC cell. A low value of the tilt angle (i.e. a large deviation from the 90° angle) corresponds to a large tilt. A suitable method for measurement of the tilt angle is given in the examples. Unless indicated otherwise, tilt angle values disclosed above and below relate to this measurement method.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

The term "reactive mesogen" or "RM" denotes a compound containing a mesogenic group and one or more functional groups which are suitable for polymerisation (also referred to as polymerisable group or group P).

The terms "low-molecular-weight compound" and "unpolymerisable compound" denote compounds, usually monomeric, which contain no functional group which is suitable for polymerisation under the usual conditions known to the person skilled in the art, in particular under the conditions used for the polymerisation of RMs.

The term "organic group" denotes a carbon or hydrocarbon group.

The term "carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro inks or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ alkyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1'']terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicycle[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" above and below, are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, in which $R^x$ has the meaning indicated above, and $Y^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" preferably means substituted by halogen, —CN, $R^0$, —$OR^0$, —CO—$R^0$, —CO—O—$R^0$, —O—CO—$R^0$ or —O—CO—O—$R^0$, in which $R^0$ has the meaning indicated above.

Particularly preferred substituents L are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

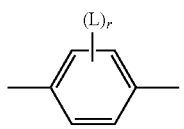

is preferably

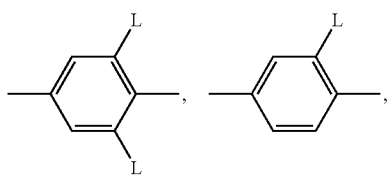

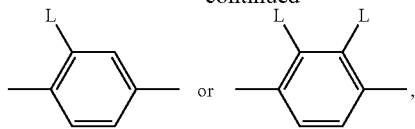

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of $CH_2$=$CW^1$—CO—O—, $CH_2$=$CW^1$—CO—,

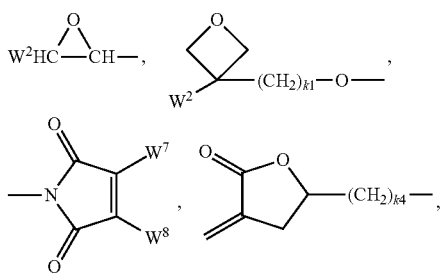

$CH_2$=$CW^2$—(O)$_{k3}$—, $CW^1$=CH—CO—(O)$_{k3}$—, $CW^1$=CH—CO—NH—, $CH_2$=$CW^1$—CO—NH—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe—(O)$_{k2}$—, $CH_2$=CH—(CO)$_{k1}$-Phe—(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are different from P-Sp-, $k_1$, $k_2$ and $k_3$ each, independently of one another, denote 0 or 1, $k_3$ preferably denotes 1, and $k_4$ denotes an integer from 1 to 10.

Particularly preferred groups P are selected from the group consisting of $CH_2$=$CW^1$—CO—O—, $CH_2$=$CW^1$—CO—,

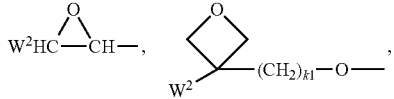

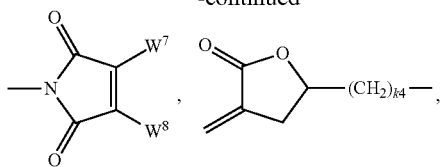

$CH_2=CW^2-O-$, $CW^1=CH-CO-(O)_{k3}-$, $CW^1=CH-CO-NH-$, $CH_2=CW^1-CO-NH-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-CH=CH— and $W^4W^5W^6Si-$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$, $(CH_2=CH)_2CH-O-CO-$, $(CH_2=CH)_2CH-O-$,

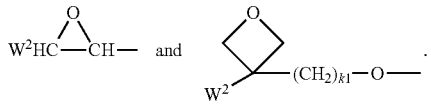

Further very particularly preferred groups P are vinyloxy, acrylate, methacrylate, fluoroacrylate, chloroacrylate, oxetane and epoxy groups, and particularly preferably denote acrylate or methacrylate group.

Preferred spacer groups Sp other than a single bond are selected from the formula Sp'-X'-, so that the radical P-Sp- corresponds to the formula P-Sp'-X'—, where Sp' denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^{00}R^{00}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH=CH— or —C≡C— in such a way that O and/or S atoms are not linked directly to one another, X' denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=C$R^0$—, —CY$^2$=CY$^3$—, —C≡C—, —CH=CH—CO—O—, —O—CO—CH=CH— or a single bond, $R^{00}$ and $R^{00}$ each, independently of one another, denote H or alkyl having 1 to 12 C atoms, and $Y^2$ and $Y^3$ each, independently of one another, denote H, F, Cl or CN.

X' is preferably —O—, —S—, —CO—, —COO—, —OCO—, —O—COO—, —CO—$NR^0$—, —$NR^0$—CO—, —$NR^0$—CO—$NR^0$— or a single bond.

Typical spacer groups Sp' are, for example, —(CH$_2$)$_{p1}$—, —(CH$_2$CH$_2$O)$_{q1}$— —CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O)$_{p1}$—, in which p1 is an integer from 1 to 12, q1 is an integer from 1 to 3, and $R^{00}$ and $R^{000}$ have the meanings indicated above.

Particularly preferred groups Sp'-X'— are —(CH$_2$)$_{p1}$—, —(CH$_2$)$_{p1}$—O—, —(CH$_2$)$_{p1}$—O —CO—, —(CH$_2$)$_{p1}$—O—CO—O—, in which p1 and q1 have the meaning indicated above.

Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

Preference is furthermore given to groups Sp and Sp' which contain one or more C—C triple bonds, in particular those of the formula —(CH$_2$)$_{r1}$—C≡C— or —C≡C—(CH$_2$)$_{r1}$—, in which r1 denotes an integer from 1 to 8, preferably 1, 2 or 3.

In a further preferred embodiment of the invention, $R^a$ and/or $R^b$ in formula I denote a radical containing two or more polymerisable groups (multifunctional polymerisable radicals). Suitable radicals of this type and polymerisable compounds containing them and the preparation thereof are described, for example, in U.S. Pat. No. 7,060,200 B1 or US 2006/0172090 A1. Particular preference is given to multifunctional polymerisable radicals selected from the following formulae:

| | |
|---|---|
| —X-alkyl-CHP$^1$—CH$_2$—CH$_2$P$^2$ | I*a |
| —X-alkyl-C(CH$_2$P$^1$)(CH$_2$P$^2$)—CH$_2$P$^3$ | I*b |
| —X-alkyl-CHP$^1$CHP$^2$—CH$_2$P$^3$ | I*c |
| —X-alkyl-C(CH$_2$P$^1$)(CH$_2$P$^2$)—C$_{aa}$H$_{2aa+1}$ | I*d |
| —X-alkyl-CHP$^1$—CH$_2$P$^2$ | I*e |
| —X-alkyl-CHP$^1$P$^2$ | I*f |
| —X-alkyl-CP$^1$P$^2$—C$_{aa}$H$_{2aa+1}$ | I*g |
| —X-alkyl-C(CH$_2$P$^1$)(CH$_2$P$^2$)—CH$_2$OCH$_2$—C(CH$_2$P$^3$)(CH$_2$P$^4$)CH$_2$P$^5$ | I*h |
| —X-alkyl-CH((CH$_2$)$_{aa}$P$^1$)((CH$_2$)$_{bb}$P$^2$) | I*i |
| —X-alkyl-CH P$^1$CHP$^2$—C$_{aa}$H$_{2aa+1}$ | I*k |
| —X'-alkyl-C(CH$_3$)(CH$_2$P$^1$)(CH$_2$P$^2$) | I*m | in which alkyl denotes a single bond or straight-chain or branched alkylene having 1 to 12 C atoms, in which one or more non-adjacent CH$_2$ groups may each be replaced, independently of one another, by) —C($R^{00}$)=C($R^{000}$)—, —C≡C—, —N ($R^{00}$)—, —O—, —S—, —CO—, —CO—O—, —O—CO—, —O—CO—O— in such a way that O and/or S atoms are not linked directly to one another and in which, in addition, one or more H atoms may be replaced by F, Cl or CN, where $R^{00}$ and $R^{000}$ have the meanings indicated above, aa and bb each, independently of one another, denote 0, 1, 2, 3, 4, 5 or 6, X has one of the meanings indicated for X', and $P^{1-5}$ each, independently of one another, have one of the meanings indicated for P.

Particularly preferred compounds of the formula I are those of the sub-formula IA

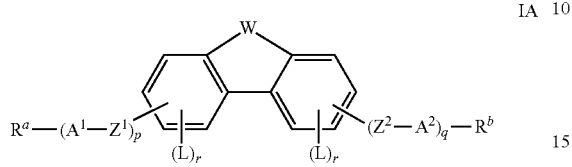

IA in which W, $R^{a,b}$, $A^{1,2}$, $Z^{1,2}$, L, p, q and r have the meanings indicated in formula I.

Particularly preferred compounds of the formulae I and IA and the sub-formulae thereof given above and below are those in which $A^1$ and $A^2$ each, independently of one another, denote 1,4-phenylene, naphthalene-1,4-diyl or naphthalene-2,6-diyl, in which, in addition, one or more CH groups may be replaced by N, cyclohexane-1,4-diyl, in which, in addition, one or more non-adjacent $CH_2$ groups may be replaced by O and/or S, 1,4-cyclohexenylene, bicyclo[1.1.1]pentane-1,3-diyl, bicyclo-[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl, octahydro-4,7-methanoindane-2,5-diyl, phenanthrene-2,7-diyl or anthracene-2,7-diyl, where all these groups may be unsubstituted or mono- or polysubstituted by L, L denotes P, P-Sp-, OH, $CH_2OH$, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, optionally substituted silyl, optionally substituted aryl having 6 to 20 C atoms, straight-chain or branched alkyl or alkoxy having 1 to 25 C atoms, or straight-chain or branched alkenyl, alkynyl, alkylcarbonyl, alkoxycarbonyl, alkylcarbonyloxy or alkoxycarbonyloxy having 2 to 25 C atoms, in which, in addition, one or more H atoms in all these groups may be replaced by F, Cl, P or P-Sp-, $Y^1$ denotes halogen, and $R^x$ denotes P, P-Sp-, H, halogen, straight-chain, branched or cyclic alkyl having 1 to 25 C atoms, in which, in addition, one or more non-adjacent $CH_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl or P-Sp-.

Further preferred compounds of the formulae I and IA and the sub-formulae thereof given above and below are those in which W denotes —C($R^cR^d$)—, —$CH_2CH_2$— or —$CH_2$—O—, $R^c$ and $R^d$ each, independently of one another, denote H, alkyl having 1 to 12, preferably 5 to 12, C atoms, alkoxy having 1 to 12 C atoms or alkenyl having 2 to 11 C atoms, where, in addition, one or more H atoms in all these radicals may be replaced by F, particularly preferably methyl, $R^c$ and $R^d$ denote H, one of the radicals $R^c$ and $R^d$ denotes H and the other is other than H, $R^a$ and $R^b$ denote identical or different radicals P-Sp-, $R^a$ and $R^b$ denote P-Sp-, where Sp in one of the radicals $R^a$ and $R^b$ denotes a single bond and Sp in the other of the radicals $R^a$ and $R^b$ is other than a single bond and preferably denotes a group of the formula Sp'-X', so that this radical P-Sp- conforms to the formula P-Sp'-X'—, $R^a$ and $R^b$ denote identical or different radicals P-Sp- in which both radicals Sp denote a single bond, one of the radicals $R^a$ and $R^b$ denotes or contains a group P-Sp- and the other denotes an unpolymerisable group, preferably selected from straight-chain or branched alkyl having 1 to 25 C atoms, in which, in addition, one or more non-adjacent $CH_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN, $R^a$ denotes P-Sp-, $R^b$ denotes P-Sp-, Sp denotes a single bond, Sp denotes a radical selected from the group consisting of —$(CH_2)_{p1}$—, —$(CH_2)_{p1}$—O—, —$(CH_2)_{p1}$—O—CO—, —$(CH_2)_{p1}$—O—CO—O—, —$(CH_2)_{r1}$—C≡C— and —C≡C—$(CH_2)_{r1}$—, preferably —$(CH_2)_{p1}$— or —$(CH_2)_{p1}$—O—, in which p1 denotes an integer from 1 to 12, and r1 denotes an integer from 1 to 8, L does not denote or contain a polymerisable group, r denotes 1, L denotes F, $A^1$ and $A^2$ are selected from the group consisting of 1,4-phenylene and naphthalene-2,6-diyl, where, in addition, one or two CH groups in these rings may be replaced by N, where these rings may be mono- or polysubstituted by L as described above and below, $Z^1$ and $Z^2$ are selected from the group consisting of —O—, —CO—O—, —OCO—, —$OCH_2$—, —$CH_2O$—, —$CF_2O$—, —$OCF_2$—, —$CH_2CH_2$—, —CH=CH—, —CF=CF—, —CH=CF—, —CF=CH—, —C≡C—, single bond, p denotes 0 or 1, preferably 0, q denotes 0 or 1, preferably 0, L is an unpolymerisable group, preferably selected from F, Cl, —CN and straight-chain or branched alkyl having 1 to 25, particularly preferably 1 to 10, C atoms, in which, in addition, one or more non-adjacent $CH_2$ groups may each be replaced, independently of one another, by) —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN.

Particularly preferred compounds of the formulae I and IA are selected from the group consisting of the following sub-formulae:

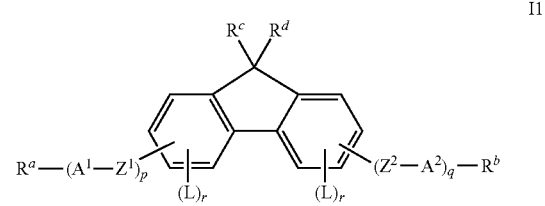

I1

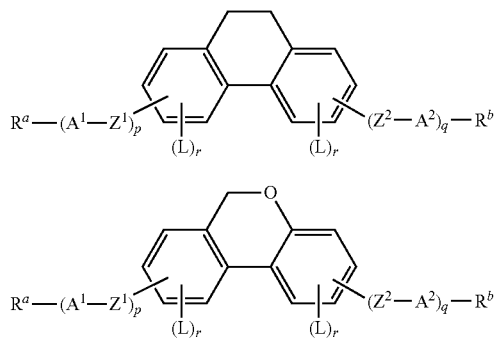

I2

I3 in which $R^{a-d}$, $R^{1,2}$, $A^{1,2}$, L, p, q and r each, independently of one another, have one of the meanings indicated in formula I or above and below.

The groups $-(A^1-Z^1)_p-$ and $-(Z^2-A^2)_q-$ in the compounds of the formulae I, IA, I1, I2 and I3 preferably denote 1,4-phenylene or naphthalene-2,6-diyl, where, in addition, one or two CH groups in these rings may be replaced by N, and where, in addition, these rings may be mono- or polysubstituted by L as described above and below.

Particular preference is given to compounds of the formulae I1 to I3 in which p and q denote 0 and those in which one of the indices p and q denotes 0 and the other denotes 1.

Particular preference is furthermore given to compounds of the formulae I1 to I3 in which the radicals $R^a$ and $R^b$ denote P-Sp- and those in which one of the radicals $R^a$ and $R^b$, preferably $R^a$, denotes P-Sp- and the other denotes an unpolymerisable group, preferably selected from straight-chain or branched alkyl having 1 to 25 C atoms, in which, in addition, one or more non-adjacent CH$_2$ groups may each be replaced, independently of one another, by $-(R^{00})=C(R^{000})-$, $-C\equiv C-$, $-N(R^{00})$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, Br, I or CN.

Particular preference is furthermore given to compounds of the formulae I1 to I3 in which both radicals $R^a$ and $R^b$ denote P-Sp-, where one group Sp denotes a single bond and the other group Sp is other than a single bond.

Very particularly preferred compounds of the formulae I1 to I3 are selected from the group consisting of the following sub-formulae:

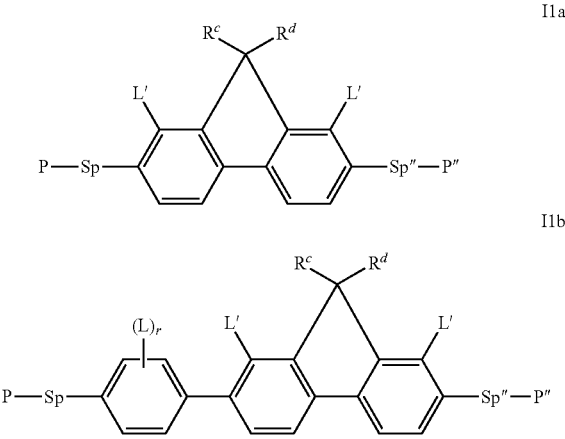

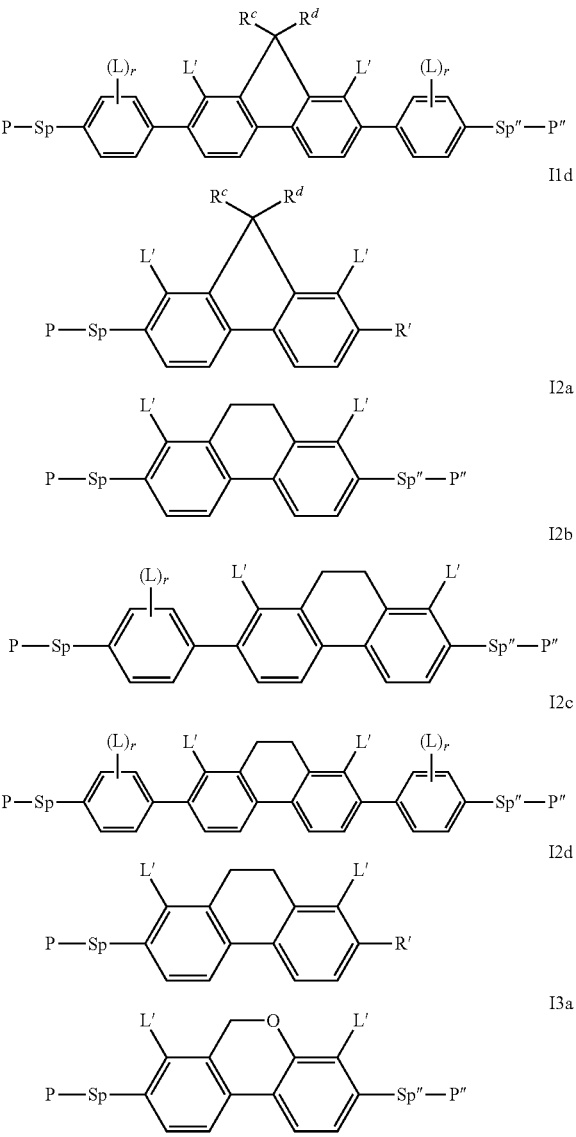

in which $R^c$ and $R^d$ have the meanings indicated above and below, L' denotes H or F, P and Sp have one of the meanings indicated in formula I or above and below, P" has one of the meanings indicated for P in formula I or above and below, Sp" has one of the meanings indicated for Sp in formula I or above and below, and R' has one of the meanings indicated for $R^a$ in formula I or above and below, where R' is other than H and does not denote or contain a group P-Sp-.

P and P''' in the compounds of the formulae I, IA, I1 to I3 and the sub-formulae thereof preferably denote an acrylate, fluoroacrylate or methacrylate group.

Sp and Sp" in the compounds of the formulae I, IA, I1 to I3 and the sub-formulae thereof preferably denote —$(CH_2)_{p1}$—, —O—$(CH_2)_{p1}$—, —$(CH_2)_{p1}$—O—, —O—CO—$(CH_2)_{p1}$—, —$(CH_2)_{p1}$—O—CO—, —O—CO—O—$(CH_2)_{p1}$—, —$(CH_2)_{p1}$—O—CO—O—, —$(CH_2)_{r1}$—C≡C— or —C≡C—$(CH_2)_{r1}$— or a single bond, in which p1 denotes an integer from 1 to 12, preferably 1 to 6, and r1 denotes an integer from 1 to 8, preferably 1, 2 or 3, where these groups are linked to P or P''' in such a way that O atoms are not linked directly to one another.

Particular preference is given to compounds of the sub-formulae I1a-I3d shown above in which one of the two radicals L' denotes F and the other denotes H.

Preference is furthermore given to compounds of the sub-formulae I1a-I3d shown above in which one of the radicals Sp and Sp", preferably Sp, denotes a single bond and the other of the radicals Sp and Sp", preferably Sp", is other than a single bond.

The invention furthermore relates to novel compounds of the formulae I and IA and sub-formulae thereof in which the individual radicals have the meanings indicated in formula I or above and below.

The invention furthermore relates to novel intermediates for the preparation of compounds of the formulae I and IA, selected from the following formula:

IA

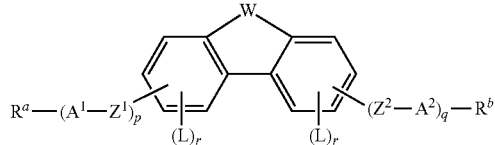

in which W, $A^{1,2}$, $Z^{1,2}$, L, p, q and r have the meanings indicated in formula I or above and below, and the radicals $R^a$ and $R^b$ each, independently of one another, denote -Sp-O—Sg, where Sp has the meaning indicated in formula I or above and below, and Sg denotes an H atom or a protecting group.

Suitable protecting groups Sg are known to the person skilled in the art. Preferred protecting groups are alkyl, acyl and alkylsilyl or arylsilyl groups, 2-tetrahydropyranyl or methoxymethyl.

Particularly preferred intermediates of the formula II are selected from the group consisting of the following sub-formulae:

II1

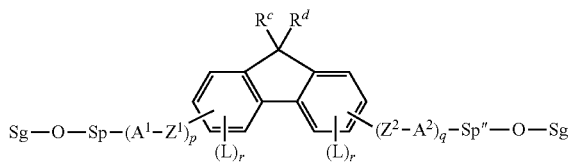

II2

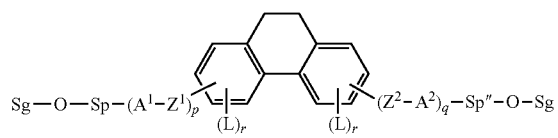

II3

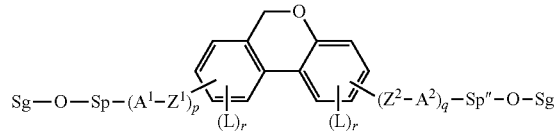

in which $R^{c,d}$, $A^{1,2}$, $Z^{1,2}$, L, p, q, r, Sp and Sg have the meanings indicated in formula II, Sp" has one of the meanings indicated for Sp, and Sg particularly preferably denotes H.

In the compounds of the formulae II1-II3, especially in those of the formula II1, one of the radicals Sp and Sp", preferably Sp, preferably denotes a single bond and the other, preferably Sp", denotes a group other than a single bond.

Of these preferred compounds, particular preference is given to those in which one of the radicals Sp and Sp", preferably Sp, denotes a single bond and the other, preferably Sp", denotes —$(CH_2)_{p1}$—, where p1 is as defined above.

Very particularly preferred intermediates of the formula II are selected from the sub-formulae I1a-I1c, I2a-I2c and I3a-I3c as indicated above in which P denotes Sg—O and P''' denotes O—Sg.

The invention furthermore relates to novel intermediates for the preparation of compounds of the formula I2, selected from the following formula:

III

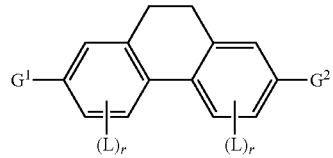

in which L and r have the meanings indicated in formula I, and $G^1$ and $G^2$ denote identical or different radicals selected from Cl, Br, I and OH. Particular preference is given to compounds of the formula III in which $G^1$ and $G^2$ denote identical or different radicals Br or I, those in which one of the groups $G^1$ and $G^2$ denotes I and the other denotes Br or OH, and those in which $G^1$ and $G^2$ denote OH.

Particularly suitable and preferred processes for the preparation of compounds and intermediates of the formulae I, IA, II and III are shown by way of example in the following schemes and preferably comprise one or more of the steps described below.

The compounds and intermediates of the formulae I, IA, II and III and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, the synthesis of compounds of the formulae I and IA is carried out by esterification or etherification of the intermediates of the formula II using corresponding acids, acid derivatives or halogenated compounds containing a group P. As shown by way of example in Scheme 1, esters 2a of acrylic acid or methacrylic acid can be obtained by esterification of the corresponding alcohols 3 using acid derivatives, such as, for example, (meth)acryloyl chloride or (meth)acrylic anhydride, in the presence of a base. Furthermore, the alcohols 3 can also be esterified using (meth)acrylic acid in the presence of a dehydrating agent, for example by the Steglich method using dicyclohexylcarbodiimide (DCC), or by treatment of the corresponding alcohols with (meth)acrylic anhydride in the presence of a base and 4-(N,N-dimethylamino)pyridine (DMAP).

Scheme 1

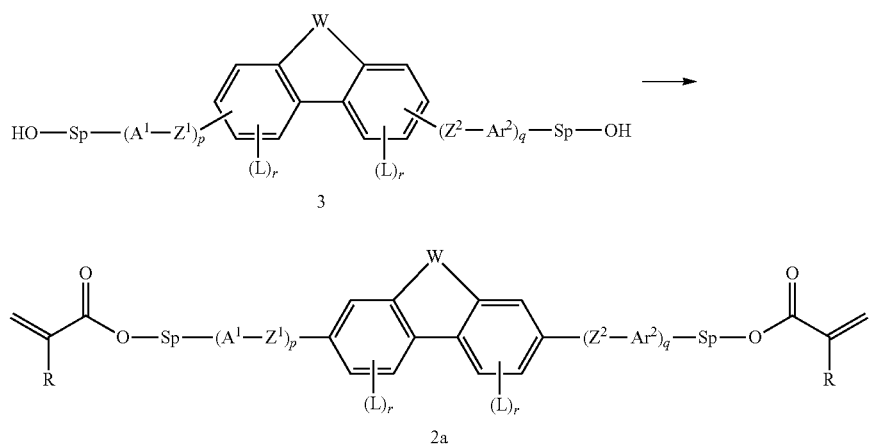

Access to the parent structure 9,10-dihydrophenanthrenene (formula 2 in which W=CH$_2$CH$_2$) is provided by hydrogenation of phenanthrene and can be selectively functionalised by halogenation, as shown by way of example in Scheme 2. The method of A. D. Abell et al., J. Chem. Soc., Perkin Trans, 1, 1997, 1663-1668 starting from 9,10-dihydrophenanthrene 4 gives 2,7-dibromo-9,10-dihydrophenanthrene (formula 5 in which Hal=Br). Iodination by the method of H. Suzuki, Organic Syntheses, Coll. Vol. 6, p. 700 (1988) gives the corresponding 2,7-diiodo-9,10-dihydrophenanthrene (formula 5 in which Hal=Br). 2-Bromo-7-iodo-9,10-dihydrophenanthrene (formula 5 in which one radical Hal denotes Br and the other denotes I), which is not known from the literature to date, is selectively accessible analogously by monoiodination and subsequent bromination and thus opens up the possibility of targeted conversion into a multiplicity of derivatives.

Scheme 2

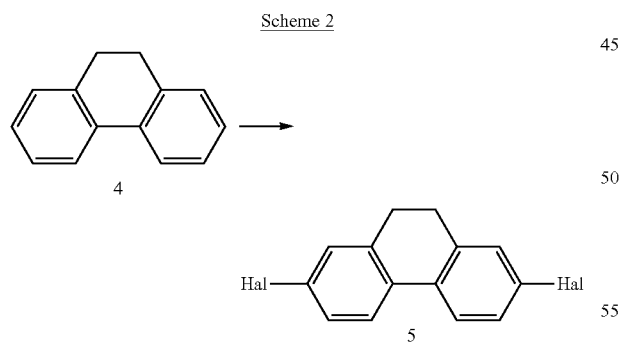

Metallation, for example, of the dihalogen compounds 5 using butyllithium and reaction with boric acid esters enables the preparation of boronic acids, which can be oxidised to the phenols 6, as shown by way of example in Scheme 3. An alternative is treatment with KOH in the presence of palladium catalysts by the method of S. L. Buchwald et al., J. Am. Chem. Soc. 2006, 128, 10694-10695. Esterification using acrylic acids gives the acrylates 7.

Scheme 3

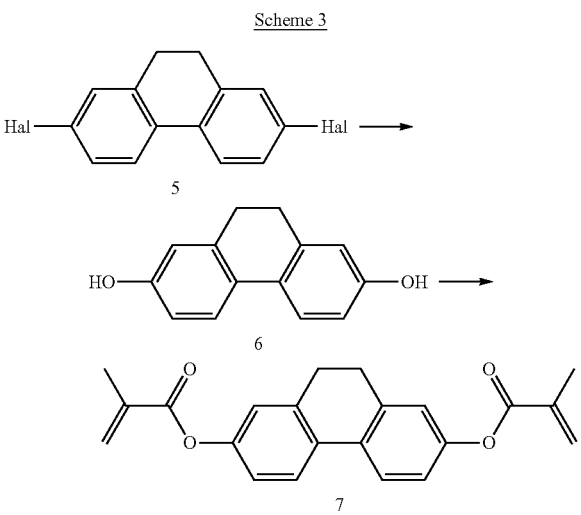

Monometallation in the presence of triisopropyl borate enables monohydroxy compounds 8 to be obtained, which can be converted further in a second step, as shown by way of example in Scheme 4. Thus, Sonogashira coupling to terminal alkynols gives the alkynes 9, from which the compounds 10 containing a spacer group are accessible by hydrogenation and esterification.

Scheme 4

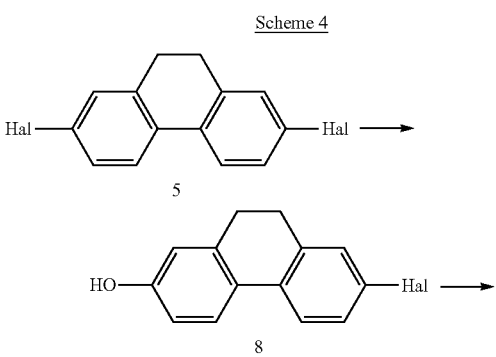

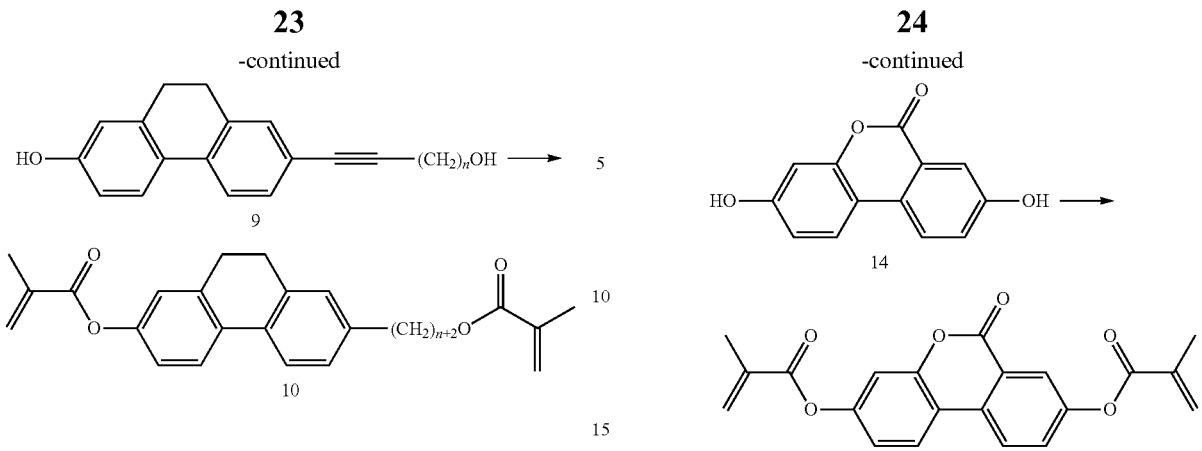

The fluorene derivatives 12 are accessible correspondingly from commercially available dibromofluorene 11, as shown by way of example in Scheme 5 (in which R denotes H or CH$_3$), where the corresponding alkylated derivatives are optionally obtained from 11 by the method of G. R. Bebernitz et al., J. Med. Chem. 2001, 44; 2601-2611. For an alternative preparation of 2,7-dihydroxyfluorenes by Friedel-Crafts acylation and subsequent Baeyer-Villiger oxidation, see R. P. Lemieux et al., J. Materials Chem. 2008, 18(28), 3361-3365.

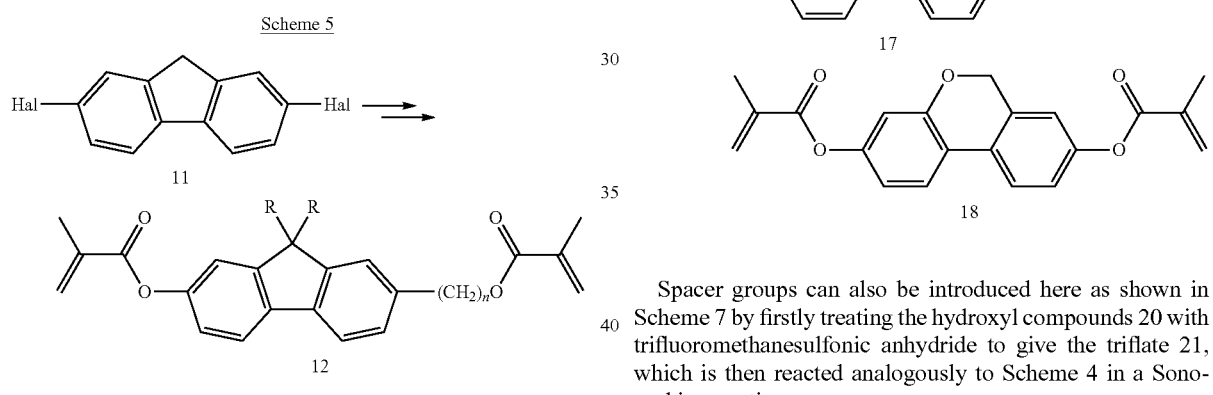

Access to the benzochromenes according to the invention (formula 1 in which W=CH$_2$O) is provided by the method of Taugerbeck, Klasen-Memmer, WO 2004076438, by reduction of the benzochromenones (2 in which W=C(O)O). For the preparation of the benzochromenones, see also, for example, S. Kim et al., Organic Lett. 2005, 7, 411-414; the compound 13 described therein can be converted into the acrylates 15 after ether cleavage using, for example, boron tribromide via 14, as shown by way of example in Scheme 6. The acrylates 18 are accessible correspondingly from 16.

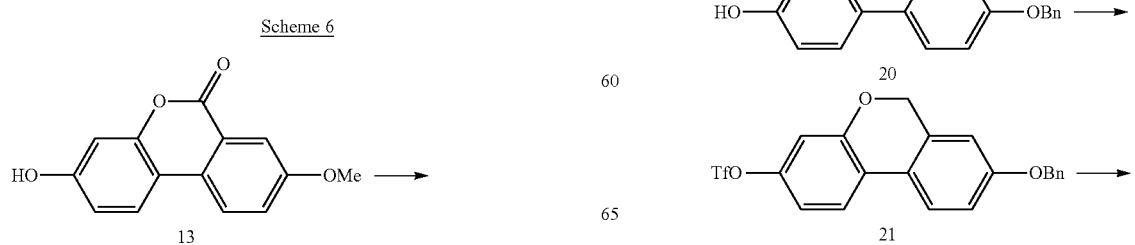

Spacer groups can also be introduced here as shown in Scheme 7 by firstly treating the hydroxyl compounds 20 with trifluoromethanesulfonic anhydride to give the triflate 21, which is then reacted analogously to Scheme 4 in a Sonogashira reaction.

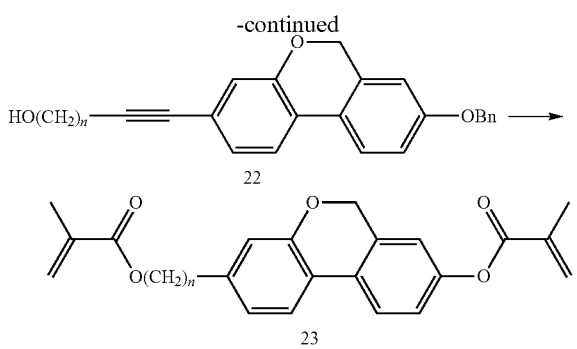

The intermediate compounds shown in the schemes shown above can furthermore be converted into the compounds according to the invention by a multiplicity of standard reactions, as shown by way of example in Scheme 8 (in which the radicals W, X, Sp are as defined above and below, G=H atom or protecting group, and M=B(OH)$_2$, ZnHal or MgHal). For example, transition metal-catalysed coupling reactions, such as the Suzuki coupling (24, M=—B(OH)$_2$), of arylmetal compounds give aryl derivatives 26, which can be converted into the target compounds 27 analogously to the above schemes.

and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight. However, the polymerisation can also be carried out without addition of an initiator. In a further preferred embodiment, the LC medium does not comprise a polymerisation initiator.

The polymerisable component A) or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component A), is preferably 10-10,000 ppm, particularly preferably 50-500 ppm.

The polymerisable compounds according to the invention are also suitable for polymerisation without an initiator, which is accompanied by considerable advantages, such as,

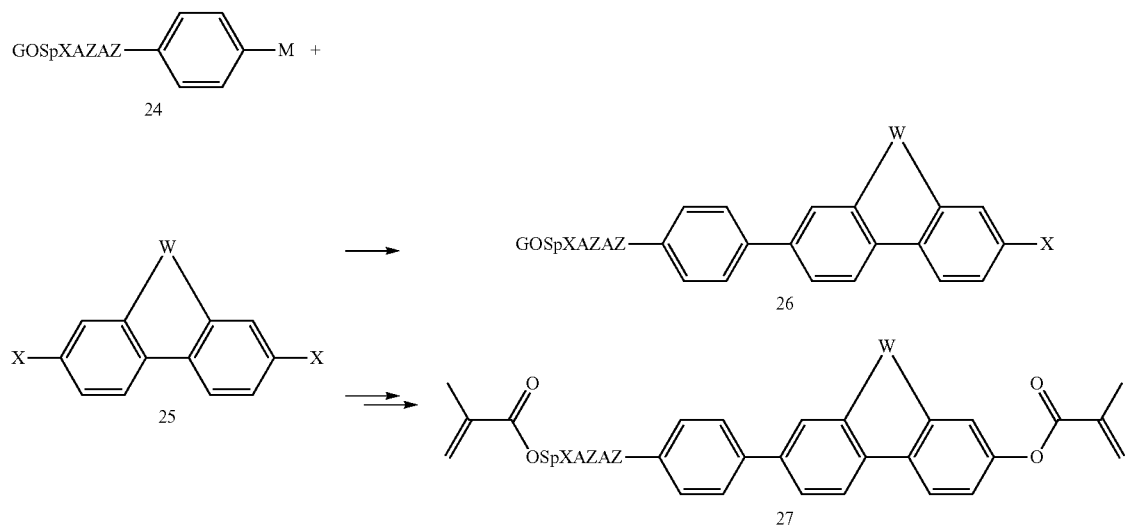

For the production of PSA displays, the polymerisable compounds are polymerised or crosslinked (if one compound contains two or more polymerisable groups) by in-situ polymerisation in the LC medium between the substrates of the LC display with application of a voltage. The polymerisation can be carried out in one step. It is also possible firstly to carry out the polymerisation with application of a voltage in a first step in order to produce a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art for example, lower costs of materials and in particular less contamination of the LC medium by possible residual amounts of the initiator or degradation products thereof.

The LC media according to the invention for use in PSA displays preferably comprise <5% by weight, particularly preferably <1% by weight, very particularly preferably <0.5% by weight, of polymerisable compounds, in particular polymerisable compounds of the formulae given above.

Particular preference is given to LC media comprising one, two or three polymerisable compounds of the formula I.

Preference is furthermore given to LC media in which the polymerisable component (component A) comprises exclusively polymerisable compounds of the formula I.

Preference is furthermore given to LC media in which component B) is an LC compound or an LC mixture which has a nematic liquid-crystal phase.

Preference is furthermore given to achiral polymerisable compounds of the formula I and LC media in which the compounds of component A) and/or B) are selected exclusively from the group consisting of achiral compounds.

Preference is furthermore given to LC media in which the polymerisable component or component A) comprises one or more polymerisable compounds of the formula I containing one polymerisable group (mono-reactive) and one or more polymerisable compounds of the formula I containing two or more, preferably two, polymerisable groups (di- or multi-reactive).

Preference is furthermore given to PSA displays and LC media in which the polymerisable component or component A) comprises exclusively polymerisable compounds of the formula I containing two polymerisable groups (direactive).

The proportion of the polymerisable component or component A) in the LC media according to the invention is preferably <5%, particularly preferably <1%, very particularly preferably <0.5%.

The proportion of the liquid-crystalline component or component B) in the LC media according to the invention is preferably >95%, particularly preferably >99%.

The polymerisable compounds of the formula I can be polymerised individually, but it is also possible to polymerise mixtures which comprise two or more compounds of the formula I, or mixtures comprising one or more compounds of the formula I and one or more further polymerisable compounds (comonomers), which are preferably mesogenic or liquid-crystalline. In the case of polymerisation of such mixtures, copolymers form. The invention furthermore relates to the polymerisable mixtures mentioned above and below. The polymerisable compounds and comonomers are mesogenic or non-mesogenic, preferably mesogenic or liquid-crystalline.

Suitable and preferred mesogenic comonomers, particularly for use in PSA displays, are selected, for example, from the following formulae:

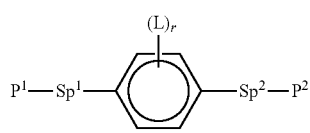

M1

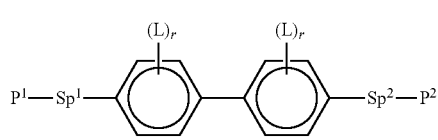

M2

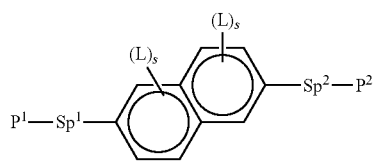

M3

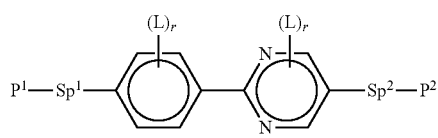

M4

-continued

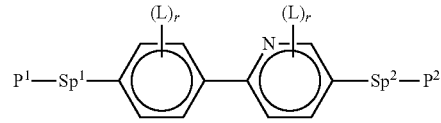

M5

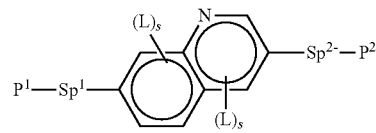

M6

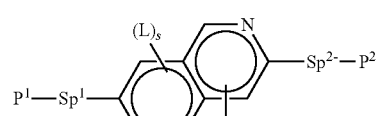

M7

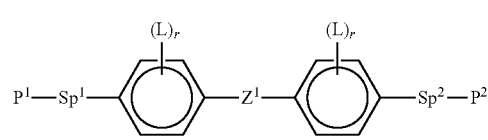

M8

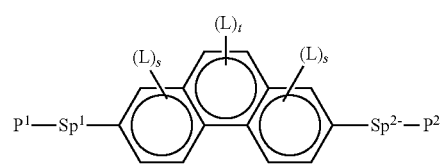

M9

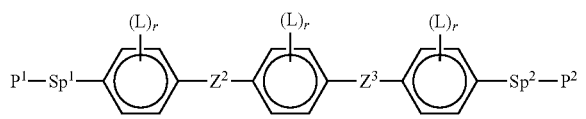

M10

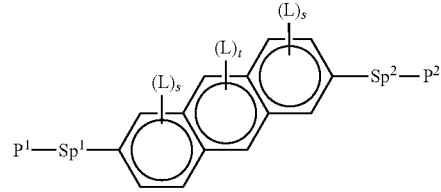

M11

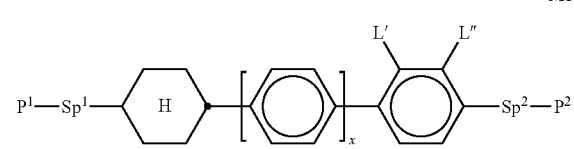

M12

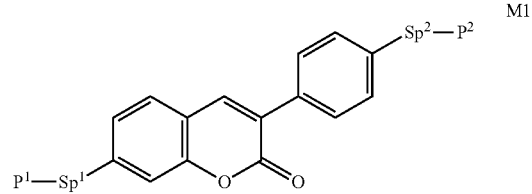

M13

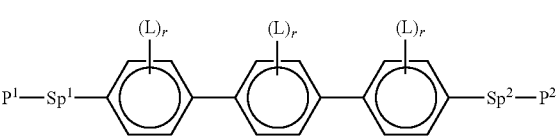

M14

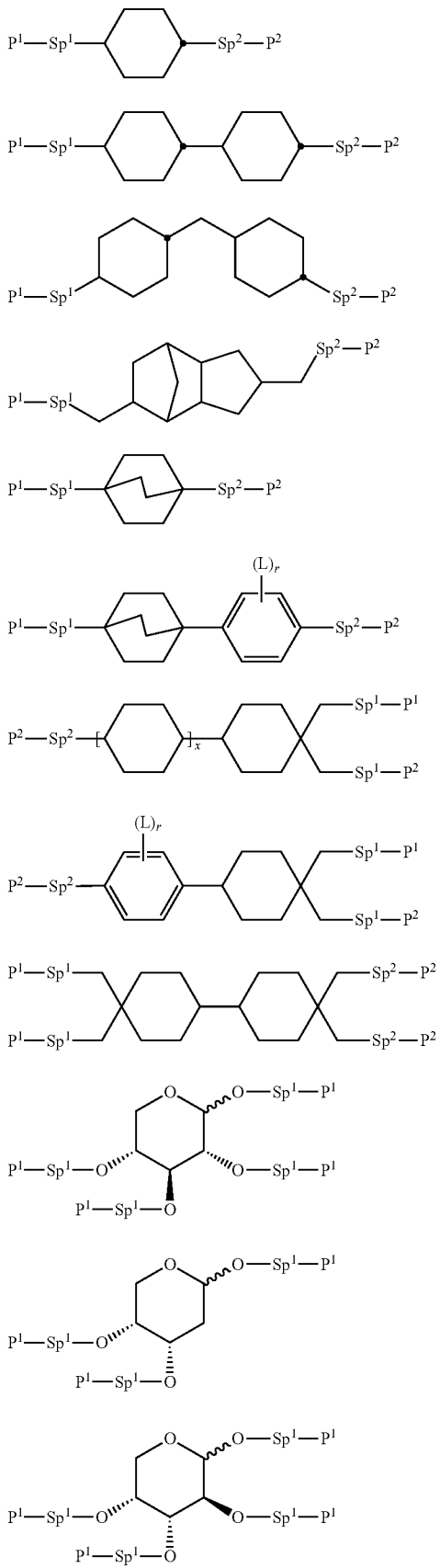

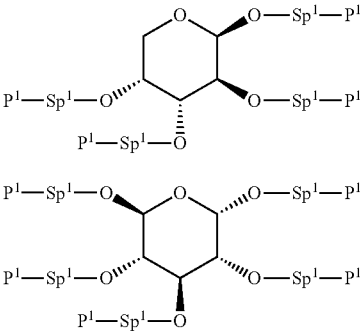

in which the individual radicals have the following meanings:

$P^1$ and $P^2$ each, independently of one another, denote a polymerisable group, preferably having one of the meanings indicated above and below for P, particularly preferably an acrylate, methacrylate, fluoroacrylate, oxetane, vinyloxy or epoxide group, $Sp^1$ and $Sp^2$ each, independently of one another, denote a single bond or a spacer group, preferably having one of the meanings indicated above and below for Sp, and particularly preferably denote —$(CH_2)_{p1}$—, —$(CH_2)_{p1}$—O—, —$(CH_2)_{p1}$—CO—O— or —$(CH_2)_{p1}$—O—CO—O—, in which p1 is an integer from 1 to 12, and where the linking to the adjacent ring in the last-mentioned groups takes place via the O atom, where, in addition, one or more of the radicals $P^1$-$Sp^1$- and $P^2$-$Sp^2$-may denote $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)$=$C(R^{00})$—, —C≡C—, —$N(R^0)$—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $Z^1$ denotes —O—, —CO—, —$C(R^yR^z)$— or —$CF_2CF_2$—

$Z^2$ and $Z^3$ each, independently of one another, denote —CO—O—, —O—CO—, —$CH_2O$—, —$OCH_2$—, —$CF_2O$—, —$OCF_2$— or —$(CH_2)_n$—, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1 or 3, t denotes 0, 1 or 2,
x denotes 0 or 1.

Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for polymerisation of the polymerisable compounds. In principle, any LC mixture which is suitable for use in conventional VA and OCB displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

Particularly preferred LC displays, LC host mixtures and LC media are mentioned below:
a) LC medium which comprises one or more compounds of the formulae CY and/or PY:

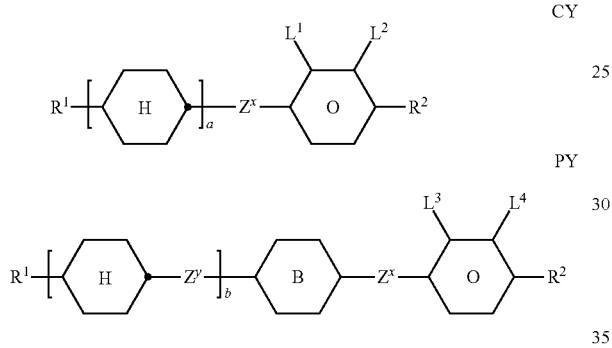

in which the individual radicals have the following meanings:
a denotes 1 or 2,
b denotes 0 or 1,

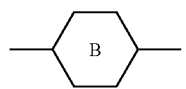

denotes

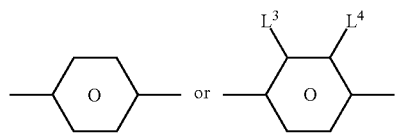

$R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^{1-4}$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl, or both radicals $L^3$ and $L^4$ denote F or one of the radicals $L^3$ and $L^4$ denotes F and the other denotes Cl.

The compounds of the formula CY are preferably selected from the group consisting of the following sub-formulae:

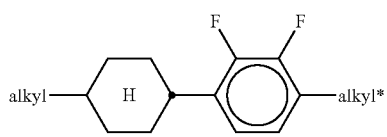

CY1

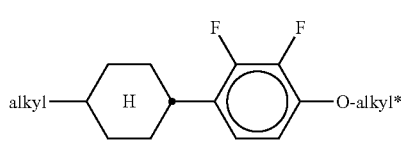

CY2

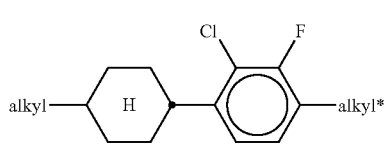

CY3

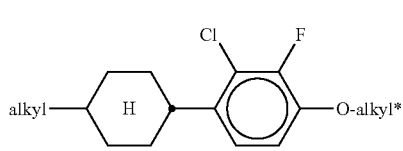

CY4

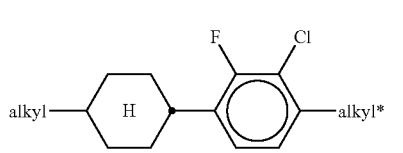

CY5

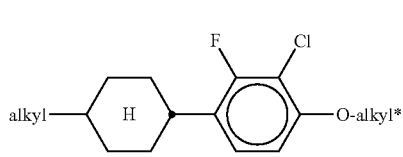

CY6

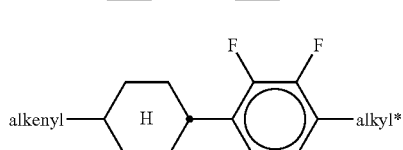

CY7

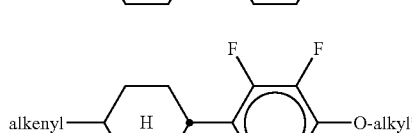

CY8

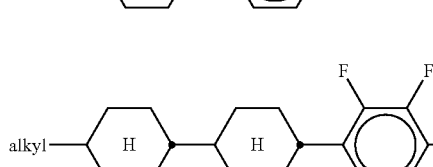

CY9

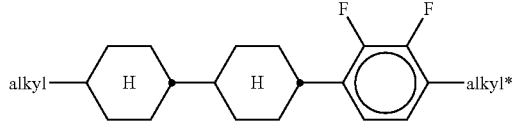

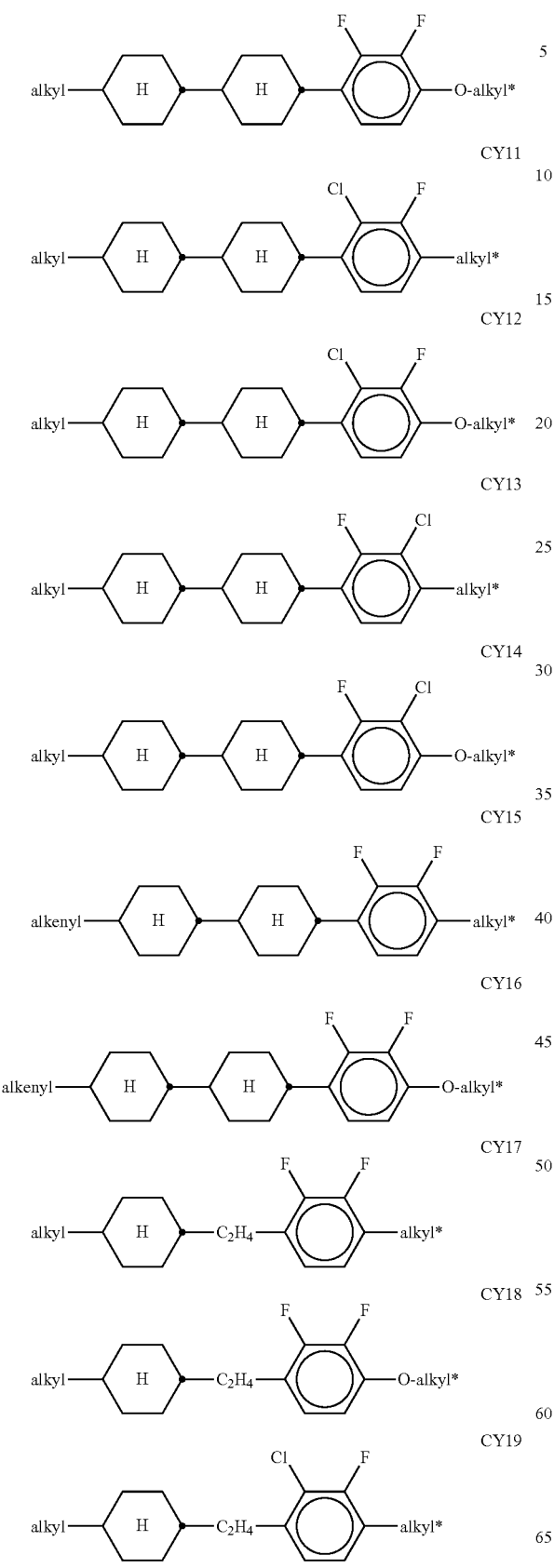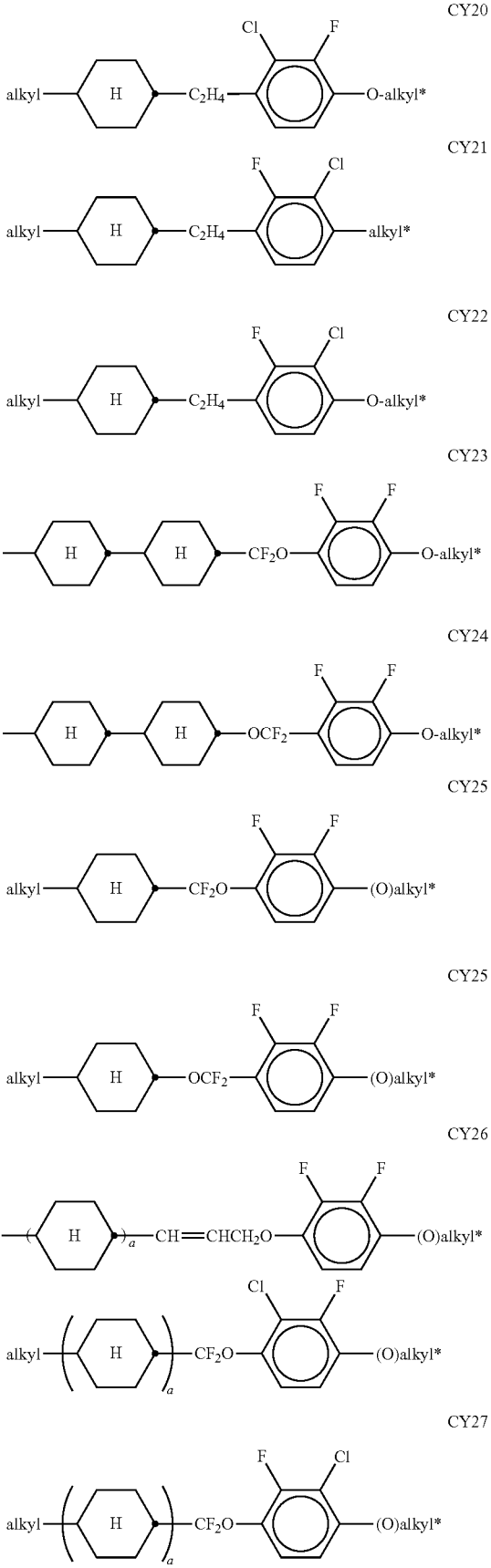

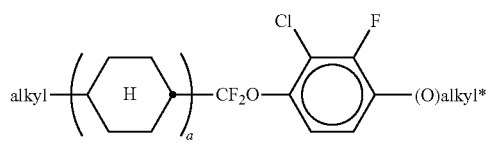
CY28 in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

The compounds of the formula PY are preferably selected from the group consisting of the following sub-formulae:

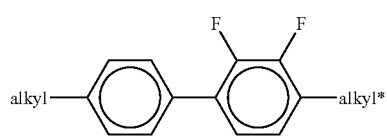
PY1

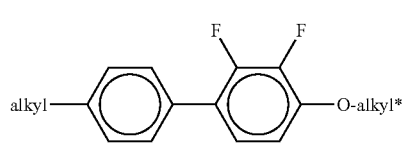
PY2

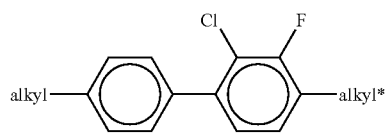
PY3

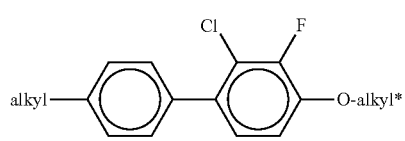
PY4

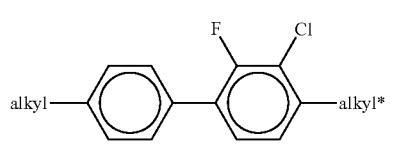
PY5

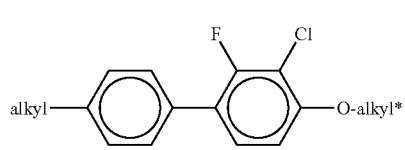
PY6

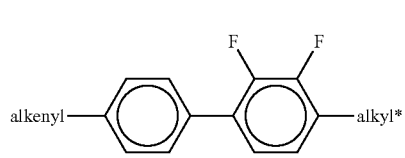
PY7

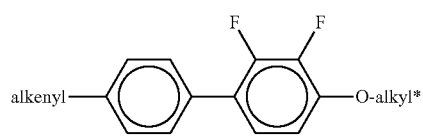
PY8

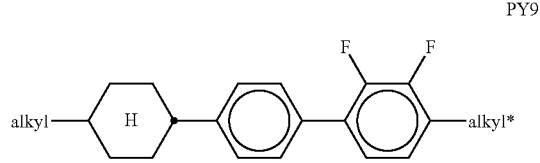
PY9

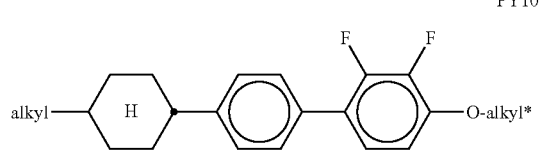
PY10

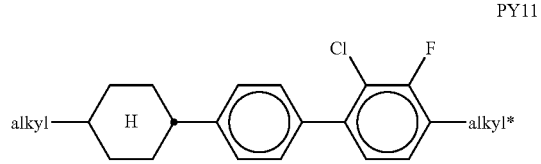
PY11

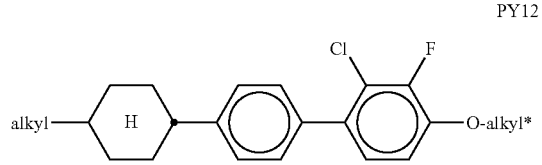
PY12

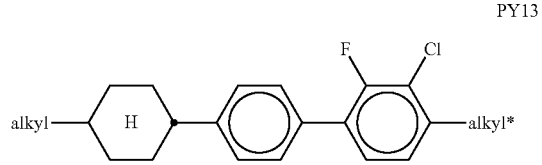
PY13

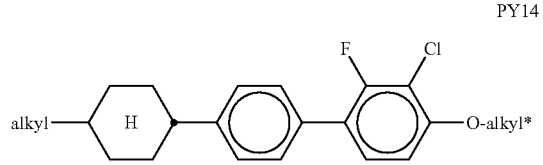
PY14

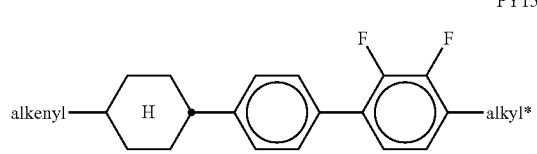
PY15

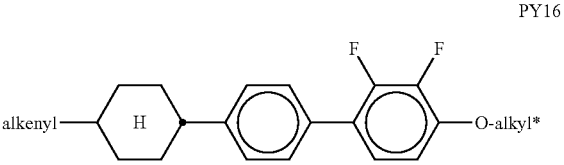
PY16

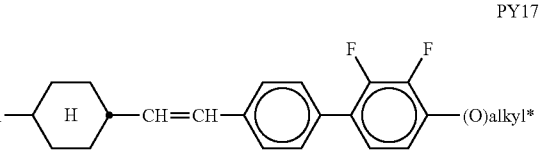
PY17

-continued

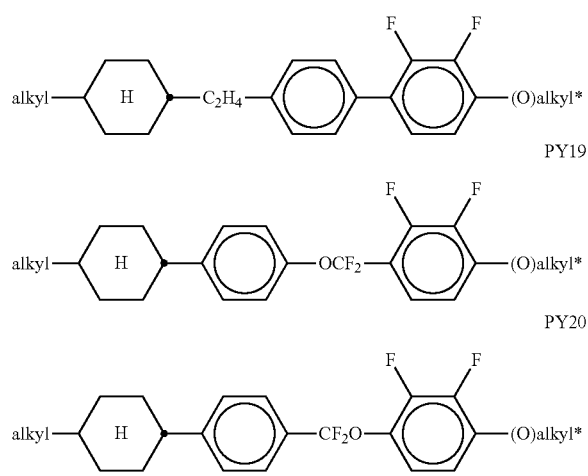

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

b) LC medium which additionally comprises one or more compounds of the following formula:

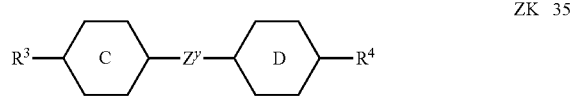

in which the individual radicals have the following meanings:

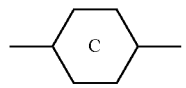

denotes

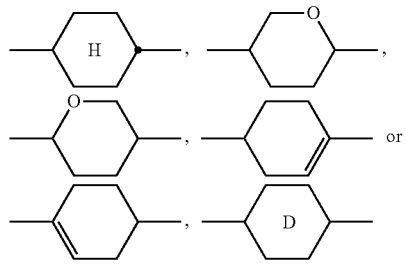

denotes

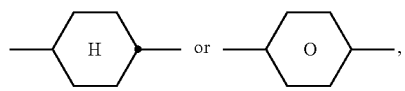

$R^3$ and $R^4$ each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

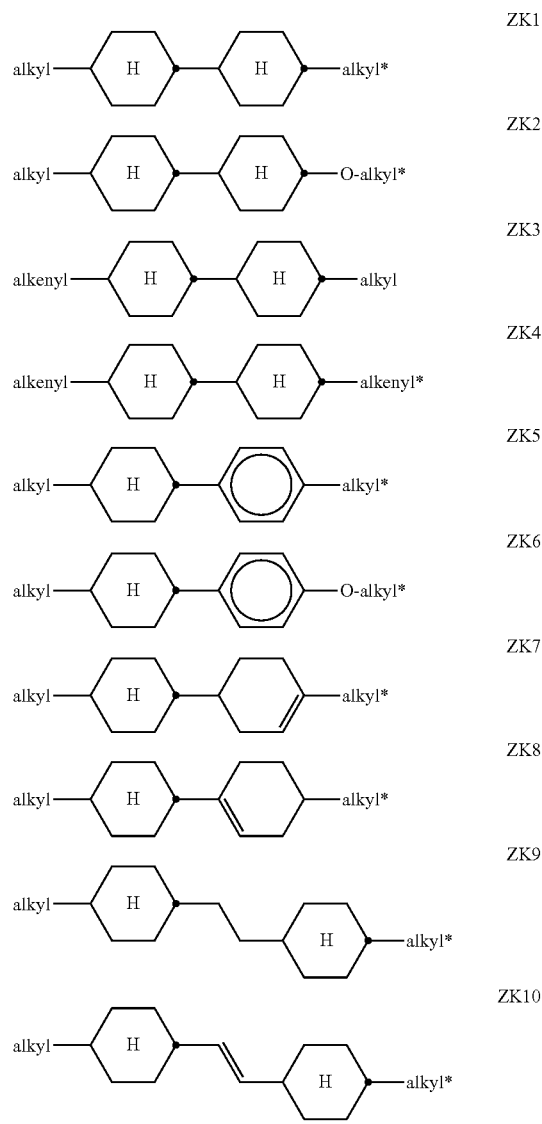

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

c) LC medium which additionally comprises one or more compounds of the following formula:

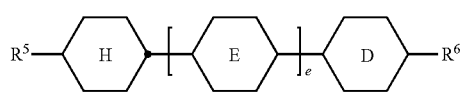
DK in which the individual radicals on each occurrence, identically or differently, have the following meanings:

R$^5$ and R$^6$ each, independently of one another, have one of the meanings indicated above for R$^1$,

denotes

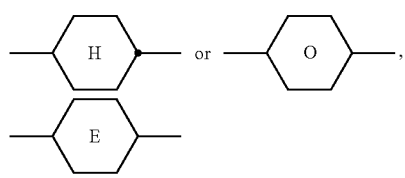

denotes

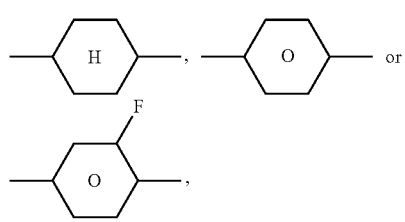

and e denotes 1 or 2.

The compounds of the formula DK are preferably selected from the group consisting of the following sub-formulae:

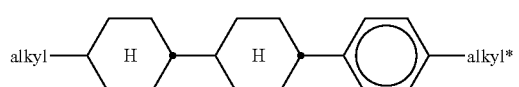
DK1

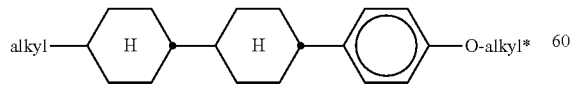
DK2

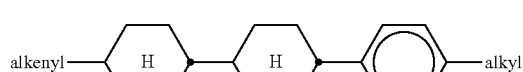
DK3

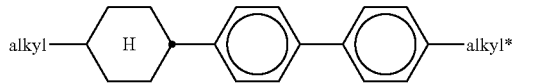
DK4

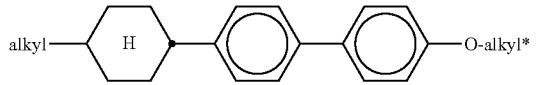
DK5

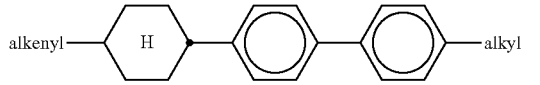
DK6

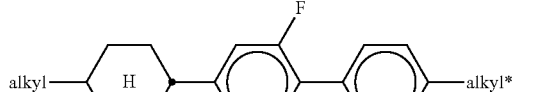
DK7

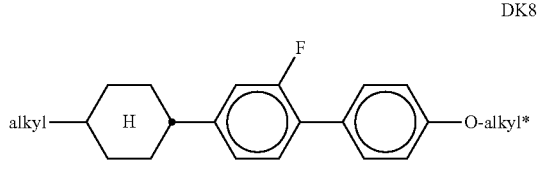
DK8

DK9

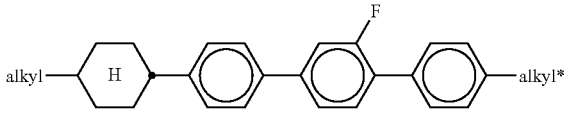
DK10

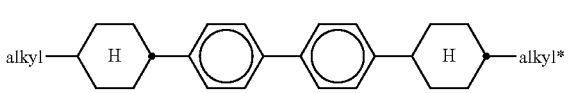
DK11

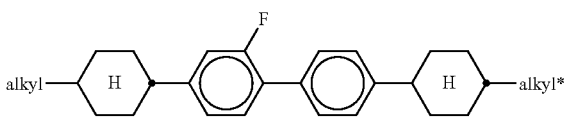

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

d) LC medium which additionally comprises one or more compounds of the following formula:

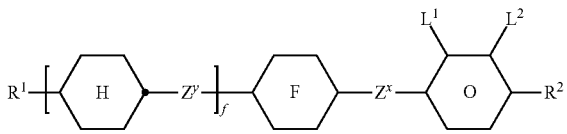
LY in which the individual radicals have the following meanings:

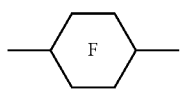

denotes

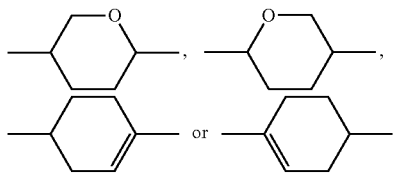

f denotes 0 or 1,

R¹ and R² each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, $Z^x$ and $Z^y$ each, independently of one another, denote —CH₂CH₂—, —CH=CH—, —CF₂O—, —OCF₂—, —CH₂O—, —OCH₂—, —CO—O—, —O—CO—, —C₂F₄—, —CF=CF—, —CH=CH—CH₂O— or a single bond, preferably a single bond, L¹ and L² each, independently of one another, denote F, Cl, OCF₃, CF₃, CH₃, CH₂F, CHF₂.

Preferably, both radicals L¹ and L² denote F or one of the radicals L¹ and L² denotes F and the other denotes Cl.

The compounds of the formula LY are preferably selected from the group consisting of the following sub-formulae:

LY1
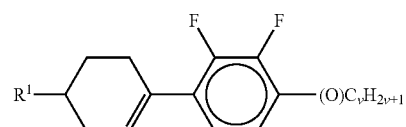

LY2
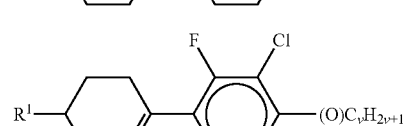

LY3
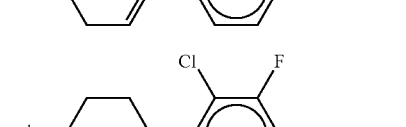

LY4
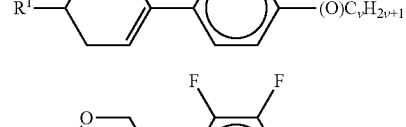

LY5
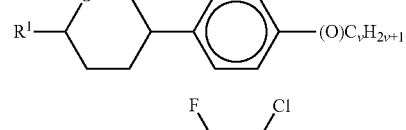

LY6
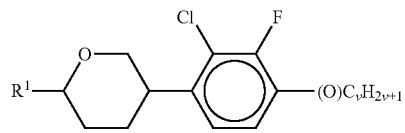

LY7
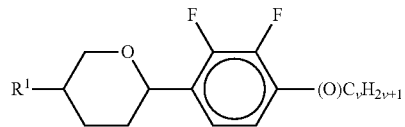

LY8
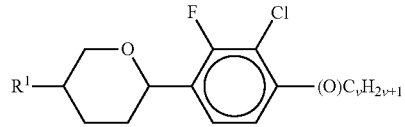

LY9
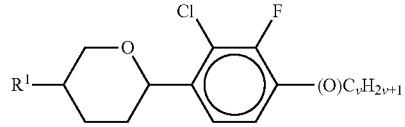

LY10
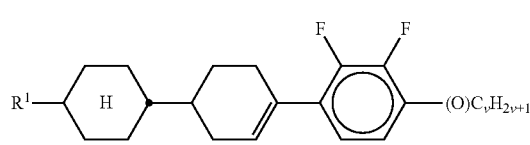

LY11
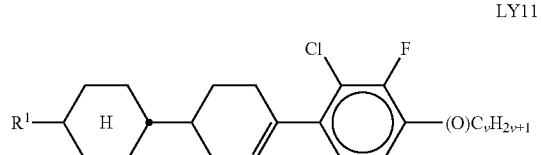

LY12
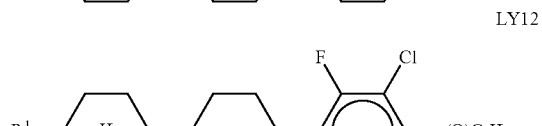

LY13
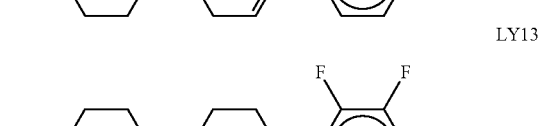

LY14
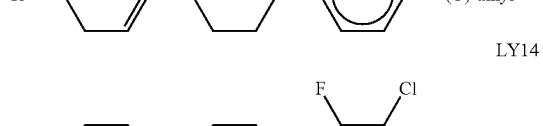

LY15
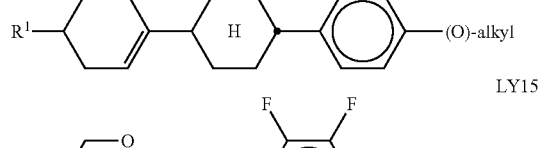

LY16
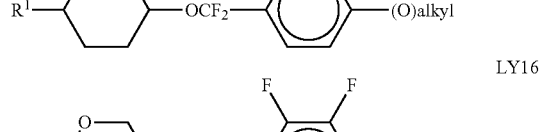

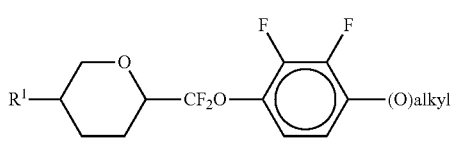
LY17

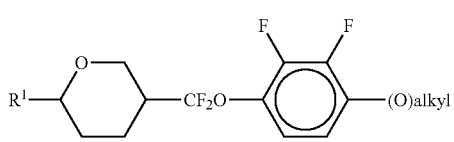
LY18 in which R¹ has the meaning indicated above, alkyl denotes a straight-chain alkyl radical having 1-6 C atoms, (O) denotes an oxygen atom or a single bond, and v denotes an integer from 1 to 6. R¹ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2$=CH—, $CH_2$=CHCH$_2$CH$_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

e) LC medium which additionally comprises one or more compounds selected from the group consisting of the following formulae:

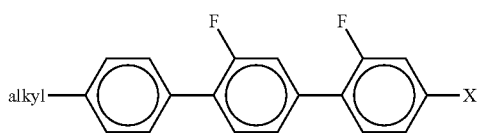
G1

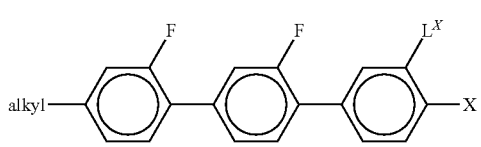
G2

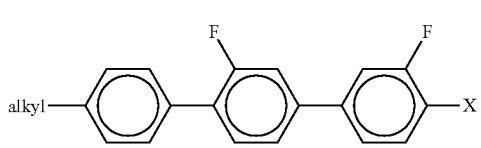
G3

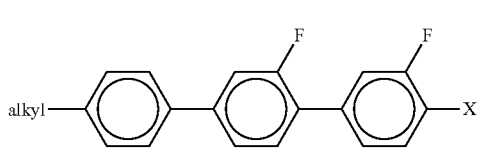
G4 in which alkyl denotes $C_{1-6}$-alkyl, $L^x$ denotes H or F, and X denotes F, Cl, $OCF_3$, $OCHF_2$ or OCH=$CF_2$. Particular preference is given to compounds of the formula G1 in which X denotes F.

f) LC medium which additionally comprises one or more compounds selected from the group consisting of the following formulae:

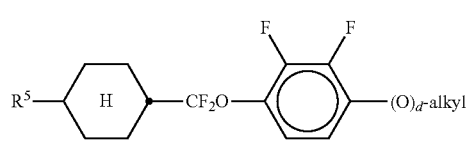
Y1

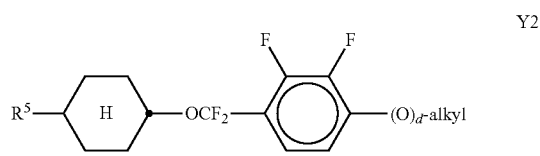
Y2

Y3

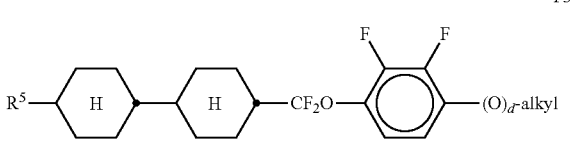

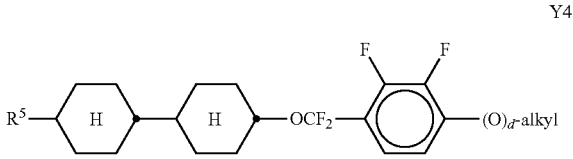
Y4

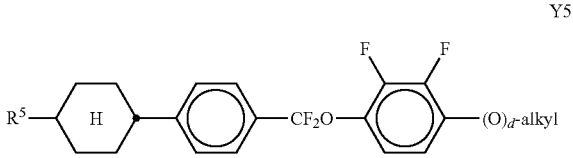
Y5

Y6

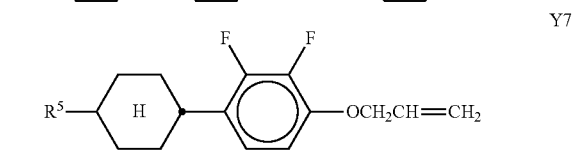
Y7

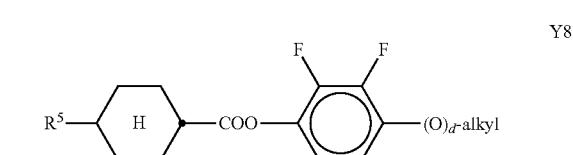
Y8

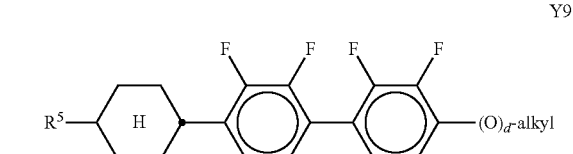
Y9

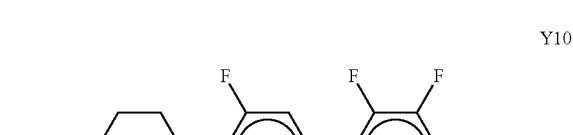
Y10

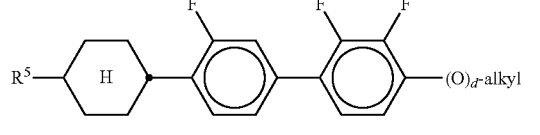

-continued

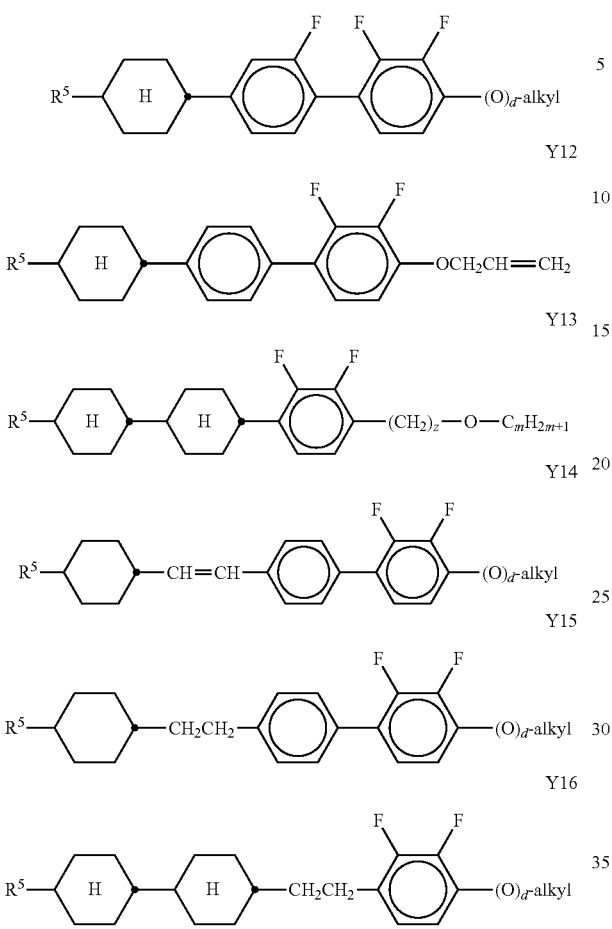

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the abovementioned formulae in amounts of ≥5% by weight.

g) LC medium which additionally comprises one or more biphenyl compounds selected from the group consisting of the following formulae:

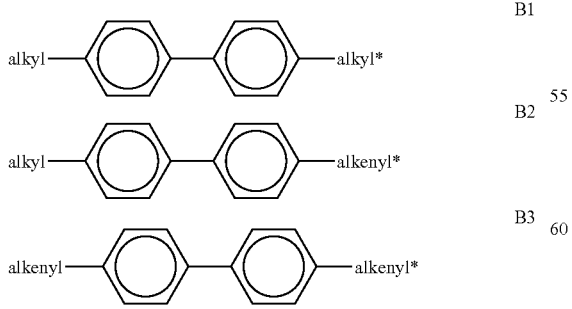

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—CH=CH—, $CH_3$—CH$_2$—CH=CH—, $CH_3$—$(CH_2)_2$—CH=CH—, $CH_3$—$(CH_2)_3$—CH=CH— or $CH_3$—CH=CH—$(CH_2)_2$—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

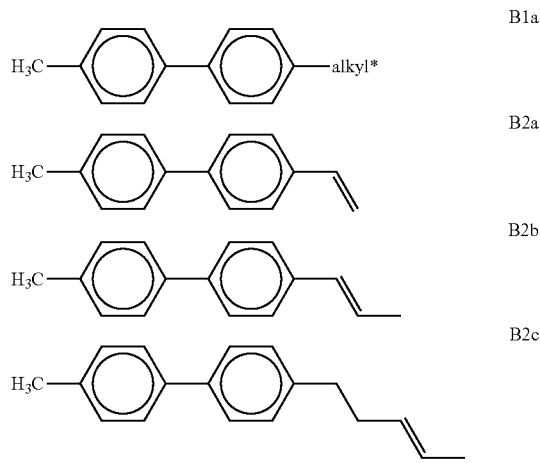

in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

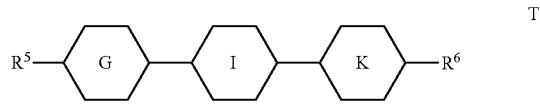

in which $R^5$ and $R^6$ each, independently of one another, have one of the meanings indicated above for $R^1$, and

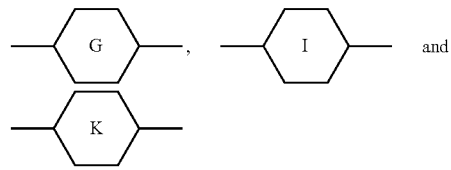

each, independently of one another, denote

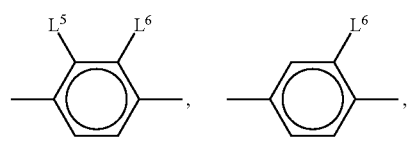

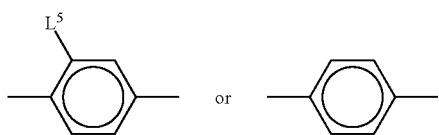
in which L⁵ denotes F or Cl, preferably F, and L⁶ denotes F, Cl, OCF$_3$, CF$_3$, CH$_3$, CH$_2$F or CHF$_2$, preferably F.
The compounds of the formula T are preferably selected from the group consisting of the following sub-formulae:
T1
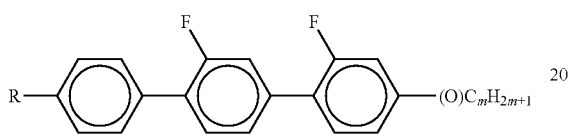
T2
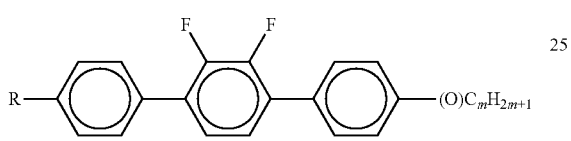
T3
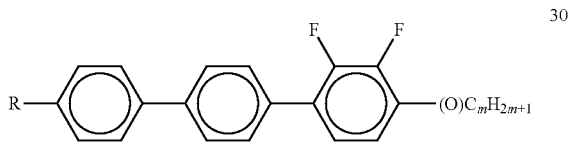
T4
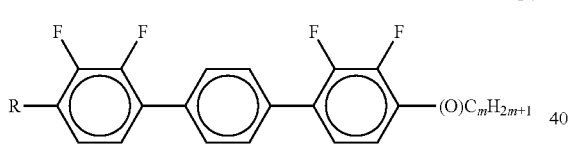
T5
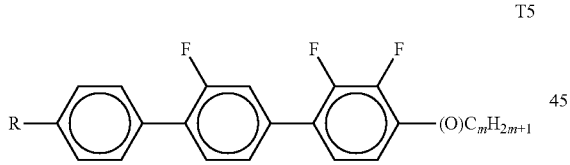
T6
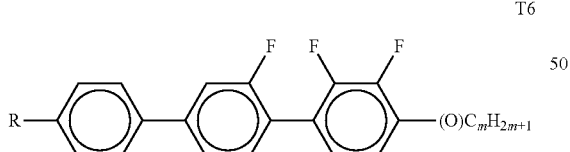
T7
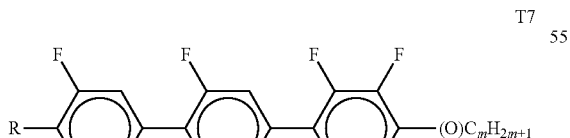
T8
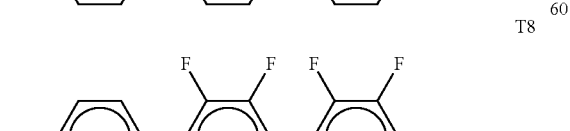
T9
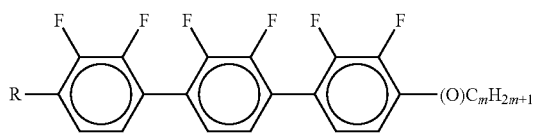
T10
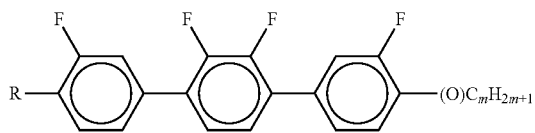
T11
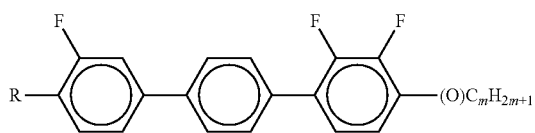
T12
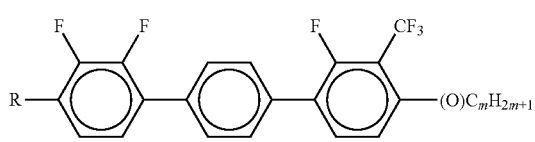
T13
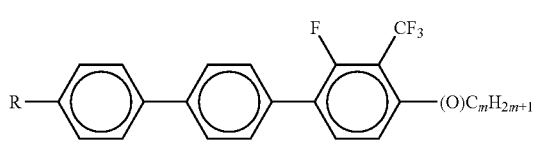
T14
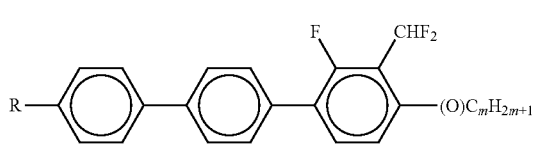
T15
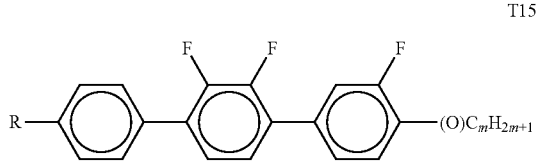
T16
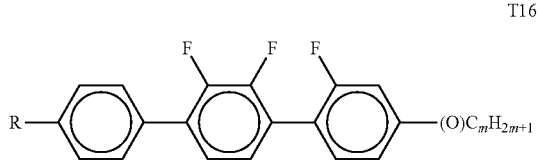
T17
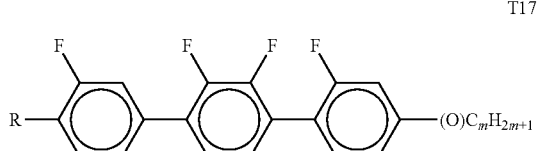
T18
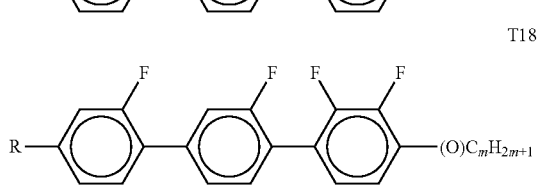

-continued

T19, T20, T21, T22, T23, T24

O1, O2, O3, O4, O5, O6, O7, O8, O9, O10, O11 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 2-30% by weight, in particular 5-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

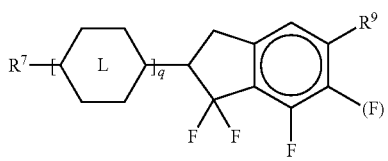

in which

denotes

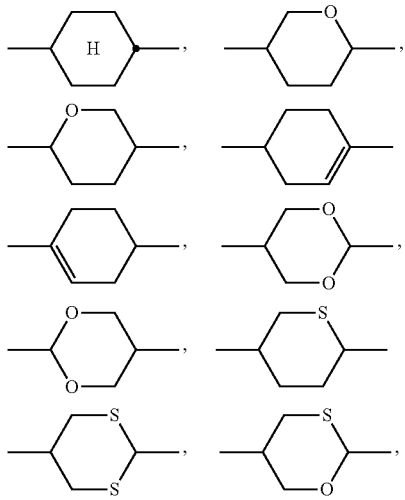

$R^9$ denotes H, $CH_3$, $C_2H_5$ or $n$-$C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

in which $R^7$ preferably denotes straight-chain alkyl, and $R^9$ denotes $CH_3$, $C_2H_5$ or $n$-$C_3H_7$. Particular preference is given to the compounds of the formulae FI1, FI2 and FI3.

m) LC medium which additionally comprises one or more compounds selected from the group consisting of the following formulae:

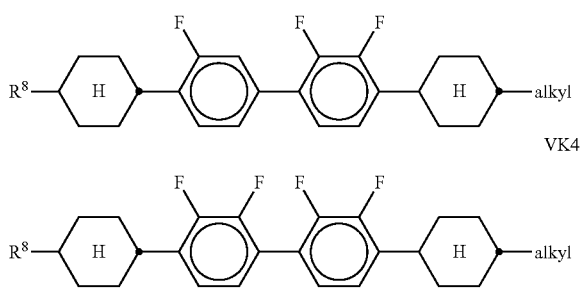

in which R⁸ has the meaning indicated for R¹, and alkyl denotes a straight-chain alkyl radical having 1-6 C atoms.

n) LC medium which additionally comprises one or more compounds which contain a tetrahydronaphthyl or naphthyl unit, such as, for example, the compounds selected from the group consisting of the following formulae:

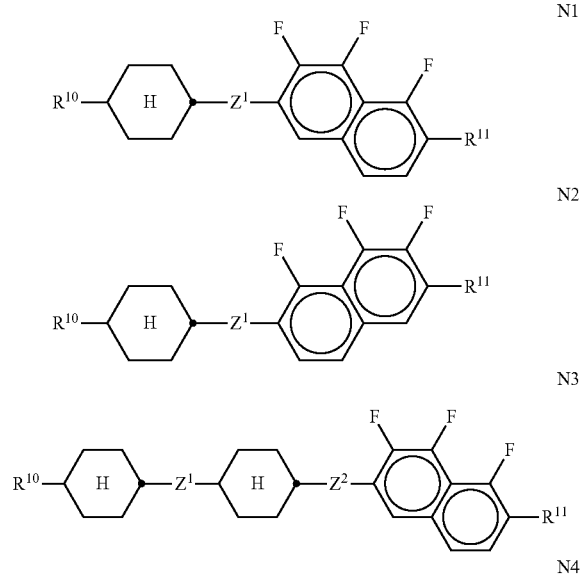

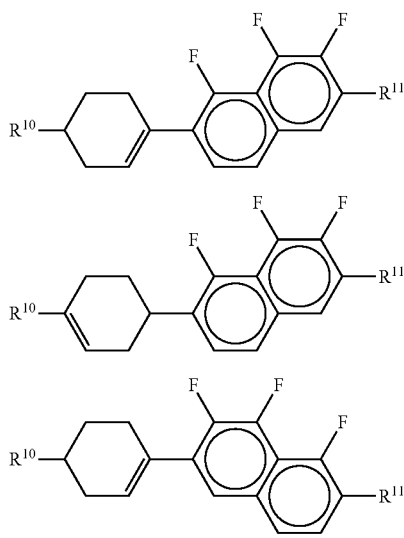

in which $R^{10}$ and $R^{11}$ each, independently of one another, have one of the meanings indicated for $R^1$, preferably denote straight-chain alkyl or alkoxy having 1 to 6 C atoms or straight-chain alkenyl having 2 to 6 C atoms, and $Z^1$ and $Z^2$ each, independently of one another, denote —C₂H₄—, —CH═CH—, —(CH₂)₄—, —(CH₂)₃O—, —O(CH₂)₃—, —CH═CH—CH₂CH₂—, —CH₂CH₂CH═CH—, —CH₂O—, —OCH₂—, —CO—O—, —O—CO—, —C₂F₄—, —CF═CF—, —CF═CH—, —CH═CF—, —CH₂— or a single bond.

o) LC medium which additionally comprises one or more difluoro-dibenzochromans and/or chromans of the following formulae:

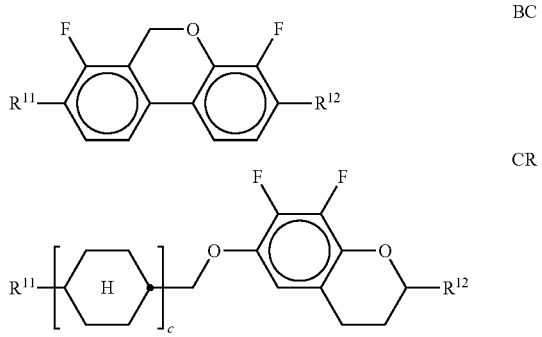

in which $R^{11}$ and $R^{12}$ each, independently of one another, have the meanings indicated above, and c denotes 0 or 1, preferably in amounts of 3 to 20% by weight, in particular in amounts of 3 to 15% by weight.

Particularly preferred compounds of the formulae BC and CR are selected from the group consisting of the following sub-formulae:

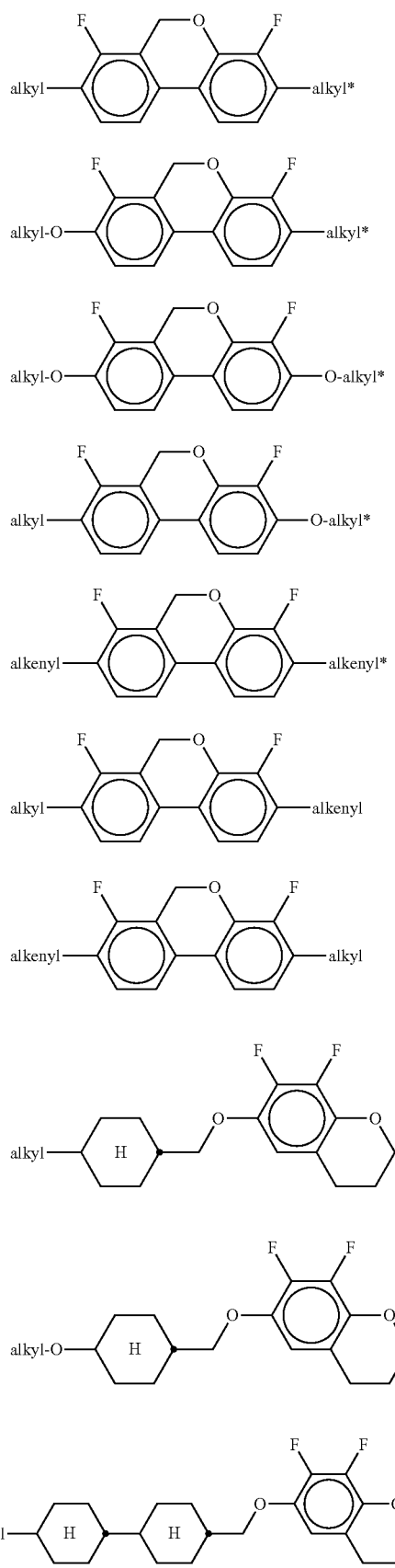
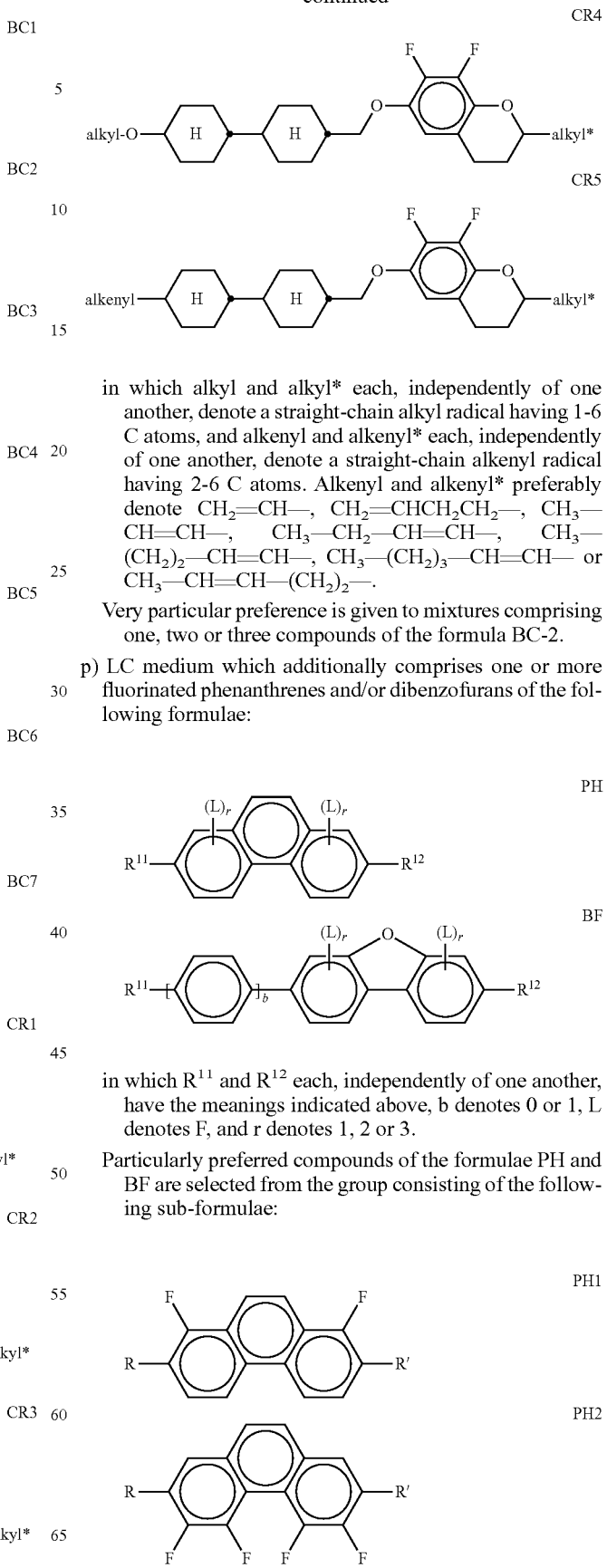

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

p) LC medium which additionally comprises one or more fluorinated phenanthrenes and/or dibenzofurans of the following formulae:

in which $R^{11}$ and $R^{12}$ each, independently of one another, have the meanings indicated above, b denotes 0 or 1, L denotes F, and r denotes 1, 2 or 3.

Particularly preferred compounds of the formulae PH and BF are selected from the group consisting of the following sub-formulae:

-continued

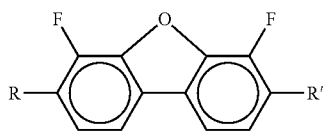
BF1

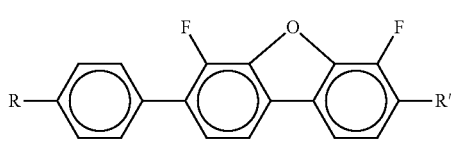
BF2 in which R and R' each, independently of one another, denote a straight-chain alkyl or alkoxy radical having 1-7 C atoms.

q) LC medium, preferably for use in PSA-OCB displays, which comprises one or more compounds selected from the group consisting of the following formulae:

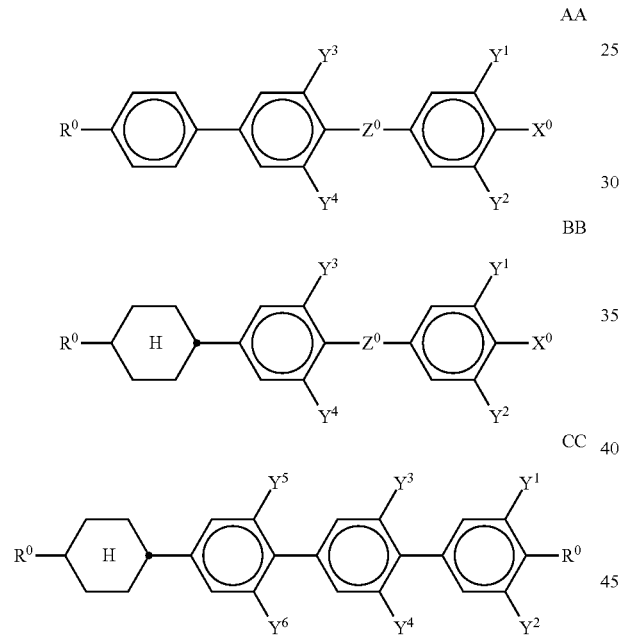

AA

BB

CC in which $R^0$ on each occurrence, identically or differently, denotes n-alkyl, alkoxy, oxaalkyl, fluoroalkyl or alkenyl, each having up to 9 C atoms, $X^0$ denotes F, Cl or in each case halogenated alkyl, alkenyl, alkenyloxy or alkoxy, each having up to 6 C atoms, $Z^0$ denotes —$CF_2O$— or a single bond, $Y^{1-6}$ each, independently of one another, denote H or F.

$X^0$ is preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or $CH=CF_2$, particularly preferably F or $OCF_3$.

The compounds of the formula AA are preferably selected from the group consisting of the following formulae:

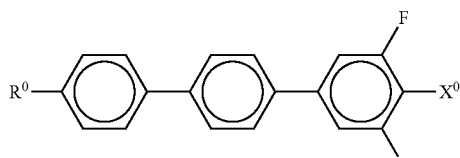
AA1

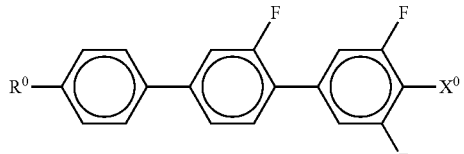
AA2

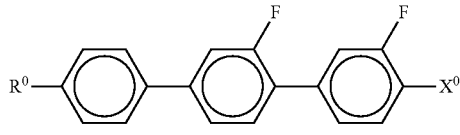
AA3

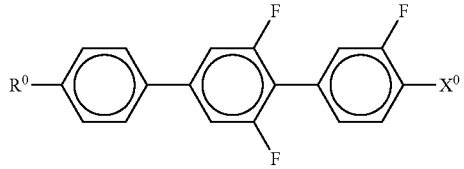
AA4

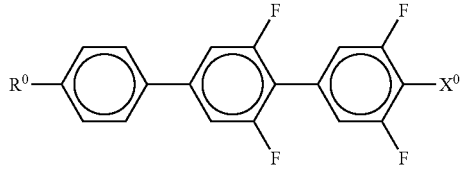
AA5

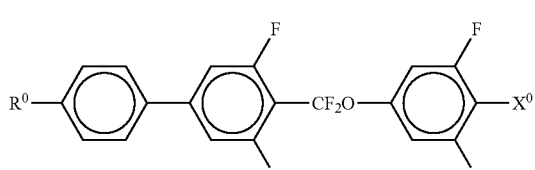
AA6

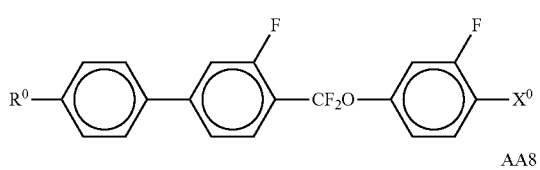
AA7

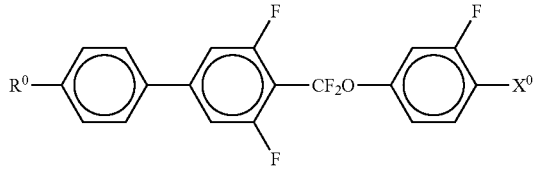
AA8

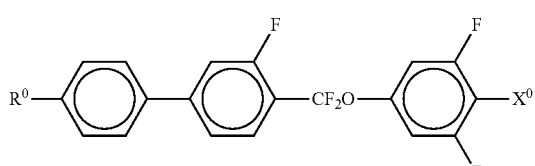
AA9 in which R⁰ and X⁰ have the meanings indicated above, and X⁰ preferably denotes F. Particular preference is given to compounds of the formulae AA2 and AA6.

The compounds of the formula BB are preferably selected from the group consisting of the following formulae:

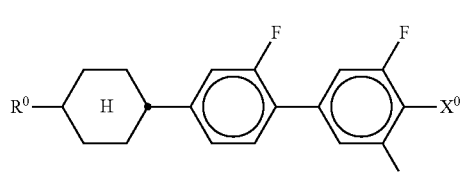
BB1

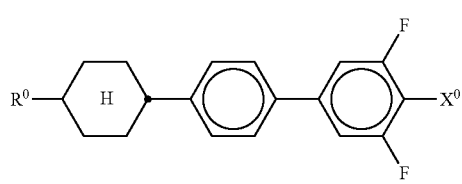
BB2

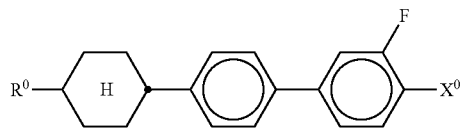
BB3

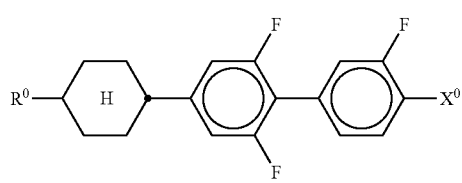
BB4

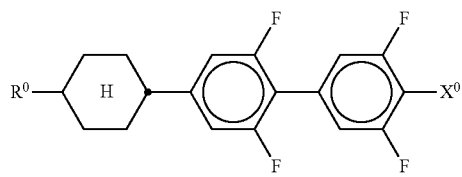
BB5

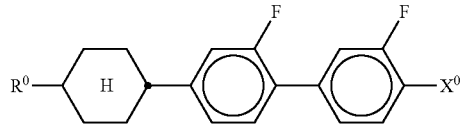
BB6 in which R⁰ and X⁰ have the meanings indicated above, and X⁰ preferably denotes F. Particular preference is given to compounds of the formulae BB1, BB2 and BB5.

The compounds of the formula CC are preferably selected from the following formula:

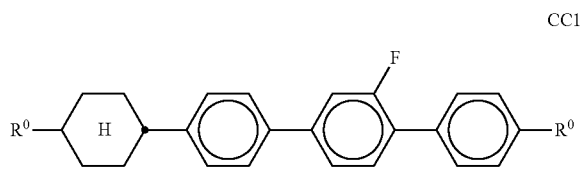
CC1 in which R⁰ on each occurrence, identically or differently, has the meaning indicated above and preferably denotes alkyl having 1 to 6 C atoms.

r) LC medium which, apart from the polymerisable compounds of the formula I or sub-formulae thereof and the comonomers, comprises no compounds which contain a terminal vinyloxy group (—O—CH=CH₂).

s) LC medium which comprises 1 to 5, preferably 1, 2 or 3, polymerisable compounds.

t) LC medium in which the proportion of polymerisable compounds in the mixture as a whole is 0.05 to 5%, preferably 0.1 to 1%.

u) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

v) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

w) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the mixture as a whole is greater than 70%, preferably greater than 80%.

y) PSA-VA display in which the pretilt angle is preferably ≤85°, particularly preferably ≤80°.

The combination of compounds of the preferred embodiments a)-y) mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C.

LC media according to the invention for use in displays of the VA type have negative dielectric anisotropy Δϵ, preferably of about −0.5 to −10, in particular about −2.5 to −7.5, at 20° C. and 1 kHz.

In the VA-type displays according to the invention, the molecules in the layer of the LC medium in the switched-off state are aligned perpendicular to the electrode surfaces (homeotropically) or have a a tilted homeotropic aligment. On application of an electrical voltage to the electrodes, a realignment of the LC molecules takes place with the longitudinal molecular axes parallel to the electrode surfaces.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the OCB type have positive dielectric anisotropy Δϵ, preferably of about +7 to +17 at 20° C. and 1 kHz.

The birefringence Δn in LC media according to the invention for use in displays of the VA type is preferably less than 0.16, particularly preferably between 0.06 and 0.14, in particular between 0.07 and 0.12.

The birefringence Δn in LC media according to the invention for use in displays of the OCB type is preferably between 0.14 and 0.22, in particular between 0.16 and 0.22.

The LC media according to the invention may also comprise further additives which are known to the person skilled in the art and are described in the literature, such as, for example, polymerisation initiators, inhibitors, stabilisers, surface-active substances or chiral dopants. These may be polymerisable or non-polymerisable. Polymerisable additives are accordingly ascribed to the polymerisable component or component A). Non-polymerisable additives are accordingly ascribed to the non-polymerisable component or component B).

The LC media may, for example, comprise one or more chiral dopants, preferably those selected from the group consisting of compounds from Table B below.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the LC displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:
(m, m, z: in each case, independently of one another, 1, 2, 3, 4, 5 or 6)

TABLE A

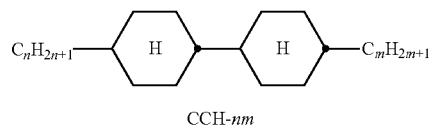

CCH-nm

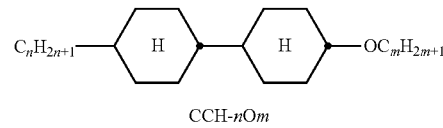

CCH-nOm

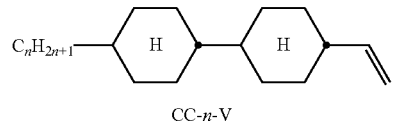

CC-n-V

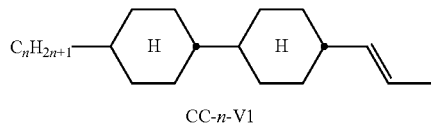

CC-n-V1

TABLE A-continued
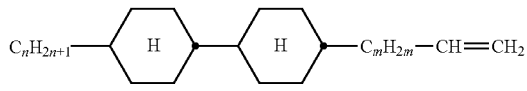
CC-n-mV
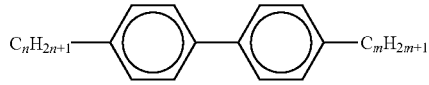
PP-n-m
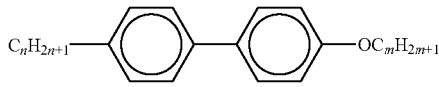
PP-n-Om
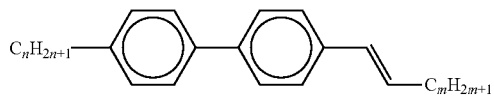
PP-n-Vm
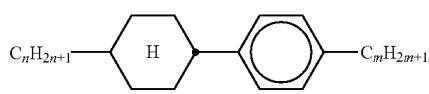
PCH-nm
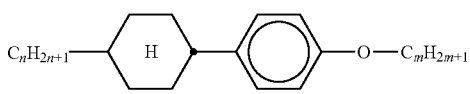
PCH-nOm
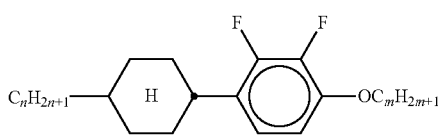
CY-n-Om
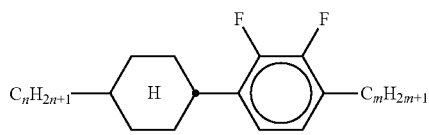
CY-n-m
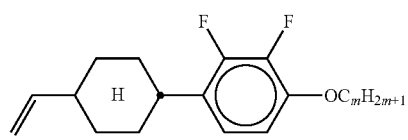
CY-V-Om
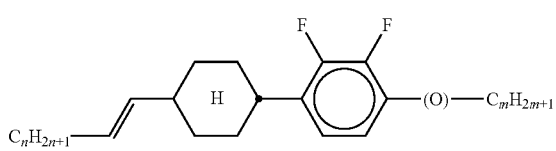
CY-nV-(O)m TABLE A-continued
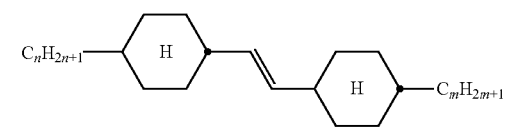
CVC-n-m
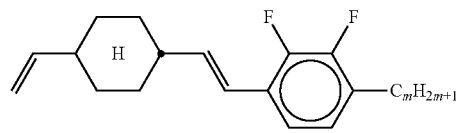
CVY-V-m
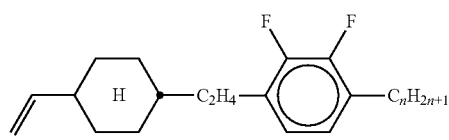
CEY-V-m
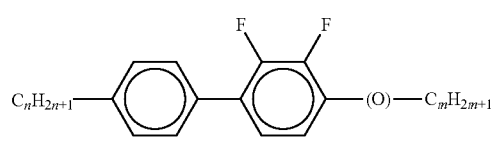
PY-n-(O)m
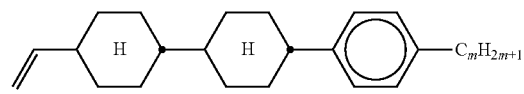
CCP-V-m
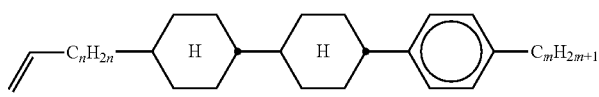
CCP-Vn-m
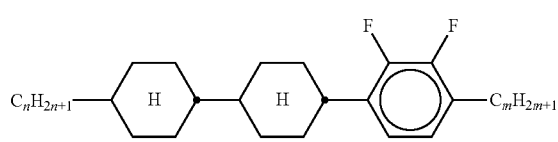
CCY-n-m
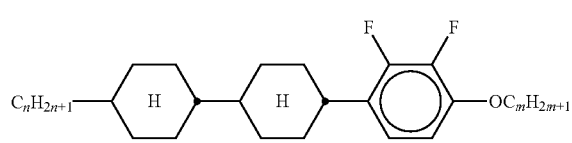
CCY-n-Om
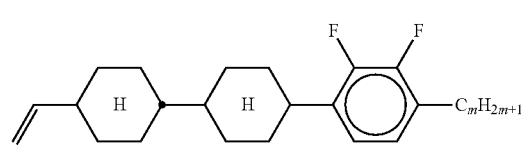
CCY-V-m TABLE A-continued
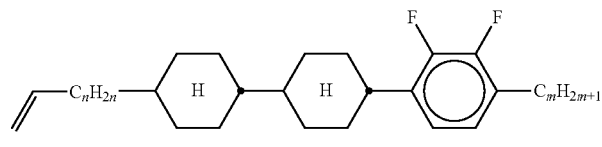
CCY-Vn-m
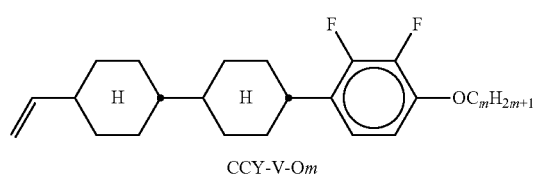
CCY-V-Om
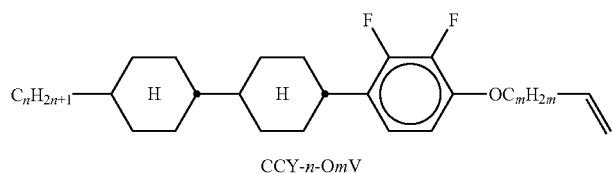
CCY-n-OmV
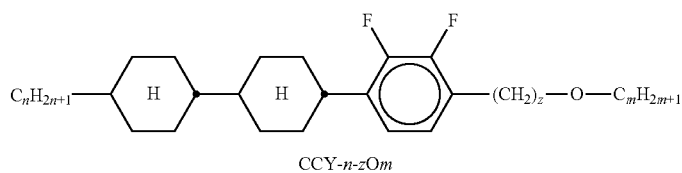
CCY-n-zOm
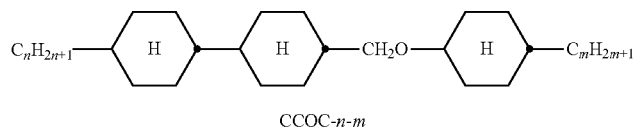
CCOC-n-m
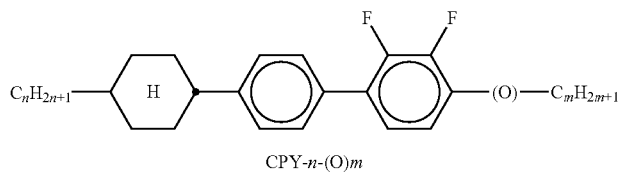
CPY-n-(O)m
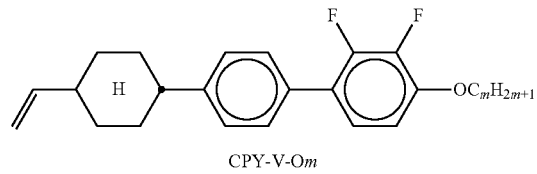
CPY-V-Om
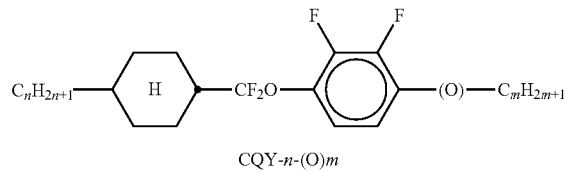
CQY-n-(O)m
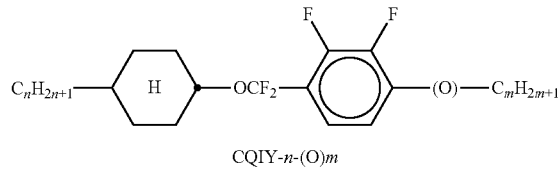
CQIY-n-(O)m TABLE A-continued
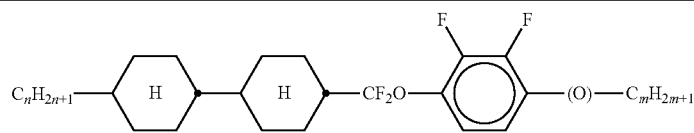
CCQY-n-(O)m
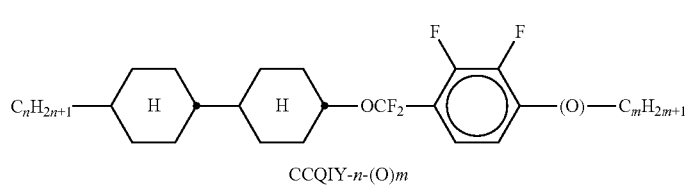
CCQIY-n-(O)m
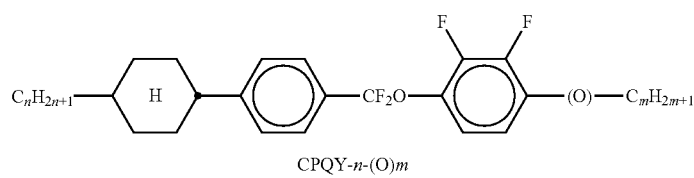
CPQY-n-(O)m
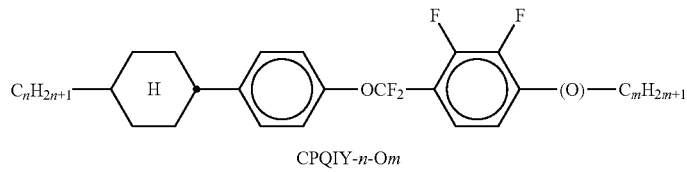
CPQIY-n-Om
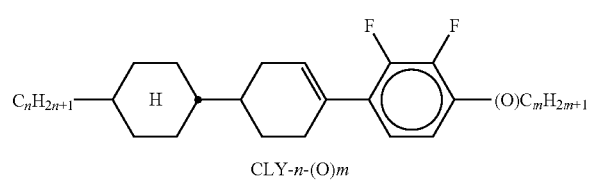
CLY-n-(O)m
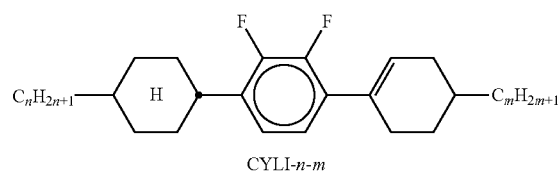
CYLI-n-m
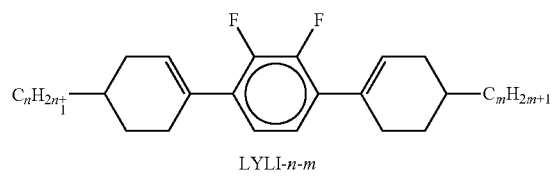
LYLI-n-m
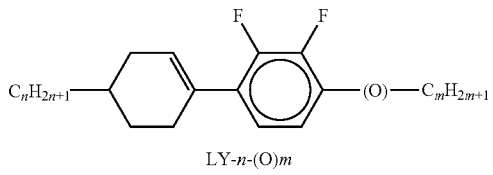
LY-n-(O)m
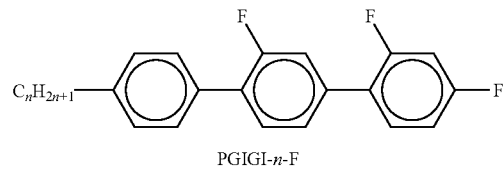
PGIGI-n-F TABLE A-continued
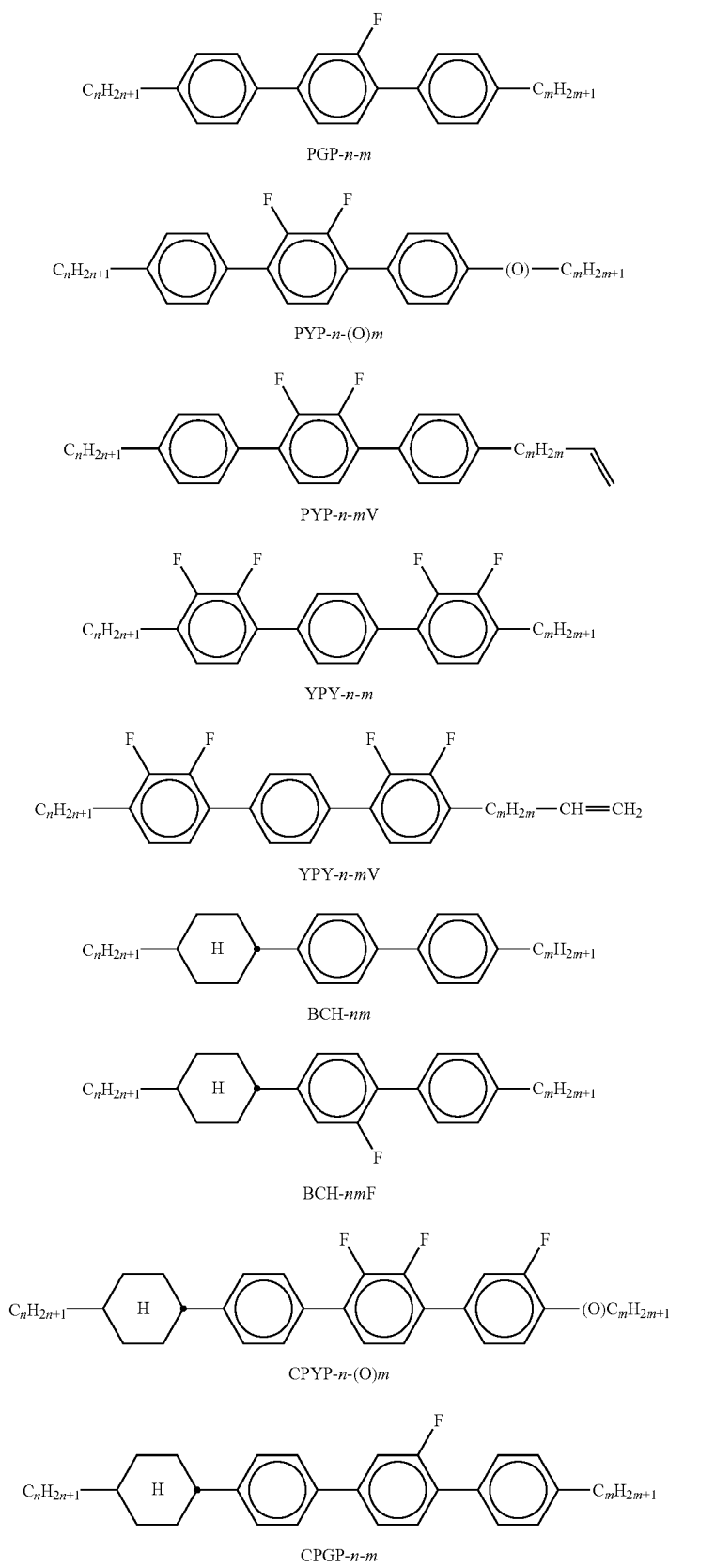

TABLE A-continued
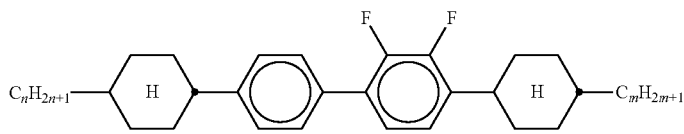
CPYC-n-m
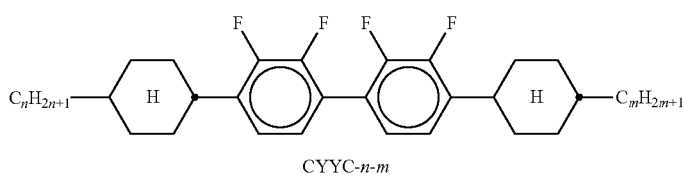
CYYC-n-m
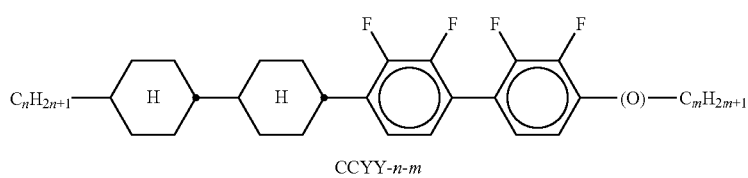
CCYY-n-m
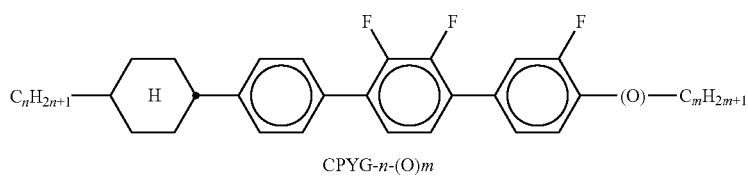
CPYG-n-(O)m
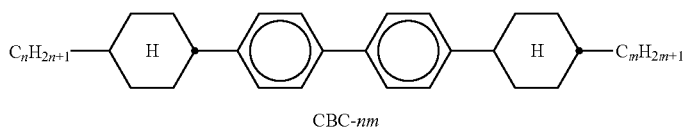
CBC-nm
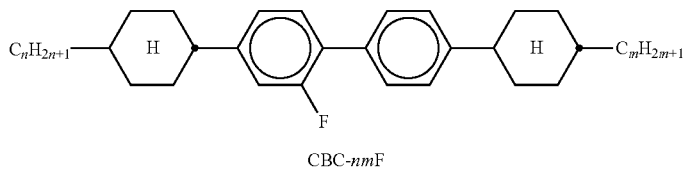
CBC-nmF
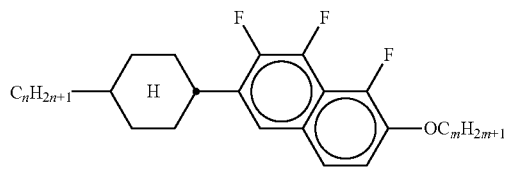
CNap-n-Om
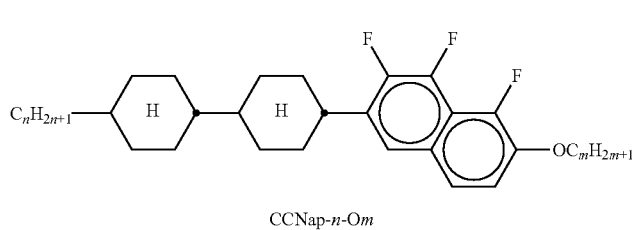
CCNap-n-Om TABLE A-continued

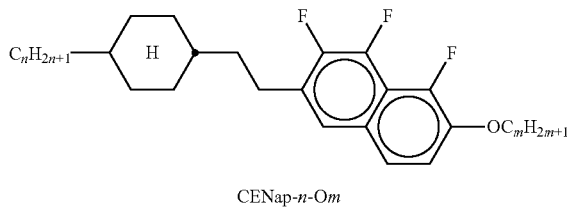

CENap-*n*-O*m*

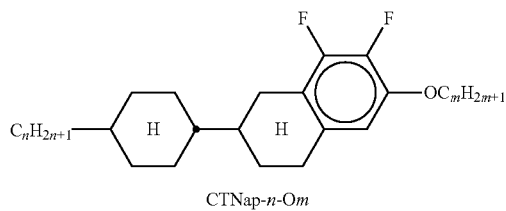

CTNap-*n*-O*m*

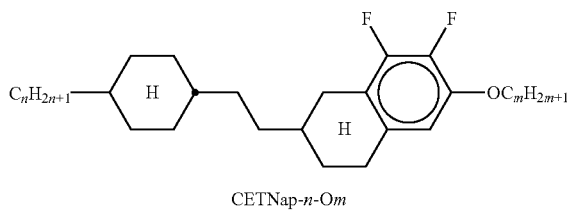

CETNap-*n*-O*m*

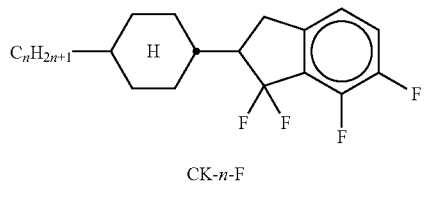

CK-*n*-F

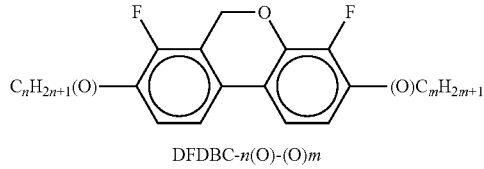

DFDBC-*n*(O)-(O)*m*

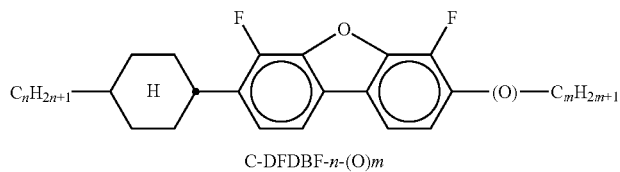

C-DFDBF-*n*-(O)*m*

In a preferred embodiment of the present invention, the LC media according to the invention comprise one or more compounds selected from the group consisting of compounds from Table A.

TABLE B

Table B shows possible chiral dopants which can be added to the LC media according to the invention.

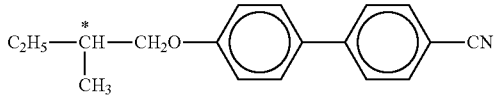

C 15

TABLE B-continued
Table B shows possible chiral dopants which can be added to the LC media according to the invention.
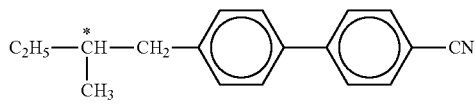
CB 15
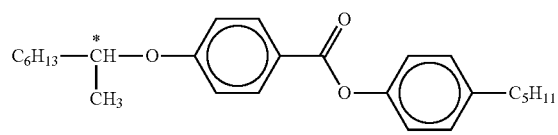
CM 21
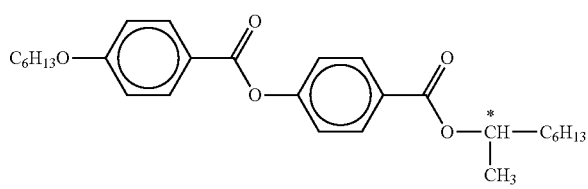
R/S-811
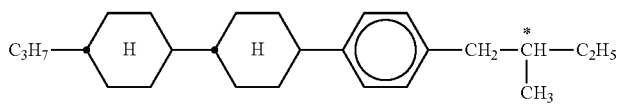
CM 44
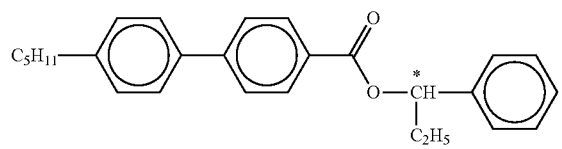
CM 45
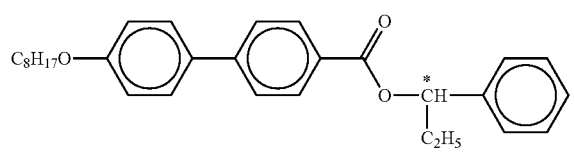
CM 47
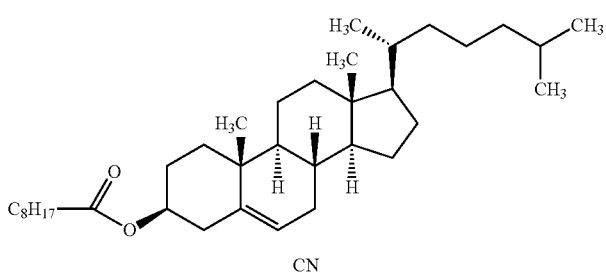
CN
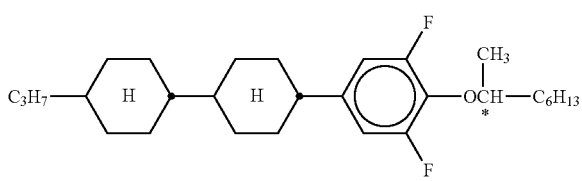
R/S-2011

TABLE B-continued

Table B shows possible chiral dopants which can be added to the LC media according to the invention.

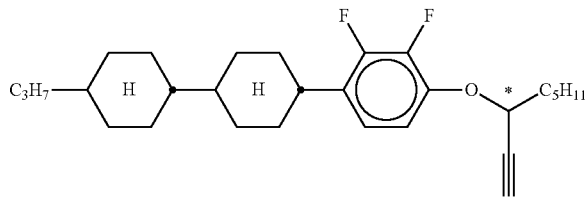

R/S-3011

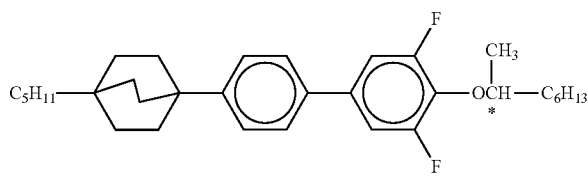

R/S-4011

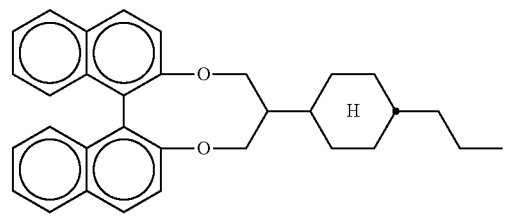

R/S-5011

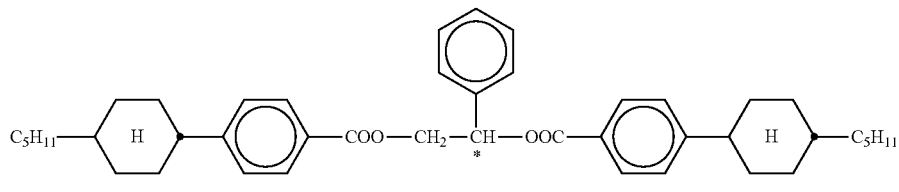

R/S-1011

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

Table C shows possible stabilisers which can be added to the LC media according to the invention.

($n$ here denotes an integer from 1 to 12, preferably 1, 2, 3, 4, 5, 6, 7 or 8, terminal methyl groups are not shown).

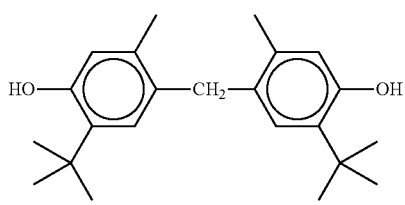

TABLE C-continued
Table C shows possible stabilisers which can be added to the LC media according to the invention. (*n* here denotes an integer from 1 to 12, preferably 1, 2, 3, 4, 5, 6, 7 or 8, terminal methyl groups are not shown).
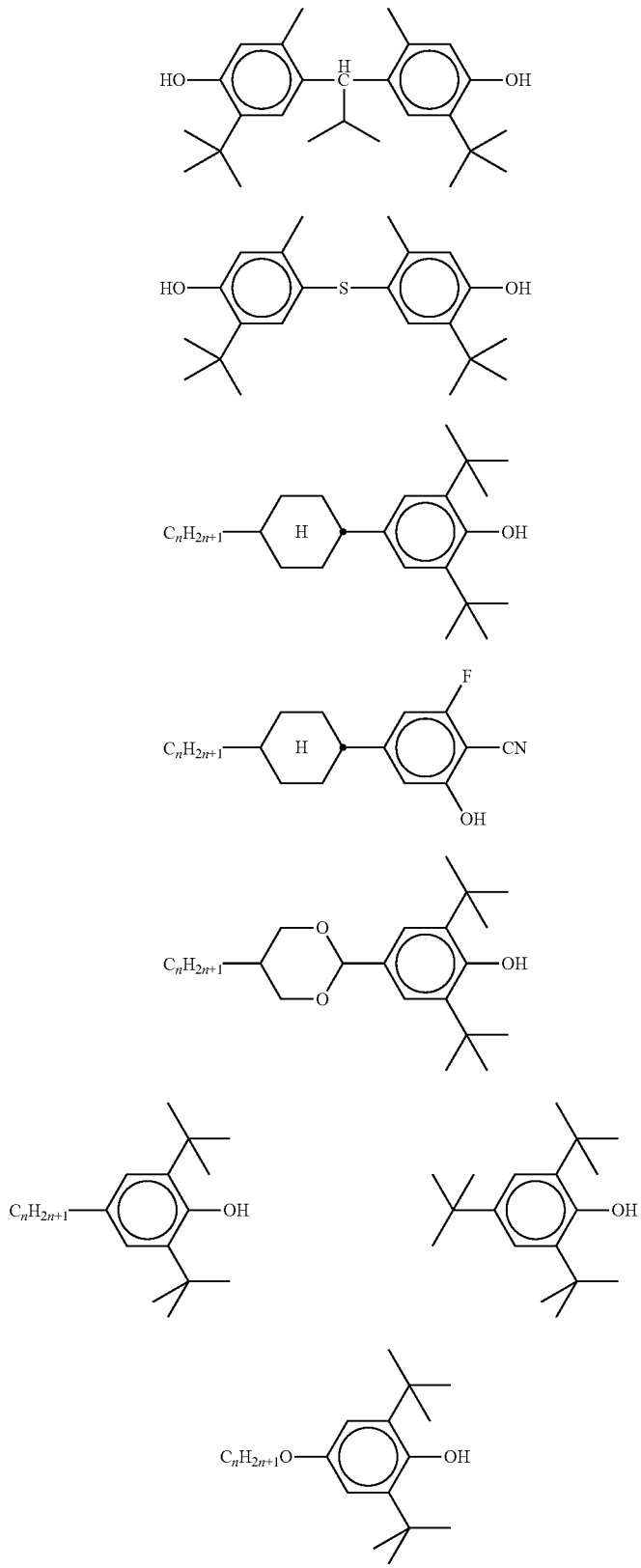

TABLE C-continued
Table C shows possible stabilisers which can be added to the LC media according to the invention. (*n* here denotes an integer from 1 to 12, preferably 1, 2, 3, 4, 5, 6, 7 or 8, terminal methyl groups are not shown).
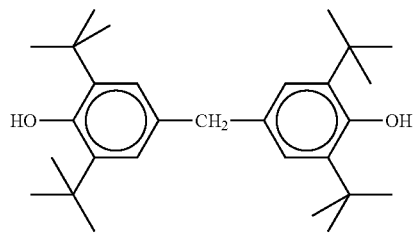
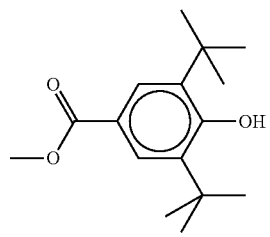
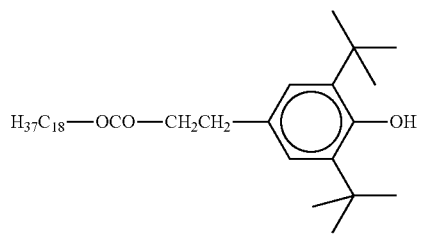
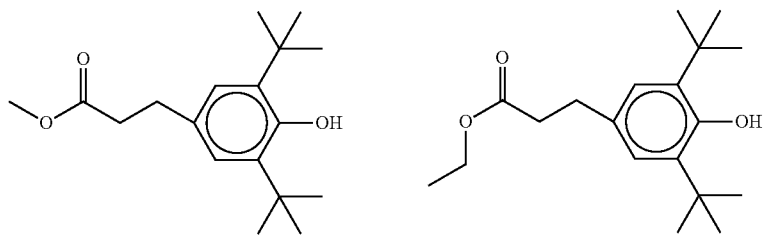
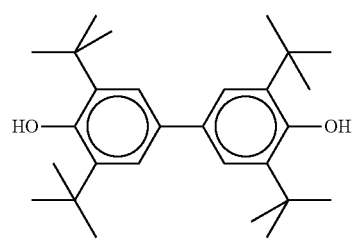

TABLE C-continued
Table C shows possible stabilisers which can be added to the LC media according to the invention.
(*n* here denotes an integer from 1 to 12, preferably 1, 2, 3, 4, 5, 6, 7 or 8, terminal methyl groups are not shown).
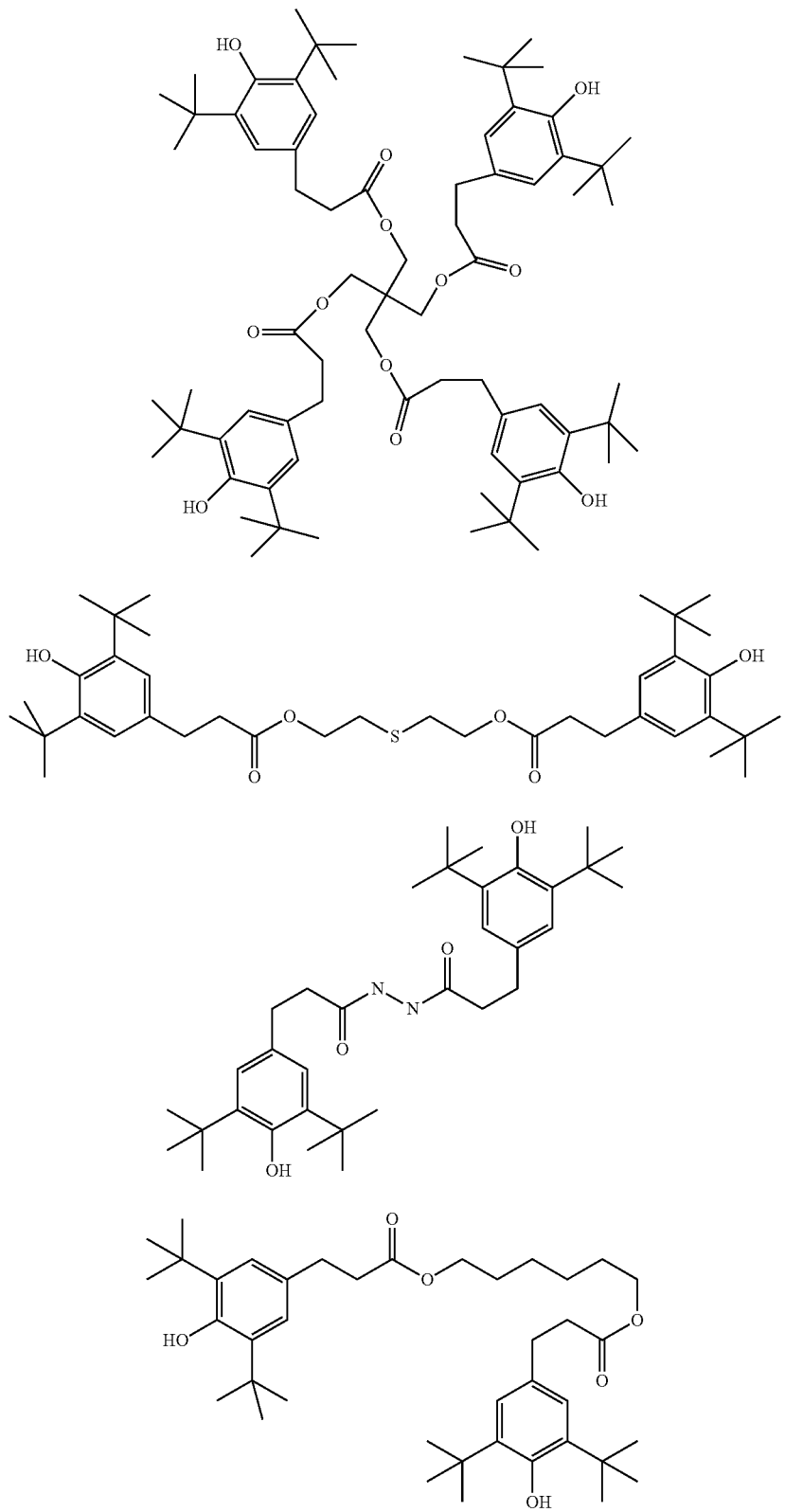

TABLE C-continued
Table C shows possible stabilisers which can be added to the LC media according to the invention.
(*n* here denotes an integer from 1 to 12, preferably 1, 2, 3, 4, 5, 6, 7 or 8, terminal methyl groups are not shown).
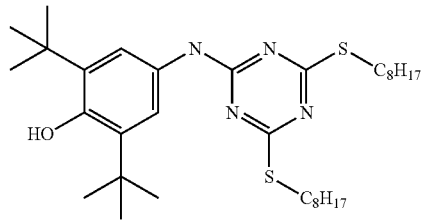
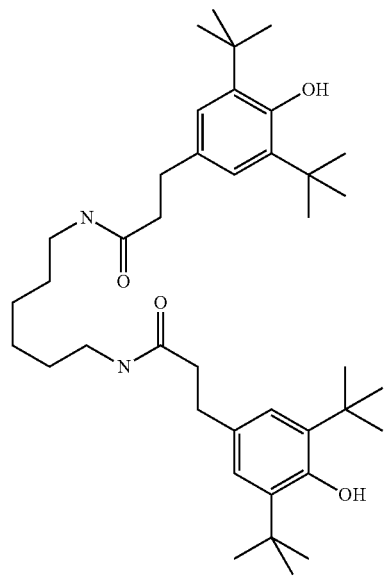 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
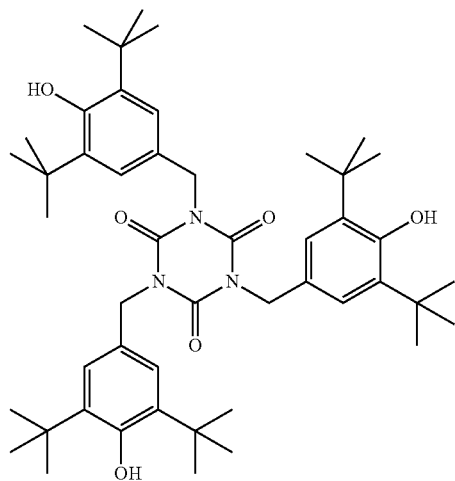 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE C-continued
Table C shows possible stabilisers which can be added to the LC media according to the invention.
(*n* here denotes an integer from 1 to 12, preferably 1, 2, 3, 4, 5, 6, 7 or 8, terminal methyl groups are not shown).
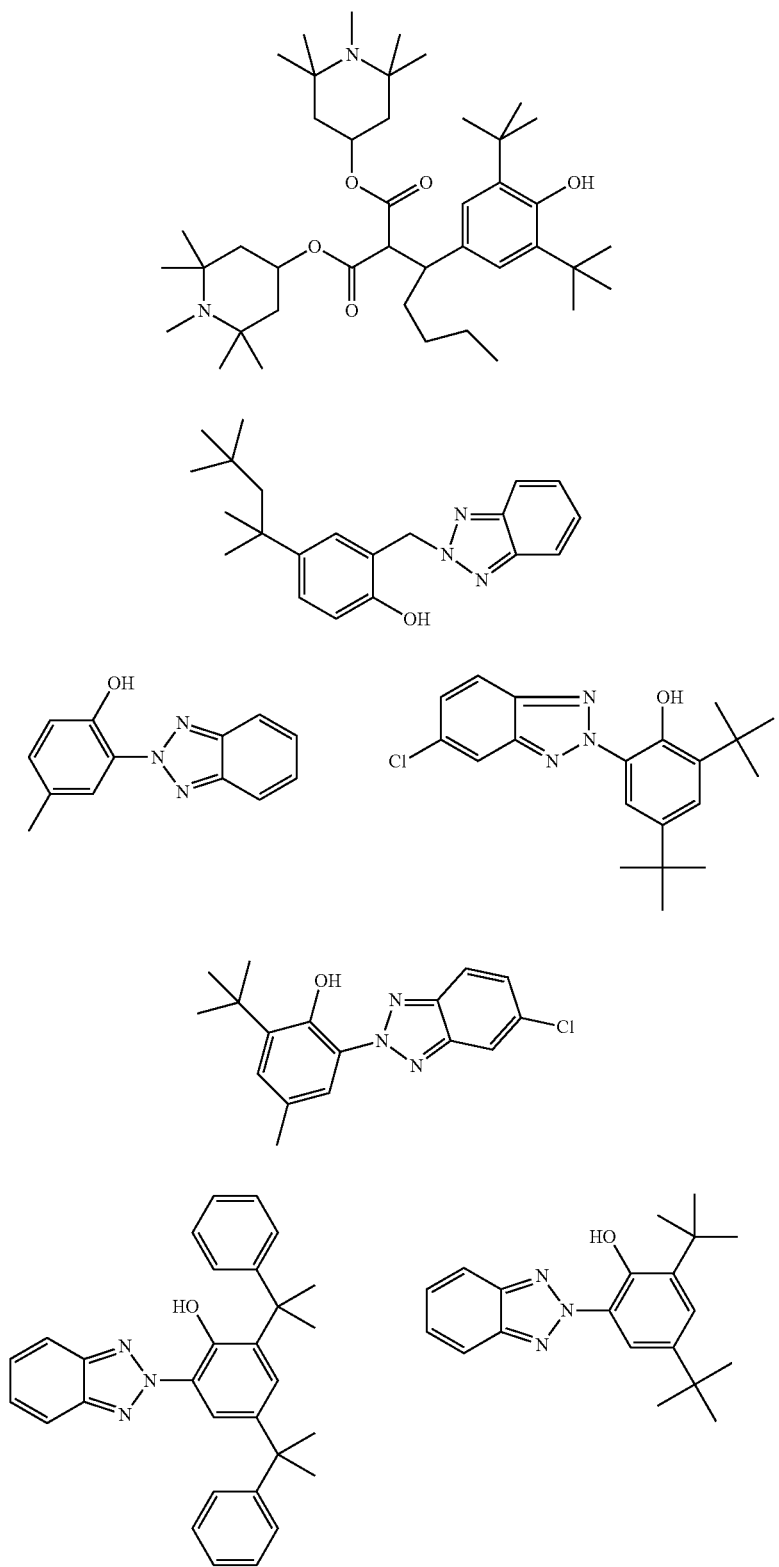

TABLE C-continued
Table C shows possible stabilisers which can be added to the LC media according to the invention.
(*n* here denotes an integer from 1 to 12, preferably 1, 2, 3, 4, 5, 6, 7 or 8, terminal methyl groups are not shown).
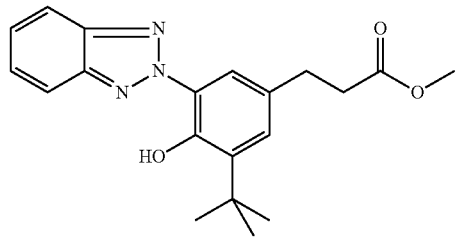 [SMILES: COC(=O)CCc1cc(-n2nc3ccccc3n2)c(O)c(C(C)(C)C)c1]
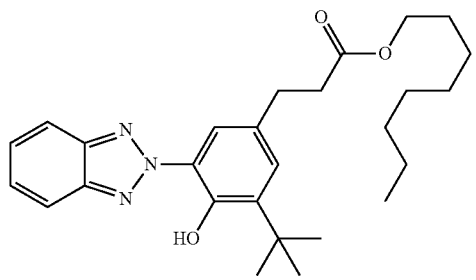 [SMILES: CCCCCCCCOC(=O)CCc1cc(-n2nc3ccccc3n2)c(O)c(C(C)(C)C)c1]
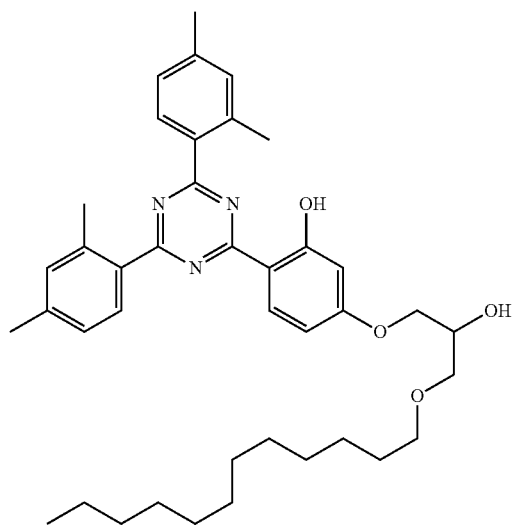 [SMILES: CCCCCCCCCCCCOCC(O)COc1ccc(-c2nc(-c3ccc(C)cc3C)nc(-c3ccc(C)cc3C)n2)c(O)c1]
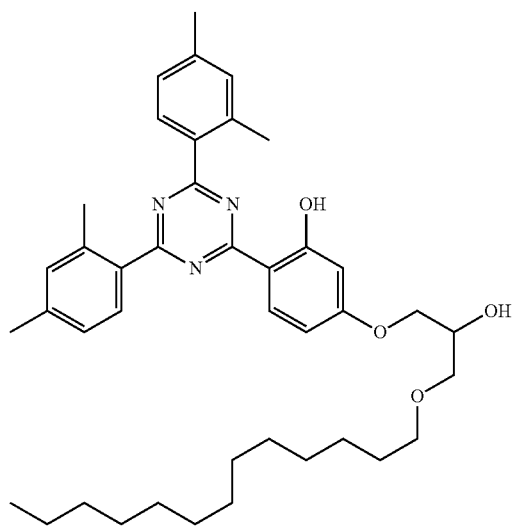 [SMILES: CCCCCCCCCCCCCOCC(O)COc1ccc(-c2nc(-c3ccc(C)cc3C)nc(-c3ccc(C)cc3C)n2)c(O)c1]

TABLE C-continued

Table C shows possible stabilisers which can be added to the LC media according to the invention.
(*n* here denotes an integer from 1 to 12, preferably 1, 2, 3, 4, 5, 6, 7 or 8, terminal methyl groups are not shown).

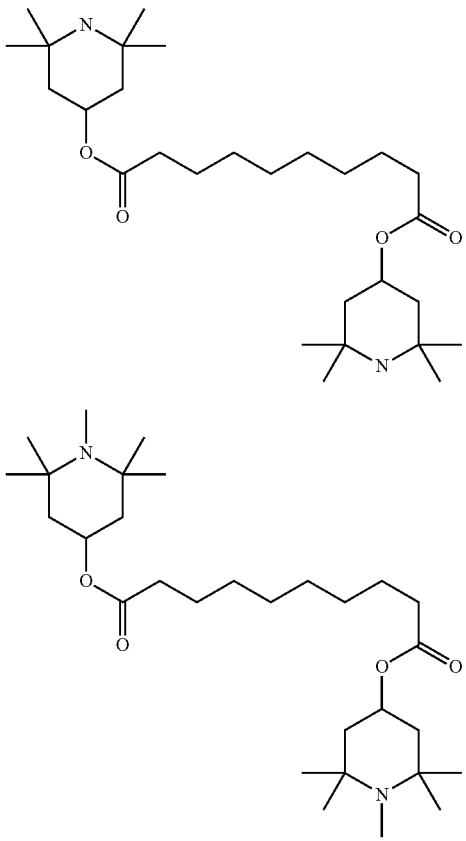

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

Table D shows illustrative compounds which can be used in the LC media in accordance with the present invention, preferably as reactive mesogenic compounds.

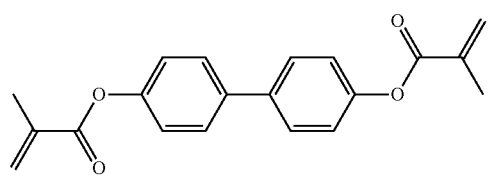 [SMILES: C=C(C)C(=O)Oc1ccc(-c2ccc(OC(=O)C(=C)C)cc2)cc1]

RM-1

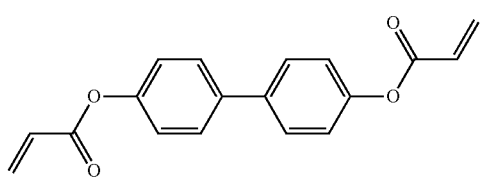 [SMILES: C=CC(=O)Oc1ccc(-c2ccc(OC(=O)C=C)cc2)cc1]

RM-2

TABLE D-continued
Table D shows illustrative compounds which can be used in the LC media in accordance with the present invention, preferably as reactive mesogenic compounds.
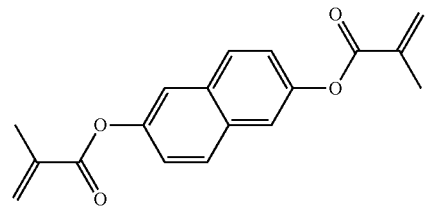 [SMILES: C=C(C)C(=O)Oc1ccc2cc(OC(=O)C(=C)C)ccc2c1]
RM-3
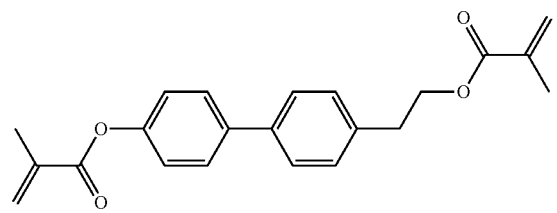 [SMILES: C=C(C)C(=O)OCCc1ccc(-c2ccc(OC(=O)C(=C)C)cc2)cc1]
RM-4
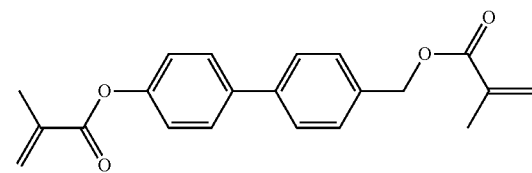 [SMILES: C=C(C)C(=O)OCc1ccc(-c2ccc(OC(=O)C(=C)C)cc2)cc1]
RM-5
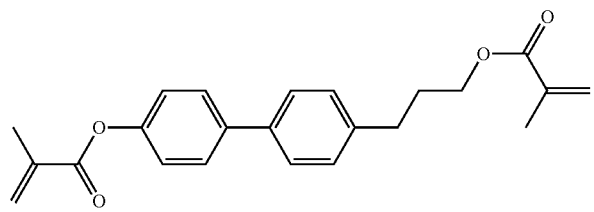 [SMILES: C=C(C)C(=O)OCCCc1ccc(-c2ccc(OC(=O)C(=C)C)cc2)cc1]
RM-6
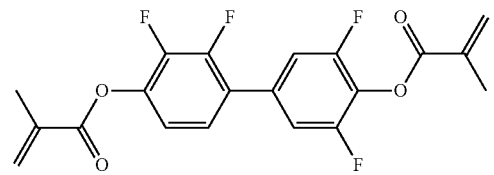 [SMILES: C=C(C)C(=O)Oc1ccc(-c2cc(F)c(OC(=O)C(=C)C)c(F)c2)c(F)c1F]
RM-7
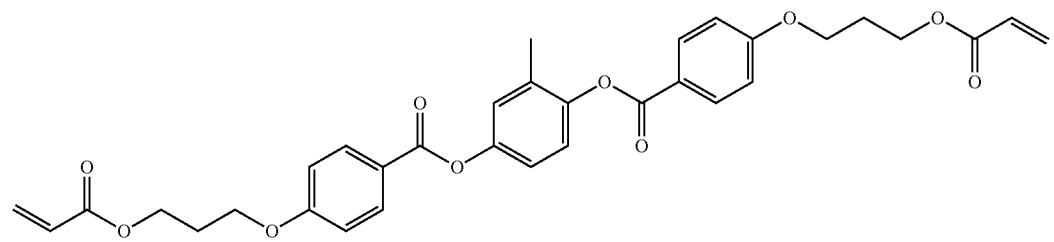 [SMILES: C=CC(=O)OCCCOc1ccc(C(=O)Oc2ccc(OC(=O)c3ccc(OCCCOC(=O)C=C)cc3)c(C)c2)cc1]
RM-8
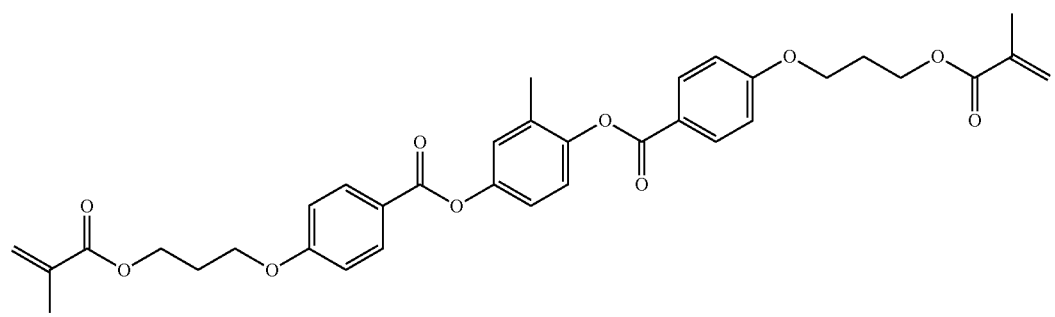 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-9

TABLE D-continued
Table D shows illustrative compounds which can be used in the LC media in accordance with the present invention, preferably as reactive mesogenic compounds.
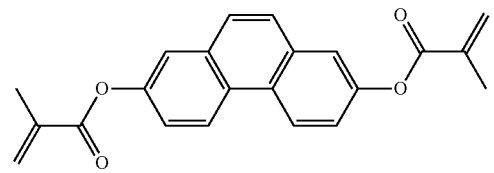 [SMILES: C=C(C)C(=O)Oc1ccc2c(ccc3cc(OC(=O)C(=C)C)ccc32)c1]
RM-10
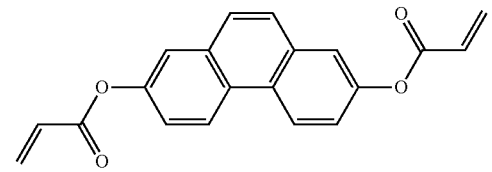 [SMILES: C=CC(=O)Oc1ccc2c(ccc3cc(OC(=O)C=C)ccc32)c1]
RM-11
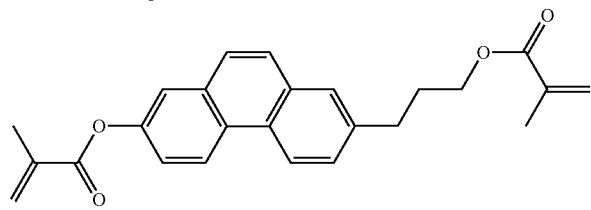
RM-12
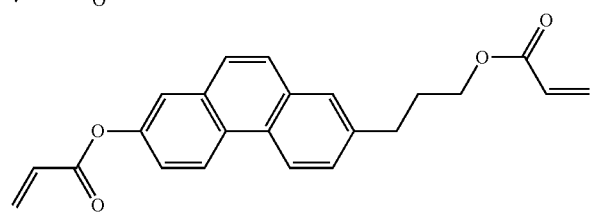
RM-13
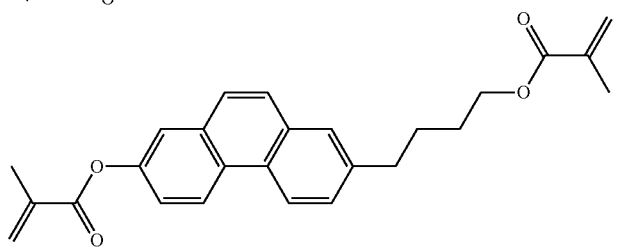
RM-14
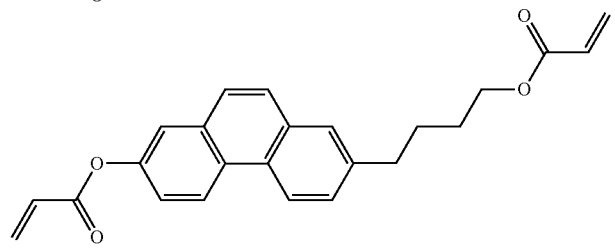
RM-15
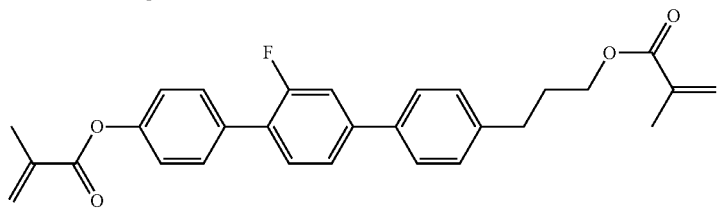 [SMILES: C=C(C)C(=O)OCCCc1ccc(-c2ccc(-c3ccc(OC(=O)C(=C)C)cc3)c(F)c2)cc1]
RM-16
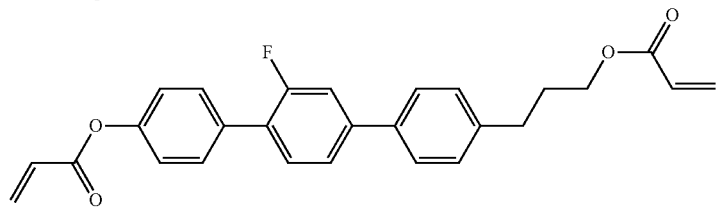 [SMILES: C=CC(=O)OCCCc1ccc(-c2ccc(-c3ccc(OC(=O)C=C)cc3)c(F)c2)cc1]
RM-17

TABLE D-continued
Table D shows illustrative compounds which can be used in the LC media in accordance with the present invention, preferably as reactive mesogenic compounds.
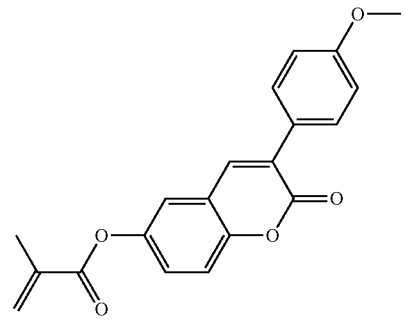 [SMILES: C=C(C)C(=O)Oc1ccc2oc(=O)c(-c3ccc(OC)cc3)cc2c1]
RM-18
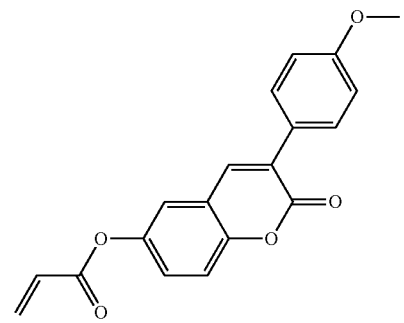 [SMILES: C=CC(=O)Oc1ccc2oc(=O)c(-c3ccc(OC)cc3)cc2c1]
RM-19
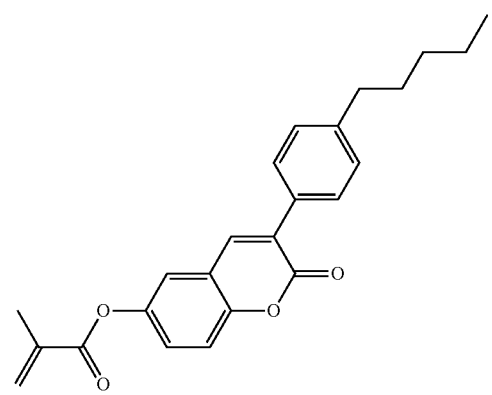 [SMILES: C=C(C)C(=O)Oc1ccc2oc(=O)c(-c3ccc(CCCCC)cc3)cc2c1]
RM-20
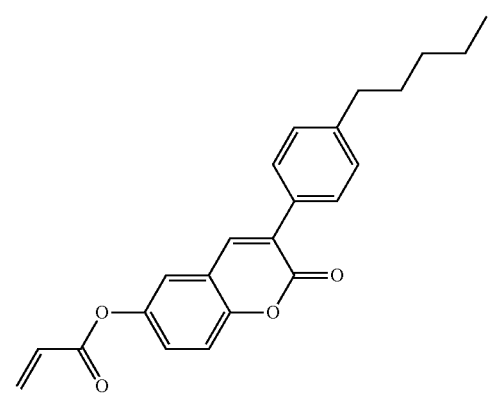 [SMILES: C=CC(=O)Oc1ccc2oc(=O)c(-c3ccc(CCCCC)cc3)cc2c1]
RM-21

TABLE D-continued
Table D shows illustrative compounds which can be used in the LC media in accordance with the present invention, preferably as reactive mesogenic compounds.
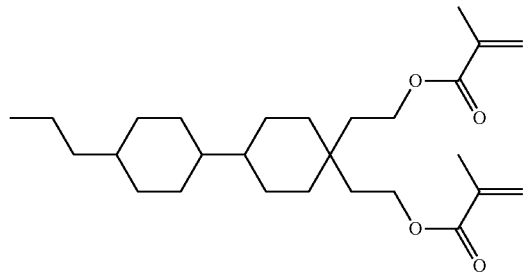 [SMILES: C=C(C)C(=O)OCCC1(CCOC(=O)C(=C)C)CCC(C2CCC(CCC)CC2)CC1]
RM-22
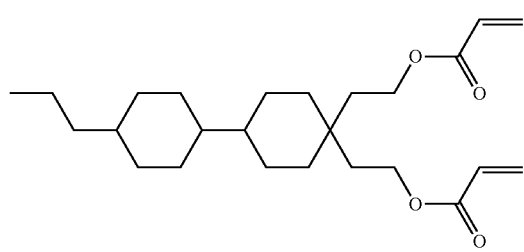 [SMILES: C=CC(=O)OCCC1(CCOC(=O)C=C)CCC(C2CCC(CCC)CC2)CC1]
RM-23
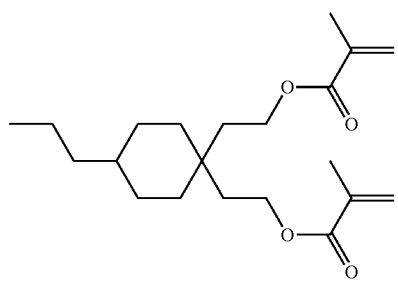 [SMILES: C=C(C)C(=O)OCCC1(CCOC(=O)C(=C)C)CCC(CCC)CC1]
RM-24
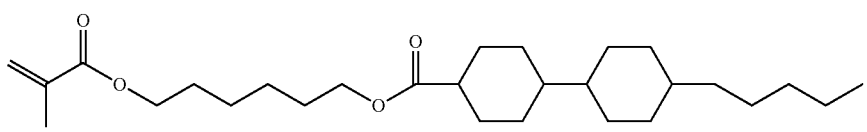 [SMILES: C=C(C)C(=O)OCCCCCCOC(=O)C1CCC(C2CCC(CCCCC)CC2)CC1]
RM-25
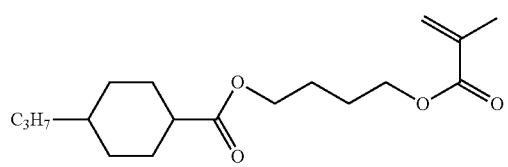
RM-26
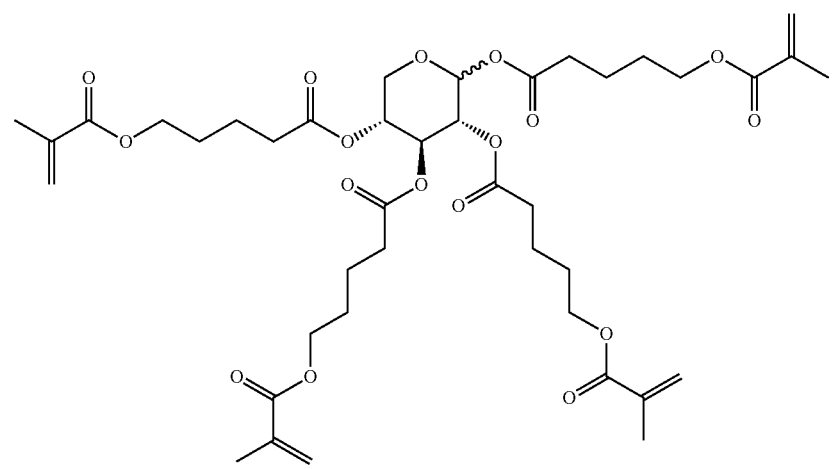 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-27

TABLE D-continued

Table D shows illustrative compounds which can be used in the LC media in accordance with the present invention, preferably as reactive mesogenic compounds.

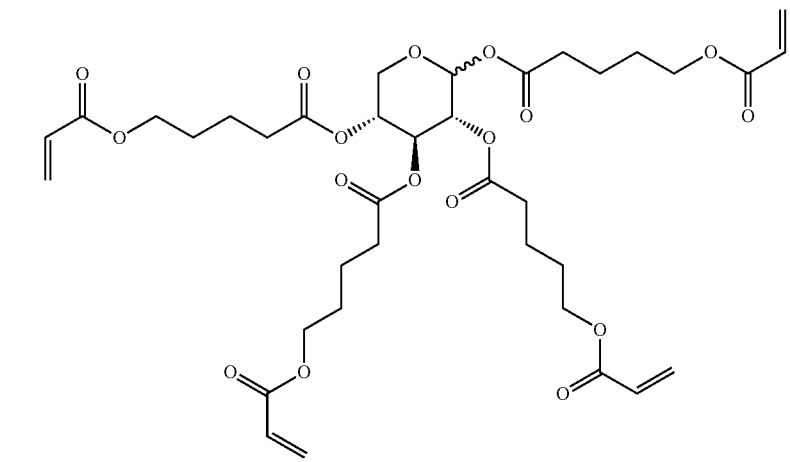 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]

RM-28

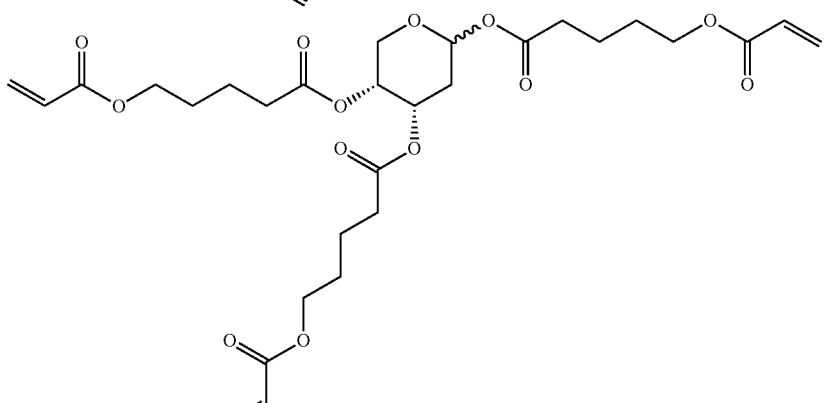

RM-29

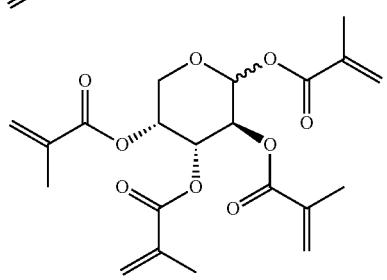

RM-30

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
Δn optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
Δ$\epsilon$ dielectric anisotropy at 20° C. and 1 kHz,
cl.p., T(N,I) clearing point [C],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δ∈ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

The display used for measurement of the capacitive threshold voltage consists of two plane-parallel glass outer plates at a separation of 20 μm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light (usually 365 nm) of defined intensity for a prespecified time, with a voltage simultaneously being applied to the display (usually 10 V to 30 V alternating current, 1 kHz). In the examples, unless indicated otherwise, a 28 mW/cm² mercury vapour lamp is used, and the intensity is measured using a standard UV meter (model Ushio UNI meter) fitted with a 365 nm band-pass filter.

The tilt angle is determined by rotational crystal experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into TN-VHR test cells (rubbed at 90°, TN-polyimide alignment layer, layer thickness d≈4 μm). The HR value is determined after 5 min at 100° C. before and after UV exposure for 2 h (sun test) at 1 V, 60 Hz, 64 μs pulse (measuring instrument: Autronic-Melchers VHRM-105).

Example 1

7-(2-Methylacryloyloxy)-9,10-dihydrophenanthren-2-yl 2-methylacrylate

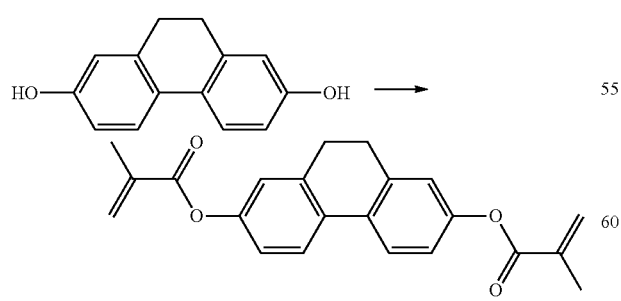

7.50 g (35.3 mmol) of 9,10-dihydrophenanthrene-2,7-diol (CAS No. 99896-39-6) are initially introduced in 100 ml of dichloromethane, 15 ml of pyridine are added, and a solution of 13.0 g (0.124 mol) of methacryloyl chloride in 100 ml of dichloromethane is added dropwise with ice cooling.

The cooling is removed, and the batch is left to stir overnight at room temp. The deposited precipitate is filtered off, the filtrate is evaporated in vacuo, and the residue is filtered through silica gel with dichloromethane. Crystallisation from heptane/toluene gives 7-(2-methylacryloyloxy)-9,10-dihydrophenanthren-2-yl 2-methylacrylate as colourless solid of m.p. 116° C.

Example 2

4,7-Difluoro-8-(2-methylacryloyloxy)-6H-benzo[c]chromen-3-yl 2-methylacrylate 2.1 4,7-Difluoro-6H-benzo[c]chromene-3,8-diol

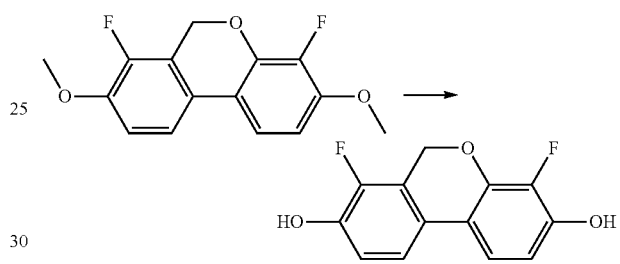

5.23 g (18.8 mmol) of 4,7-difluoro-3,8-dimethoxy-6H-benzo[c]chromene (prepared by the method of: Taugerbeck, Klasen-Memmer, WO 2004076438) are initially introduced in 70 ml of dichloromethane, and a solution of 5 ml (52.7 mmol) of boron tribromide in 10 ml of dichloromethane is added dropwise with ice cooling. After 1 h, the cooling is removed, and the batch is left to stir at room temp. for 3 h and added to ice-cold 1 M sodium hydroxide solution. The aqueous phase is separated off and extracted three times with ethyl acetate. The combined org. phases are washed with sat. sodium chloride soln. and dried over sodium sulfate. The solvent is removed in vacuo, the residue is filtered through silica gel with toluene/ethyl acetate (3:2), and the crude product is washed by stirring with hot heptane/ethyl acetate (2:1) and filtered off with suction after cooling to 8° C., giving 4,7-difluoro-6H-benzo[c]chromene-3,8-diol as colourless solid.

¹H-NMR (300 MHz, DMSO-d₆)

δ=5.23 ppm (s, 2 H, CH₂O), 6.62 (t, J=8.4 Hz, 1 H, Ar—H), 6.95 (t, J=8.8 Hz, 1 H, Ar—H), 7.36 (d, J=8.4 Hz, 1 H, Ar—H), 7.36 (d, J=8.8 Hz, 1 H, Ar—H), 10.0 (s, 2 H, Ar—OH).

2.2 4,7-Difluoro-8-(2-methylacryloyloxy)-6H-benzo[c]chromen-3-yl 2-methylacrylate

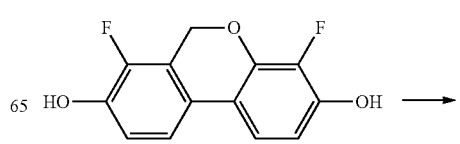

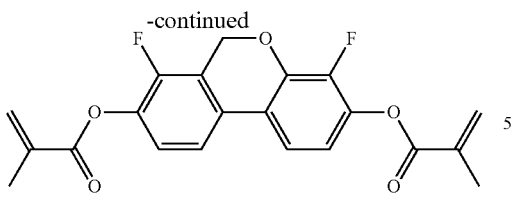

An analogous procedure to Example 1 starting from 4,7-difluoro-6H-benzo[c]chromene-3,8-diol gives 4,7-difluoro-8-(2-methylacryloyloxy)-6H-benzo[c]chromen-3-yl 2-methylacrylate as colourless solid of m.p. 202° C.

Example 3

2-Bromo-7-iodo-9,10-dihydrophenanthrene 3.1 2-Iodo-9,10-dihydrophenanthrene

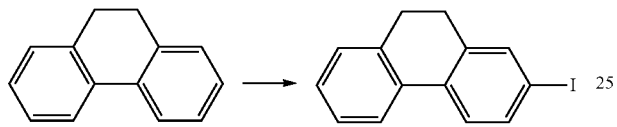

25.0 g (0.139 mol) of 9,10-dihydrophenanthrene, 6.30 g (27.6 mmol) of periodic acid and 17.0 g (67.0 mmol) of iodine are heated at 70° C. for 1 h in a solution of 4 ml of conc. sulfuric acid and 28 ml of water in 140 ml of glacial acetic acid. The solution is subsequently added to ice-water and extracted three times with ethyl acetate. The combined org. phases are washed with sat. sodium hydrogencarbonate soln. and dried over sodium sulfate. The solvent is removed in vacuo, and the residue is distilled in a bulb tube at 170° C. and 0.3 mbar, giving 2-iodo-9,10-dihydrophenanthrene as yellow oil.

$^1$H-NMR (400 MHz, CDCl$_3$)

δ=2.83 ppm (m$_c$, 4 H, —CH$_2$CH$_2$—), 7.20-7.32 (m, 3 H), 7.46 (d, J=8.2 Hz, 1 H), 7.59 (d, J=1.9 Hz, 1 H), 7.62 (dd, J=1.9 Hz, J=8.3 Hz, 1 H), 7.70 (d, J=7.8 Hz, 1 H).

MS (EI) m/e (%)=306 (98) [M$^+$], 178 (100) [M$^+$-HI].

3.2 2-Bromo-7-iodo-9,10-dihydrophenanthrene

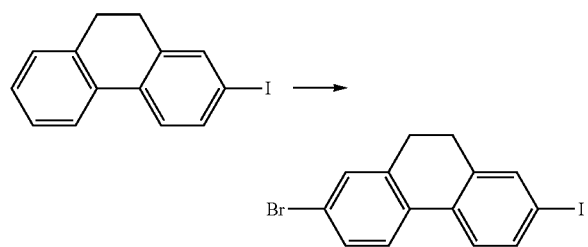

9.5 g (27.9 mmol) of 2-iodo-9,10-dihydrophenanthrene are dissolved in 40 ml of trimethyl phosphate, and a solution of 2 ml (39 mmol) of bromine in 10 ml of trimethyl phosphate is added dropwise at 20° C. After 90 min, the batch is added to ice-water, excess bromine is reduced by addition of sodium hydrogensulfite soln., and the precipitated product is filtered off with suction, taken up in toluene, washed with sat. sodium hydrogen-carbonate soln. and dried over sodium sulfate. The solvent is removed in vacuo, and the residue is recrystallised from heptane/toluene, giving 2-bromo-7-iodo-9,10-dihydrophenanthrene as colourless crystals.

$^1$H-NMR (400 MHz, CDCl$_3$)

δ=2.81 ppm (s, 4 H, —CH$_2$CH$_2$—), 7.37 (d, J=2.0 Hz, 1 H, Ar—H), 7.40 (d, J=2.0 Hz, 1 H, Ar—H), 7.43 (d, J=1.9 Hz, 1 H, Ar—H), 7.55 (d, J=8.2 Hz, 1 H, Ar—H), 7.59 (d, J=1.7 Hz, 1 H, Ar—H), 7.62 (dd, J=1.9 Hz, J=8.2 Hz, 1 H, Ar—H).

MS (EI) m/e (%)=384 (83) [M$^+$], 178 (100) [M$^+$-HI-HBr].

Example 4

7-[4-(2-Methylacryloyloxy)butyl]-9,10-dihydrophenanthren-2-yl 2-methylacrylate

Suitable precursors are 2,7-diiodo-9,10-dihydrophenanthrene (see Cho et al., Chemistry of Materials (2008), 20(20), 6289-6291), 2,7-dibromo-9,10-dihydrophenanthrene (see D. E. Pearson, Synthesis 1976, 621-623) or 2-bromo-7-iodo-9,10-dihydrophenanthrene.

4.1 7-Iodo-9,10-dihydrophenanthren-2-ol

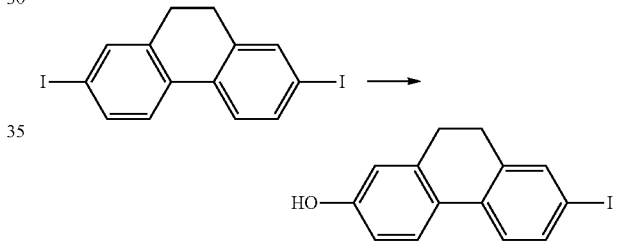

8.8 g (20.4 mmol) of 2,7-diiodo-9,10-dihydrophenanthrene are dissolved in 250 ml of THF, and, after addition of 7.0 ml (30.5 mmol) of triisopropyl borate, 16.5 ml of a 15 percent soln. of n-butyllithium in hexane are added at −70° C. After 1 h, the batch is hydrolysed using 2 N hydrochloric acid and warmed to room temperature. The solution is extracted twice with MTB ether, dried over sodium sulfate, the solvent is removed in vacuo, and the resultant crude product is suspended in 80 ml of toluene and 30 ml of 2 N sodium hydroxide solution with vigorous stirring. After addition of 8 ml of 30% hydrogen peroxide, the batch is stirred at 30-40° C. for 30 min with gentle cooling, 200 ml of water are added, and the mixture is acidified using 2 N hydrochloric acid. The aqueous phase is separated off and extracted three times with ethyl acetate. The combined org. phases are washed with dil. ammonium iron(II) sulfate soln. and dried over sodium sulfate. The solvent is removed in vacuo, and the residue is filtered through silica gel with dichloromethane, giving 7-iodo-9,10-dihydrophenanthren-2-ol as colourless solid.

$^1$H-NMR (400 MHz, DMSO-d$_6$)

δ=2.72 ppm (m$_c$, 4 H, —CH$_2$CH$_2$—), 6.66 (6, J=2.4 Hz, 1 H, Ar—H), 6.70 (dd, J=2.4 Hz, J=8.5 Hz, 1 H, Ar—H), 7.47 (d, J=8.0 Hz, 1 H, Ar—H), 7.60 (m$_c$, 2 H, Ar—H), 9.57 (s, br., 1 H, OH).

4.2 7-(4-Hydroxybut-1-ynyl)-9,10-dihydrophenanthren-2-ol

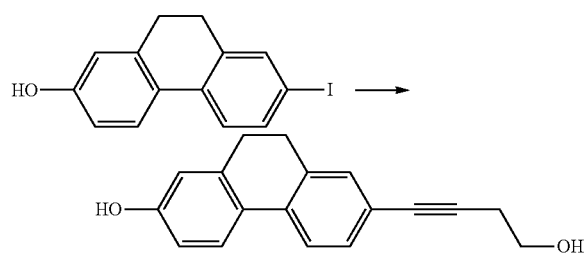

9.0 g (24.6 mmol) of 7-iodo-9,10-dihydrophenanthren-2-ol are initially introduced in 100 ml of THF, 1.0 g (1.43 mmol) of bis(triphenylphosphine)palladium(II) chloride, 0.3 g (1.58 mmol) of copper(I) iodide and 11 ml of diisopropylamine are added, and subsequently a solution of 3.0 g (42.8 mmol) of but-3-yn-1-ol in 20 ml of THF is added dropwise at max. 30° C. with gentle cooling. The batch is left to stir at room temp. for 1.5 h, added to water and acidified using 2 N hydrochloric acid. The aqueous phase is separated off and extracted three times with ethyl acetate. The combined org. phases are washed with water, dried over sodium sulfate, and the solvent is removed in vacuo. The crude product is filtered through silica gel with dichloromethane/ethyl acetate (3:1) and recrystallised from toluene, giving 7-(4-hydroxybut-1-ynyl)-9,10-dihydrophenanthren-2-ol as colourless solid.

4.3 7-(4-Hydroxybutyl)-9,10-dihydrophenanthren-2-ol

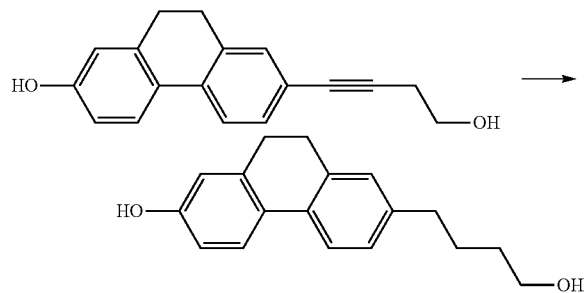

7-(4-Hydroxybut-1-ynyl)-9,10-dihydrophenanthren-2-ol is dissolved in THF and hydrogenated to completion on palladium/active carbon catalyst. The catalyst is filtered off, the solvent is removed in vacuo, and the residue is recrystallised from toluene, giving 7-(4-hydroxybutyl)-9,10-dihydrophenanthren-2-ol as colourless crystals.

4.4 7-[4-(2-Methylacryloyloxy)butyl]-9,10-dihydrophenanthren-2-yl 2-methylacrylate

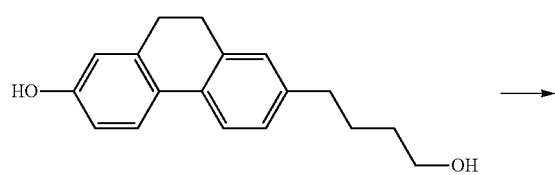

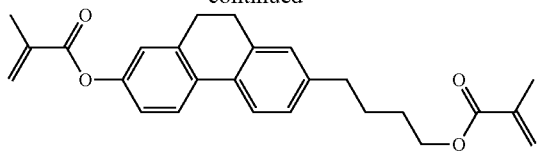

An analogous procedure to Example 1 starting from 7-(4-hydroxybutyl)-9,10-dihydrophenanthren-2-ol gives 7-[4-(2-methylacryloyloxy)butyl]-9,10-dihydrophenanthren-2-yl 2-methylacrylate as colourless oil.

Examples 5-197

The synthesis for the compounds of example (32) is described specifically below.

Example 32

4-[9,9-Dimethyl-7-(2-methylacryloyloxy)-9H-fluoren-2-yl]but-3-ynyl 2-methylacrylate

32.1 7-Bromo-9,9-dimethyl-9H-fluoren-2-ol

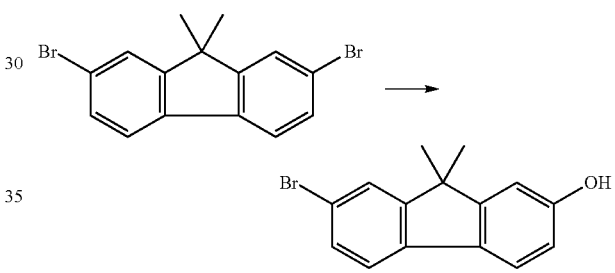

21.2 g (58.6 mmol) of 2,7-dibromo-9,9-dimethyl-9H-fluorene (CAS No. 28320-32-3) and 19.0 ml (82.8 mmol) of triisopropyl borate are dissolved in 500 ml of THF, and 56 ml (89 mmol) of a 15 percent solution of n-butyllithium in n-hexane are added at −70° C. After 2 h, 200 ml of 2 M hydrochloric acid are added, and the batch is allowed to thaw at room temp. and extracted three times with MTB ether. The combined org. phases are dried over sodium sulfate, the solvent is removed in vacuo, and the residue is taken up in 400 ml of toluene. After addition of 85 ml of 2 M sodium hydroxide solution, 15.5 ml of 30 percent hydrogen peroxide are added with vigorous stirring at such a rate that the temp. does not exceed 40° C. When the addition is complete, the batch is stirred for a further 30 min, added to 500 ml of water and acidified using 2 M hydrochloric acid. The aqueous phase is separated off and extracted three times with ethyl acetate. The combined org. phases are washed with dil. ammonium iron(II) sulfate soln. and water, dried over sodium sulfate and evaporated. Filtration of the crude product through silica gel with toluene/ethyl acetate (9:1) gives 7-bromo-9,9-dimethyl-9H-fluoren-2-ol as colourless solid.

$^1$H-NMR (400 MHz, CDCl$_3$)

δ=1.44 ppm (s, 6 H, Me), 4.81 (s, 1 H, OH), 6.79 (dd, J=2.4 Hz, J=8.2 Hz, 1 H, Ar—H), 6.88 (d, J=2.4 Hz, 1 H, Ar—H), 7.41 (AB-dd, J=1.7 Hz, 8.1 Hz, 1 H, Ar—H), 7.46 (AB-d, J=8.1 Hz, 1 H, Ar—H), 7.50 (d, J=1.7 Hz, 1 H, Ar—H), 7.53 (d, J=8.1 Hz, 1 H, Ar—H).

32.2 7-(4-Hydroxybut-1-ynyl)-9,9-dimethyl-9H-fluoren-2-ol

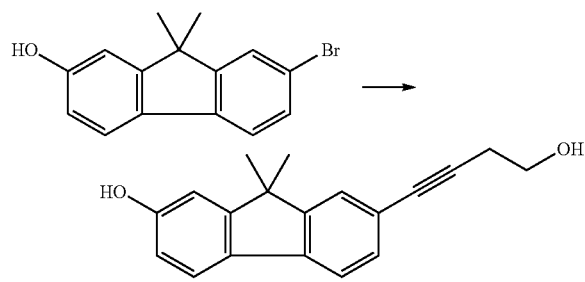

14.7 g (0.048 mol) of 7-bromo-9,9-dimethyl-9H-fluoren-2-ol, 1.3 g (1.85 mmol) of bis(triphenylphosphine)palladium (II) chloride and 0.5 g (2.6 mmol) of copper(I) iodide are initially introduced in 200 ml of THF and 20 ml of diisopropylamine, and a solution of 9.5 ml (0.13 mmol) of but-3-yn-1-ol in 50 ml of THF is added over the course of 2 h under reflux. When the addition is complete, the batch is heated under reflux for a further 1 h, added to water, acidified using dil. hydrochloric acid and extracted three times with ethyl acetate. The combined org. phases are dried over sodium sulfate, and the solvent is removed in vacuo. Chromatography of the crude product on silica gel with toluene/ethyl acetate (4:1) gives 7-(4-hydroxybut-1-ynyl)-9,9-dimethyl-9H-fluoren-2-ol as colourless oil.

$^1$H-NMR (400 MHz, CDCl$_3$): δ=1.44 ppm (s, 6 H, Me), 2.73 (t, J=6.2 Hz, 2 H, C≡CCH$_2$), 3.85 (q, J=6.2 Hz, 2 H, CH$_2$CH$_2$OH), 5.17 (s, 1 H, OH), 6.80 (dd, J=2.4 Hz, J=8.2 Hz, 1 H, Ar—H), 6.89 (d, J=2.4 Hz, 1 H, Ar—H), 7.36 (dd, J=1.4 Hz, J=7.8 Hz, 1 H, Ar—H), 7.44 (d, J=0.8 Hz, 1 H, Ar—H), 7.52 (d, J=7.8 Hz, 1 H, Ar—H), 7.54 (d, J=8.2 Hz, 1 H, Ar—H).

32.3 7-(4-Hydroxybutyl)-9,9-dimethyl-9H-fluoren-2-ol

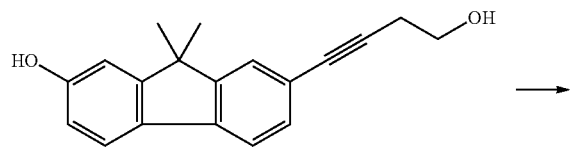

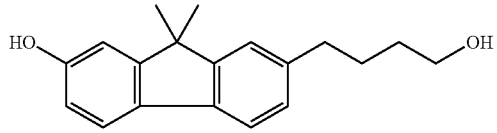

7-(4-Hydroxybut-1-ynyl)-9,9-dimethyl-9H-fluoren-2-ol is hydrogenated to completion in THF on palladium/active carbon. The catalyst is filtered off, the solvent is removed in vacuo, and the residue is employed in the next step without further purification.

$^1$H-NMR (400 MHz, CDCl$_3$): δ=1.39 ppm (s, br. 1 H, OH), 1.43 (s, 6 H, Me), 1.61-1.79 (m, 4 H, CH$_2$), 2.70 (t, J=7.3 Hz, 2 H, Ar—CH$_2$—CH$_2$—), 3.70 (t, J=6.5 Hz, 2 H, —CH$_2$CH$_2$OH), 5.29 (s, 1 H, OH), 6.77 (dd, J=2.4 Hz, J=8.2 Hz, 1 H, Ar—H), 6.88 (d, J=2.4 Hz, 1 H, Ar—H), 7.11 (dd, J=1.5 Hz, J=7.7 Hz, 1 H, Ar—H), 7.19 (d, J=1.1 Hz, 1 H, Ar—H), 7.51 (d, J=7.7 Hz, 1 H, Ar—H), 7.51 (d, J=8.2 Hz, 1 H, Ar—H).

32.4 9,9-Dimethyl-7-[4-(2-methylacryloyloxy)butyl]-9H-fluoren-2-yl 2-methylacrylate

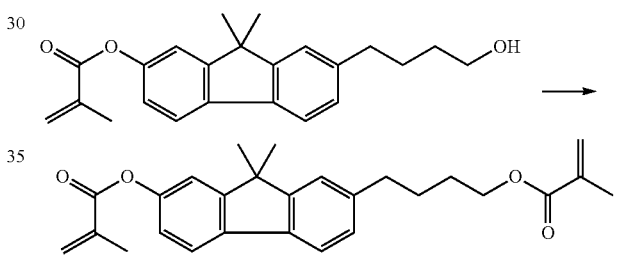

An analogous procedure to Example 1 starting from 7-(4-hydroxybutyl)-9,9-dimethyl-9H-fluoren-2-ol gives 9,9-dimethyl-7-[4-(2-methylacryloyloxy)butyl]-9H-fluoren-2-yl 2-methylacrylate as colourless oil. Glass transition Tg-29 I.

The following compounds are obtained analogously to the processes described in the above examples (Phe=1,4-phenylene):

Compounds of the following formula (Nos. 5-100):

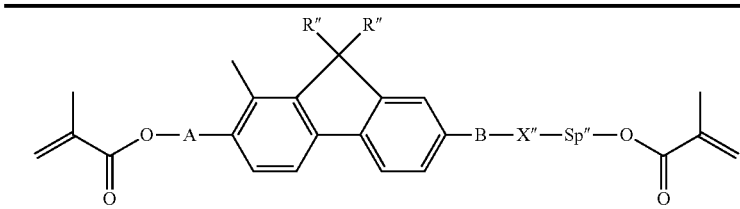

| No. | A | L' | R" | B | X" | Sp" |
|---|---|---|---|---|---|---|
| 5 | — | | H | H | — | — | —CH$_2$— |
| 6 | — | | H | H | — | — | —(CH$_2$)$_2$— |
| 7 | — | | H | H | — | — | —(CH$_2$)$_3$— |
| 8 | — | | H | H | — | — | —(CH$_2$)$_4$— |
| 9 | — | | H | H | — | O | —CH$_2$— |
| 10 | — | | H | H | — | O | —(CH$_2$)$_2$— |

-continued

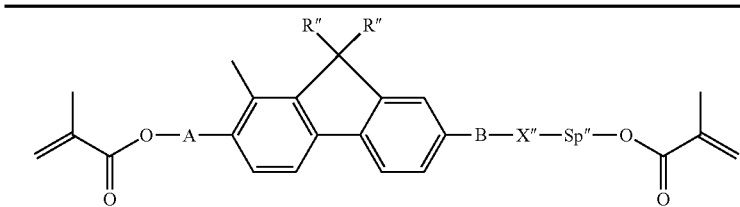

| No. | A | L' | R" | B | X" | Sp" |
|---|---|---|---|---|---|---|
| 11 | — | H | H | — | O | —(CH$_2$)$_3$— |
| 12 | — | H | H | — | O | —(CH$_2$)$_4$— |
| 13 | Phe | H | H | — | — | —CH$_2$— |
| 14 | Phe | H | H | — | — | —(CH$_2$)$_2$— |
| 15 | Phe | H | H | — | — | —(CH$_2$)$_3$— |
| 16 | Phe | H | H | — | — | —(CH$_2$)$_4$— |
| 17 | Phe | H | H | — | O | —CH$_2$— |
| 18 | Phe | H | H | — | O | —(CH$_2$)$_2$— |
| 19 | Phe | H | H | — | O | —(CH$_2$)$_3$— |
| 20 | Phe | H | H | — | O | —(CH$_2$)$_4$— |
| 21 | — | H | H | Phe | — | —CH$_2$— |
| 22 | — | H | H | Phe | — | —(CH$_2$)$_2$— |
| 23 | — | H | H | Phe | — | —(CH$_2$)$_3$— |
| 24 | — | H | H | Phe | — | —(CH$_2$)$_4$— |
| 25 | — | H | H | Phe | O | —CH$_2$— |
| 26 | — | H | H | Phe | O | —(CH$_2$)$_2$— |
| 27 | — | H | H | Phe | O | —(CH$_2$)$_3$— |
| 28 | — | H | H | Phe | O | —(CH$_2$)$_4$— |
| 29 | — | H | CH$_3$ | — | — | —CH$_2$— |
| 30 | — | H | CH$_3$ | — | — | —(CH$_2$)$_2$— |
| 31 | — | H | CH$_3$ | — | — | —(CH$_2$)$_3$— |
| 32 | — | H | CH$_3$ | — | — | —(CH$_2$)$_4$— |
| 33 | — | H | CH$_3$ | — | O | —CH$_2$— |
| 34 | — | H | CH$_3$ | — | O | —(CH$_2$)$_2$— |
| 35 | — | H | CH$_3$ | — | O | —(CH$_2$)$_3$— |
| 36 | — | H | CH$_3$ | — | O | —(CH$_2$)$_4$— |
| 37 | Phe | H | CH$_3$ | — | — | —CH$_2$— |
| 38 | Phe | H | CH$_3$ | — | — | —(CH$_2$)$_2$— |
| 39 | Phe | H | CH$_3$ | — | — | —(CH$_2$)$_3$— |
| 40 | Phe | H | CH$_3$ | — | — | —(CH$_2$)$_4$— |
| 41 | Phe | H | CH$_3$ | — | O | —CH$_2$— |
| 42 | Phe | H | CH$_3$ | — | O | —(CH$_2$)$_2$— |
| 43 | Phe | H | CH$_3$ | — | O | —(CH$_2$)$_3$— |
| 44 | Phe | H | CH$_3$ | — | O | —(CH$_2$)$_4$— |
| 45 | — | H | CH$_3$ | Phe | — | —CH$_2$— |
| 46 | — | H | CH$_3$ | Phe | — | —(CH$_2$)$_2$— |
| 47 | — | H | CH$_3$ | Phe | — | —(CH$_2$)$_3$— |
| 48 | — | H | CH$_3$ | Phe | — | —(CH$_2$)$_4$— |
| 49 | — | H | CH$_3$ | Phe | O | —CH$_2$— |
| 50 | — | H | CH$_3$ | Phe | O | —(CH$_2$)$_2$— |
| 51 | — | H | CH$_3$ | Phe | O | —(CH$_2$)$_3$— |
| 52 | — | H | CH$_3$ | Phe | O | —(CH$_2$)$_4$— |
| 53 | — | F | H | — | — | —CH$_2$— |
| 54 | — | F | H | — | — | —(CH$_2$)$_2$— |
| 55 | — | F | H | — | — | —(CH$_2$)$_3$— |
| 56 | — | F | H | — | — | —(CH$_2$)$_4$— |
| 57 | — | F | H | — | O | —CH$_2$— |
| 58 | — | F | H | — | O | —(CH$_2$)$_2$— |
| 59 | — | F | H | — | O | —(CH$_2$)$_3$— |
| 60 | — | F | H | — | O | —(CH$_2$)$_4$— |
| 61 | Phe | F | H | — | — | —CH$_2$— |
| 62 | Phe | F | H | — | — | —(CH$_2$)$_2$— |
| 63 | Phe | F | H | — | — | —(CH$_2$)$_3$— |
| 64 | Phe | F | H | — | — | —(CH$_2$)$_4$— |
| 65 | Phe | F | H | — | O | —CH$_2$— |
| 66 | Phe | F | H | — | O | —(CH$_2$)$_2$— |
| 67 | Phe | F | H | — | O | —(CH$_2$)$_3$— |
| 68 | Phe | F | H | — | O | —(CH$_2$)$_4$— |
| 69 | — | F | H | Phe | — | —CH$_2$— |
| 70 | — | F | H | Phe | — | —(CH$_2$)$_2$— |
| 71 | — | F | H | Phe | — | —(CH$_2$)$_3$— |
| 72 | — | F | H | Phe | — | —(CH$_2$)$_4$— |
| 73 | — | F | H | Phe | O | —CH$_2$— |
| 74 | — | F | H | Phe | O | —(CH$_2$)$_2$— |
| 75 | — | F | H | Phe | O | —(CH$_2$)$_3$— |
| 76 | — | F | H | Phe | O | —(CH$_2$)$_4$— |
| 77 | — | F | CH$_3$ | — | — | —CH$_2$— |

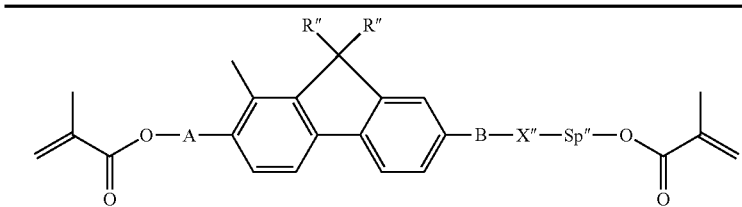

| No. | A | L' | R" | B | X" | Sp" |
|---|---|---|---|---|---|---|
| 78 | — | F | CH$_3$ | — | — | —(CH$_2$)$_2$— |
| 79 | — | F | CH$_3$ | — | — | —(CH$_2$)$_3$— |
| 80 | — | F | CH$_3$ | — | — | —(CH$_2$)$_4$— |
| 81 | — | F | CH$_3$ | — | O | —CH$_2$— |
| 82 | — | F | CH$_3$ | — | O | —(CH$_2$)$_2$— |
| 83 | — | F | CH$_3$ | — | O | —(CH$_2$)$_3$— |
| 84 | — | F | CH$_3$ | — | O | —(CH$_2$)$_4$— |
| 85 | Phe | F | CH$_3$ | — | — | —CH$_2$— |
| 86 | Phe | F | CH$_3$ | — | — | —(CH$_2$)$_2$— |
| 87 | Phe | F | CH$_3$ | — | — | —(CH$_2$)$_3$— |
| 88 | Phe | F | CH$_3$ | — | — | —(CH$_2$)$_4$— |
| 89 | Phe | F | CH$_3$ | — | O | —CH$_2$— |
| 90 | Phe | F | CH$_3$ | — | O | —(CH$_2$)$_2$— |
| 91 | Phe | F | CH$_3$ | — | O | —(CH$_2$)$_3$— |
| 92 | Phe | F | CH$_3$ | — | O | —(CH$_2$)$_4$— |
| 93 | — | F | CH$_3$ | Phe | — | —CH$_2$— |
| 94 | — | F | CH$_3$ | Phe | — | —(CH$_2$)$_2$— |
| 95 | — | F | CH$_3$ | Phe | — | —(CH$_2$)$_3$— |
| 96 | — | F | CH$_3$ | Phe | — | —(CH$_2$)$_4$— |
| 97 | — | F | CH$_3$ | Phe | O | —CH$_2$— |
| 98 | — | F | CH$_3$ | Phe | O | —(CH$_2$)$_2$— |
| 99 | — | F | CH$_3$ | Phe | O | —(CH$_2$)$_3$— |
| 100 | — | F | CH$_3$ | Phe | O | —(CH$_2$)$_4$— |

Compounds of the following formula (Nos. 101-148):

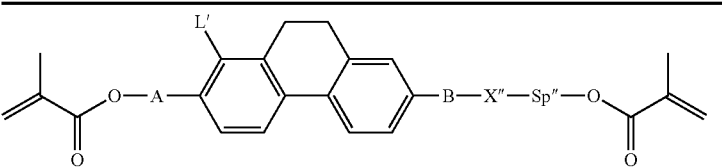

| No. | A | L' | B | X" | Sp" |
|---|---|---|---|---|---|
| 101 | — | H | — | — | —CH$_2$— |
| 102 | — | H | — | — | —(CH$_2$)$_2$— |
| 103 | — | H | — | — | —(CH$_2$)$_3$— |
| 104 | — | H | — | — | —(CH$_2$)$_4$— |
| 105 | — | H | — | O | —CH$_2$— |
| 106 | — | H | — | O | —(CH$_2$)$_2$— |
| 107 | — | H | — | O | —(CH$_2$)$_3$— |
| 108 | — | H | — | O | —(CH$_2$)$_4$— |
| 109 | Phe | H | — | — | —CH$_2$— |
| 110 | Phe | H | — | — | —(CH$_2$)$_2$— |
| 111 | Phe | H | — | — | —(CH$_2$)$_3$— |
| 112 | Phe | H | — | — | —(CH$_2$)$_4$— |
| 113 | Phe | H | — | O | —CH$_2$— |
| 114 | Phe | H | — | O | —(CH$_2$)$_2$— |
| 115 | Phe | H | — | O | —(CH$_2$)$_3$— |
| 116 | Phe | H | — | O | —(CH$_2$)$_4$— |
| 117 | — | H | Phe | — | —CH$_2$— |
| 118 | — | H | Phe | — | —(CH$_2$)$_2$— |
| 119 | — | H | Phe | — | —(CH$_2$)$_3$— |
| 120 | — | H | Phe | — | —(CH$_2$)$_4$— |
| 121 | — | H | Phe | O | —CH$_2$— |
| 122 | — | H | Phe | O | —(CH$_2$)$_2$— |
| 123 | — | H | Phe | O | —(CH$_2$)$_3$— |
| 124 | — | H | Phe | O | —(CH$_2$)$_4$— |
| 125 | — | F | — | — | —CH$_2$— |
| 126 | — | F | — | — | —(CH$_2$)$_2$— |
| 127 | — | F | — | — | —(CH$_2$)$_3$— |
| 128 | — | F | — | — | —(CH$_2$)$_4$— |

-continued

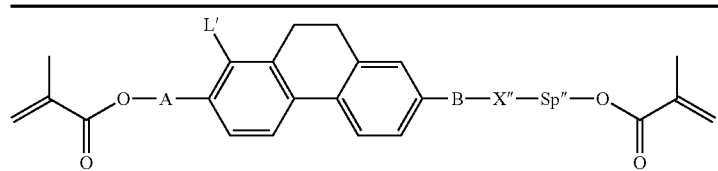

| No. | A | L' | B | X" | Sp" |
|---|---|---|---|---|---|
| 129 | — | F | — | O | —CH₂— |
| 130 | — | F | — | O | —(CH₂)₂— |
| 131 | — | F | — | O | —(CH₂)₃— |
| 132 | — | F | — | O | —(CH₂)₄— |
| 133 | Phe | F | — | — | —CH₂— |
| 134 | Phe | F | — | — | —(CH₂)₂— |
| 135 | Phe | F | — | — | —(CH₂)₃— |
| 136 | Phe | F | — | — | —(CH₂)₄— |
| 137 | Phe | F | — | O | —CH₂— |
| 138 | Phe | F | — | O | —(CH₂)₂— |
| 139 | Phe | F | — | O | —(CH₂)₃— |
| 140 | Phe | F | — | O | —(CH₂)₄— |
| 141 | — | F | Phe | — | —CH₂— |
| 142 | — | F | Phe | — | —(CH₂)₂— |
| 143 | — | F | Phe | — | —(CH₂)₃— |
| 144 | — | F | Phe | — | —(CH₂)₄— |
| 145 | — | F | Phe | O | —CH₂— |
| 146 | — | F | Phe | O | —(CH₂)₂— |
| 147 | — | F | Phe | O | —(CH₂)₃— |
| 148 | — | F | Phe | O | —(CH₂)₄— |

Compounds of the following formula (Nos. 149-196):

| No. | A | L' | B | X" | Sp" |
|---|---|---|---|---|---|
| 149 | — | H | — | — | —CH₂— |
| 150 | — | H | — | — | —(CH₂)₂— |
| 151 | — | H | — | — | —(CH₂)₃— |
| 152 | — | H | — | — | —(CH₂)₄— |
| 153 | — | H | — | O | —CH₂— |
| 154 | — | H | — | O | —(CH₂)₂— |
| 155 | — | H | — | O | —(CH₂)₃— |
| 156 | — | H | — | O | —(CH₂)₄— |
| 157 | Phe | H | — | — | —CH₂— |
| 158 | Phe | H | — | — | —(CH₂)₂— |
| 159 | Phe | H | — | — | —(CH₂)₃— |
| 160 | Phe | H | — | — | —(CH₂)₄— |
| 161 | Phe | H | — | O | —CH₂— |
| 162 | Phe | H | — | O | —(CH₂)₂— |
| 163 | Phe | H | — | O | —(CH₂)₃— |
| 164 | Phe | H | — | O | —(CH₂)₄— |
| 165 | — | H | Phe | — | —CH₂— |
| 166 | — | H | Phe | — | —(CH₂)₂— |
| 167 | — | H | Phe | — | —(CH₂)₃— |
| 168 | — | H | Phe | — | —(CH₂)₄— |
| 169 | — | H | Phe | O | —CH₂— |
| 170 | — | H | Phe | O | —(CH₂)₂— |
| 171 | — | H | Phe | O | —(CH₂)₃— |
| 172 | — | H | Phe | O | —(CH₂)₄— |
| 173 | — | F | — | — | —CH₂— |
| 174 | — | F | — | — | —(CH₂)₂— |
| 175 | — | F | — | — | —(CH₂)₃— |
| 176 | — | F | — | — | —(CH₂)₄— |
| 177 | — | F | — | O | —CH₂— |
| 178 | — | F | — | O | —(CH₂)₂— |
| 179 | — | F | — | O | —(CH₂)₃— |
| 180 | — | F | — | O | —(CH₂)₄— |
| 181 | Phe | F | — | — | —CH₂— |

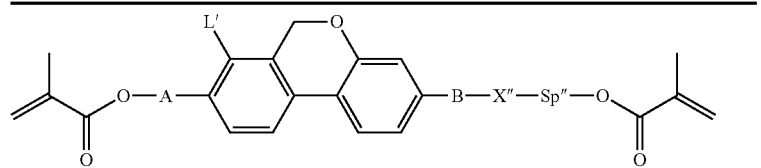

| No. | A | L' | B | X" | Sp" |
|---|---|---|---|---|---|
| 182 | Phe | F | — | — | —(CH$_2$)$_2$— |
| 183 | Phe | F | — | — | —(CH$_2$)$_3$— |
| 184 | Phe | F | — | — | —(CH$_2$)$_4$— |
| 185 | Phe | F | — | O | —CH$_2$— |
| 186 | Phe | F | — | O | —(CH$_2$)$_2$— |
| 187 | Phe | F | — | O | —(CH$_2$)$_3$— |
| 188 | Phe | F | — | O | —(CH$_2$)$_4$— |
| 189 | — | F | Phe | — | —CH$_2$— |
| 190 | — | F | Phe | — | —(CH$_2$)$_2$— |
| 191 | — | F | Phe | — | —(CH$_2$)$_3$— |
| 192 | — | F | Phe | — | —(CH$_2$)$_4$— |
| 193 | — | F | Phe | O | —CH$_2$— |
| 194 | — | F | Phe | O | —(CH$_2$)$_2$— |
| 195 | — | F | Phe | O | —(CH$_2$)$_3$— |
| 196 | — | F | Phe | O | —(CH$_2$)$_4$— |

Example 197

9,9-Dimethyl-7-[4-(2-methylacryloyloxy)butyl]-9H-fluoren-2-yl 2-methylacrylate

197.1 4-[9,9-Dimethyl-7-(2-methylacryloyloxy)-9H-fluoren-2-yl]but-3-ynyl 2-methylacrylate

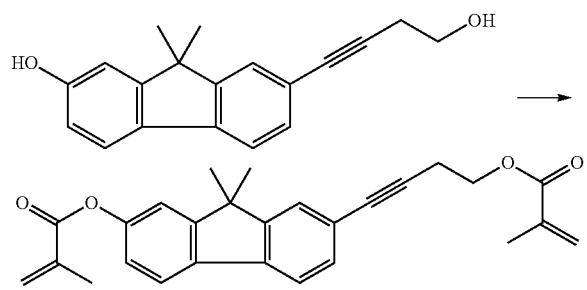

An analogous procedure to Example 1 starting from 7-(4-hydroxybut-1-ynyl)-9,9-dimethyl-9H-fluoren-2-ol (preparation see Example 32.2) gives 4-[9,9-dimethyl-7-(2-methylacryloyloxy)-9H-fluoren-2-yl]but-3-ynyl 2-methyl-acrylate as colourless oil. Glass transition Tg-17 I.

Use Example A

Nematic LC mixture N1 is formulated as follows:

| CCH-501 | 9.00% | cl.p. | +70.0 |
|---|---|---|---|
| CCH-35 | 14.00% | Δn | 0.0825 |
| PCH-53 | 8.00% | Δε | −3.5 |
| CY-3-O4 | 14.00% | ε$_\parallel$ | 3.5 |
| CY-5-O4 | 13.00% | K$_3$/K$_1$ | 1.00 |
| CCY-3-O2 | 8.00% | γ | 141 |
| CCY-5-O2 | 8.00% | V$_0$ | 2.06 |
| CCY-2-1 | 9.00% | | |
| CCY-3-1 | 9.00% | | |
| CPY-2-O2 | 8.00% | | |

0.3% of a polymerisable monomeric compound of one of the formulae shown below is added to LC mixture N1, and the resultant mixture is introduced into VA e/o test cells (rubbed antiparallel, VA-polyimide alignment layer, layer thickness d≈4 μm). The cells are irradiated with UV light having an intensity of 50 mW/cm$^2$ for the time indicated with application of a voltage of 24 V (alternating current), causing polymerisation of the monomeric compound. The tilt angle is determined before and after the UV irradiation by rotational crystal experiment (Autronic-Melchers TBA-105).

In order to determine the polymerisation rate, the residual content of unpolymerised RM (in % by weight) in the test cells after various exposure times is measured using the HPLC method. To this end, each mixture is polymerised in the test cell under the conditions indicated. The mixture is then rinsed out of the test cell using methyl ethyl ketone and measured.

For comparative purposes, the experiments described above are carried out with the structurally analogous polymerisable compound M1 known from the prior art (for example U.S. Pat. No. 7,169,449).

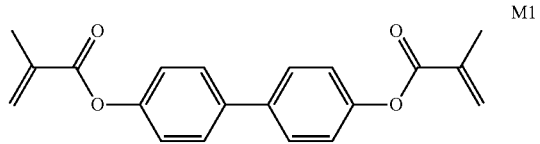

M1

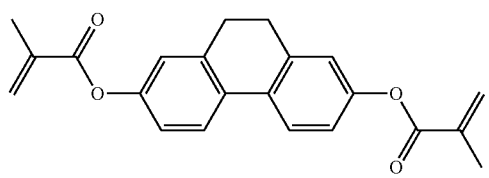

Example 1

-continued

Example 2

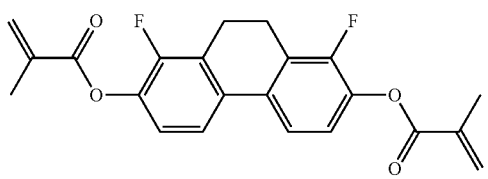

Example 4

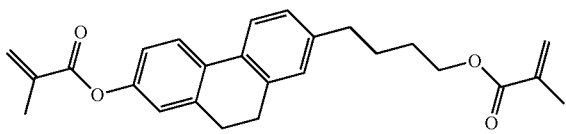

The tilt angle results are shown in Table 1.

TABLE 1

| Exposure time/s | M1 | Ex. 1 | Ex. 2 | Ex. 4 |
|---|---|---|---|---|
| | | Tilt angle/° | | |
| 0 | 89.2 | 89.5 | 88.9 | 89.6 |
| 30 | 89.1 | 88.7 | 88.5 | 89.8 |
| 60 | 88.4 | 83.0 | 86.0 | 88.3 |
| 120 | 83.9 | 77.3 | 81.6 | 83.3 |
| 240 | 76.5 | 74.8 | 76.1 | 73.5 |
| 360 | — | 75.1 | — | 66.1 |

As can be seen from Table 1, a small tilt angle after polymerisation can be achieved more rapidly in PSA displays with the monomers according to the invention from Examples 1-4 than in PSA displays with monomer M1 from the prior art.

The RM concentrations after various exposure times are shown in Table 2.

TABLE 2

| Exposure time/s | M1 | Ex. 1 | Ex. 2 | Ex. 4 |
|---|---|---|---|---|
| | | RM concentration (% by weight) | | |
| 0 | 0.300 | 0.300 | 0.300 | 0.300 |
| 120 | 0.268 | 0.131 | 0.197 | 0.195 |
| 240 | 0.226 | 0.054 | 0.111 | 0.103 |
| 360 | 0.176 | 0.010 | 0.062 | 0.069 |

As can be seen from Table 2, a significantly faster polymerisation rate is achieved in PSA displays with the monomers according to the invention from Examples 1-4 than in PSA displays with monomer M1 from the prior art.

Use Example B

Test cells are produced as described in Example A using LC mixture N1 and a polymerisable monomeric compound from Example 32 or Example 197, and the tilt angle after various exposure times and the residual content of unpolymerised RM are measured.

Example 32

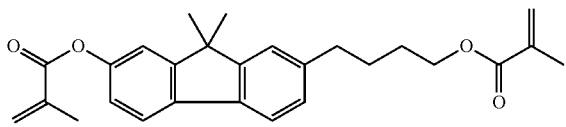

Example 197

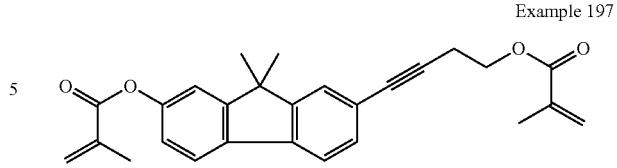

The results are shown in Tables 3 and 4.

TABLE 3

| Exposure time/s | Ex. 32 | Ex. 197 |
|---|---|---|
| | Tilt angle/° | |
| 0 | 89.7 | 89.2 |
| 30 | 89.1 | 88.7 |
| 60 | 88.6 | 83.2 |
| 120 | 73.8 | 60.5 |
| 240 | 37.6 | 44.6 |
| 360 | 28.8 | 39.2 |

As can be seen from Table 3, a very small tilt angle can be achieved rapidly after polymerisation in PSA displays with the monomers according to the invention.

TABLE 4

| Exposure time/s | Ex. 32 | Ex. 197 |
|---|---|---|
| | RM concentration (% by weight) | |
| 0 | 0.300 | 0.300 |
| 120 | 0.110 | 0.013 |
| 240 | 0.000 | 0.000 |
| 360 | 0.000 | 0.000 |

As can be seen from Table 4, very rapid and complete polymerisation is achieved in PSA displays with the monomers according to the invention.

The invention claimed is:

1. A liquid crystal display which is a PS (polymer stabilized) or PSA (polymer sustained alignment) liquid crystal display which comprises a compound of the formula I:

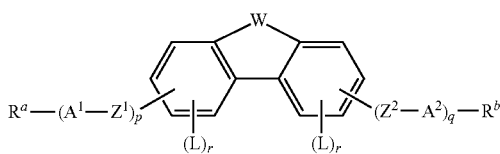

I in which the individual radicals have the following meanings:

W denotes —C($R^c R^d$)—, —CH$_2$CH$_2$—, —CH$_2$—O—, —O—, —CO—, —CO—O—, —S— or —N($R^c$)—, $R^c$, $R^d$ each, independently of one another, denote P-Sp-, H, F, Cl, Br, I, —CN, —NO$_2$, —NCO, —NCS, —OCN, —SCN, SF$_5$, straight-chain or branched alkyl having 1 to 25 C atoms, in which, in addition, one or more non-adjacent CH$_2$ groups may each be replaced, independently of one another, by arylene, —C($R^0$)=C($R^{00}$)—, —C≡C—, —N($R^0$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, or aryl or heteroaryl, preferably having 2 to 25 C atoms, which may also contain two or more fused rings and which is optionally mono- or polysubstituted by L, $R^a$, $R^b$ each, independently of one another, have one of the meanings indicated for $R^c$, where at least one of the radicals $R^a$ and $R^b$ denotes or contains a group P-Sp-, P on each occurrence, identically or differently, denotes a polymerisable group, Sp on each occurrence, identically or differently, denotes a spacer group or a single bond, $A^1$, $A^2$ each, independently of one another, denote an aromatic, heteroaromatic, alicyclic or heterocyclic group, preferably having 4 to 25 C atoms, which may also contain fused rings and which is optionally mono- or polysubstituted by L, L on each occurrence, identically or differently, denotes P-Sp-, H, OH, $CH_2OH$, halogen, $SF_5$, $NO_2$, a carbon group or hydrocarbon group, $Z^1$, $Z^2$ each, independently of one another, denote —O—, —S—, —CO—, —CO—O—, —O—CO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CH_2)_n$—, $CF_2CH_2$—, —$CH_2CF_2$—, —$(CF_2)_n$—, —CH=CH—, —CF=CF—, —CH=CF—, —CF=CH—, —C≡C—, —CH=CH—COO—, —O—CO—CH=CH—, —$CH_2$—$CH_2$—CO—O—, —O—CO—$CH_2$—$CH_2$—, —$C(R^0R^{00})$—, —$C(R^yR^z)$— or a single bond, $R^0$, $R^{00}$ each, independently of one another and identically or differently on each occurrence, denote H or alkyl having 1 to 12 C atoms, $R^y$, $R^z$ each, independently of one another, denote H, F, $CH_3$ or $CF_3$, n on each occurrence, identically or differently, denotes 1, 2, 3 or 4, p, q each, independently of one another, denote 0, 1, 2 or 3, r on each occurrence, identically or differently, denotes 0, 1, 2 or 3.

2. A liquid crystal display according to claim 1, characterised in that $R^a$ and $R^b$ in formula I denote identical or different radicals P-Sp-.

3. A or liquid crystal display according to claim 1, characterised in that the compounds of the formula I are selected from the group consisting of the following sub-formulae:

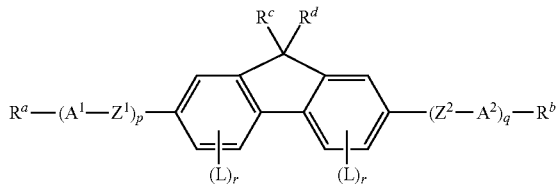

I1

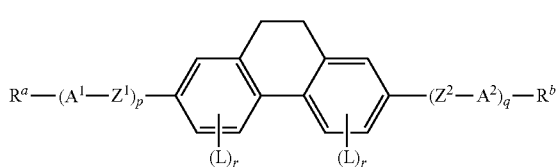

I2

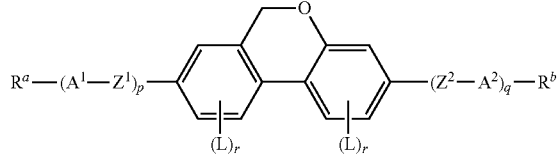

I3 the individual radicals have the meanings indicated in claim 1.

4. A liquid crystal display according to claim 1, characterised in that the compounds of the formula I are selected from the group consisting of the following sub-formulae:

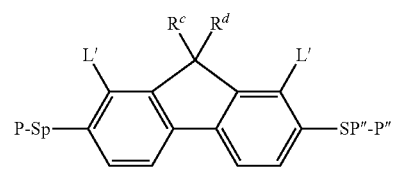

I1a

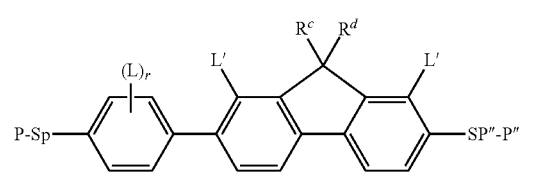

I1b

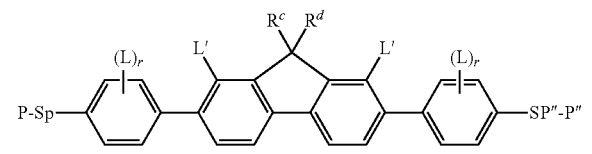

I1c

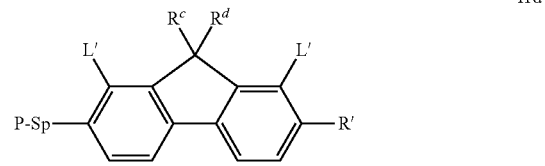

I1d

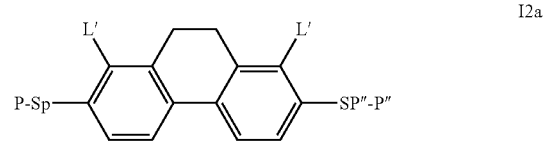

I2a

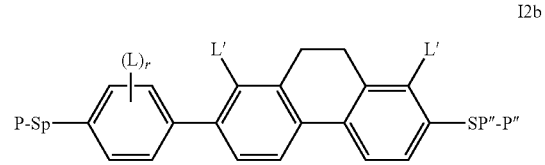

I2b

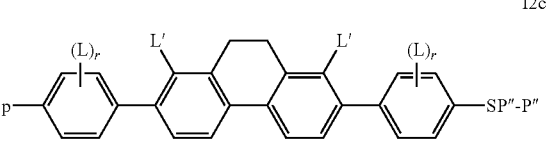

I2c

-continued

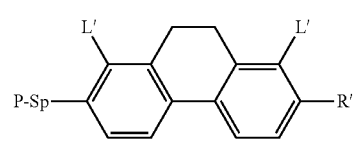

I2d

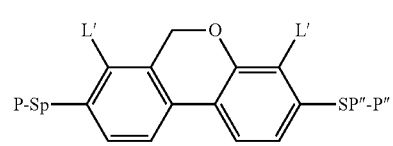

I3a

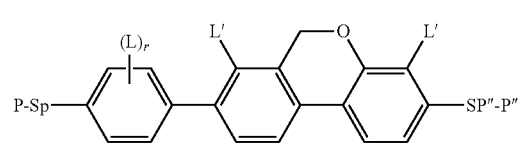

I3b

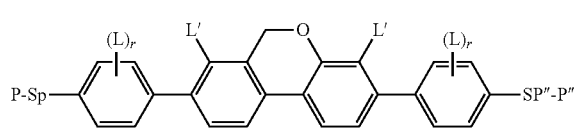

I3c

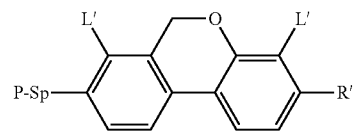

I3d in which L' denotes H or F, P and Sp have one of the meanings indicated in claim 1, P" has one of the meanings indicated for P in claim 1, Sp" has one of the meanings indicated for Sp in claim 1, and R' has one of the meanings indicated for $R^a$ in claim 1, where R' is other than H and does not denote or contain a group P-Sp-.

5. A liquid crystal display according to claim 1 which is a PS or PSA liquid crystal display containing an LC cell having two substrates, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium with application of an electrical voltage to the electrodes, where at least one of the polymerisable compounds is selected from formula I according to claim 1.

6. A display according to claim 1, characterised in that the display comprises one or more compounds of the formulae CY and/or PY:

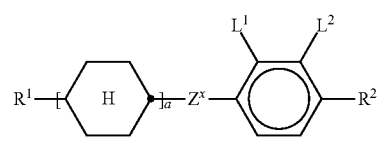

CY

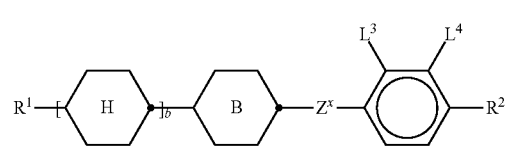

PY in which the individual radicals have the following meanings:
a denotes 1 or 2,
b denotes 0 or 1,

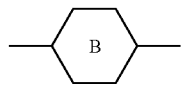

denotes

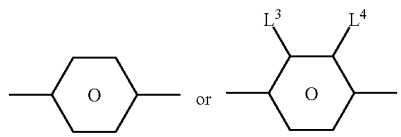

$R^1$ and $R^2$ each, independently of one another, denote alkyl having 1 to 12 C atoms, where, in addition, one or two non-adjacent $CH_2$ groups may be replaced by —O—, —CH=CH—, —CO—, —O—CO— or —CO—O— in such a way that O atoms are not linked directly to one another, $Z^x$ denotes —CH=CH—, —$CH_2$O—, —O$CH_2$—, —$CF_2$O—, —O$CF_2$—, —O—, —$CH_2$—, —$CH_2CH_2$— or a single bond, preferably a single bond, $L^{1-4}$ each, independently of one another, denote F, Cl, $OCF_3$, $CF_3$, $CH_3$, $CH_2F$, $CHF_2$.

7. A liquid crystal display according to claim 1, characterised in that the display comprises one or more compounds of the following formula:

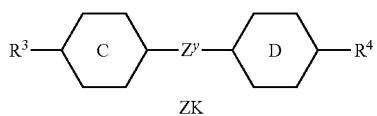

ZK in which the individual radicals have the following meanings:

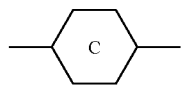

denotes

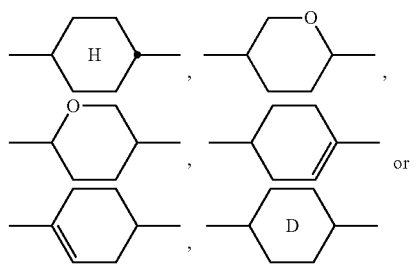

denotes

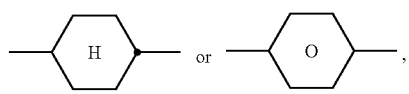

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —$CH_2CH_2$—, —CH=CH—, —$CF_2O$—, —$OCF_2$—, —$CH_2O$—, —$OCH_2$—, —COO—, —OCO—, —$C_2F_4$—, —CF=CF— or a single bond.

8. A liquid crystal display according to claim 1 characterised in that it is a PSA-VA, PSA-OCB, PS-IPS, PS-FFS or PS-TN display.

9. Compounds of the formula I1

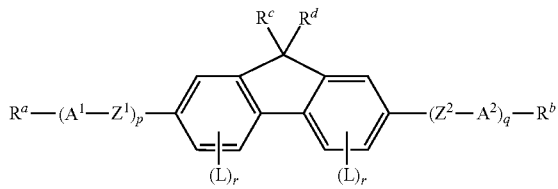

I1 in which $R^{c,d}$, $A^{1,2}$, $Z^{1,2}$, L, p, q and r have the meanings indicated in claim 1, and $R^a$ and $R^b$ denote P-Sp-, where Sp in one of the radicals $R^a$ and $R^b$ denotes a single bond and Sp in the other of the radicals $R^a$ and $R^b$ denotes a group of the formula Sp'-X', so that this radical P-Sp- conforms to the formula P-Sp'-X'-, Sp' denotes alkylene having 1 to 20 C atoms, which is optionally mono- or polysubstituted by F, Cl, Br, I or CN and in which, in addition, one or more non-adjacent $CH_2$ groups may each be replaced, independently of one another, by —O—, —S—, —NH—, —$N(R^0)$—, —Si$(R^{00}R^{000})$—, —CO—, —CO—O—, —O—CO—, —O—CO—O—, —S—CO—, —CO—S—, —$N(R^{00})$—CO—O—, —O—CO—$N(R^{00})$—, —$N(R^{00})$—CO—$N(R^{00})$—, —CH=CH— or —C≡C— in such a way that O and/or S atoms are not linked directly to one another, X' denotes —O—, —S—, —CO—, —CO—O—, —O—CO—, —O—CO—O—, —CO—$N(R^{00})$—, —$N(R^{00})$—CO—, —$N(R^{00})$—CO—$N(R^{00})$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^2$=$CY^3$—, —C≡C—, —CH=CH—CO—O—, —O—CO—CH=CH— or a single bond, $R^{00}R^{000}$ each, independently of one another, denote H or alkyl having 1 to 12 C atoms, $Y^2$, $Y^3$ each, independently of one another, denote H, F, Cl or CN, P is on each occurrence, identically or differently, selected from $CH_2$=$CW^1$—CO—O—, $CH_2$=$CW^1$—CO—,

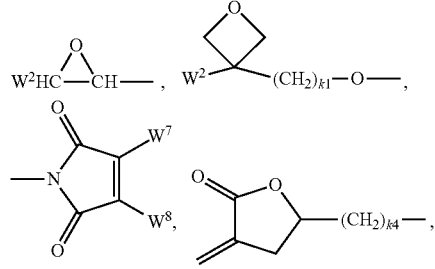

$CH_2$=$CW^2$—O—, $CW^1$=CH—CO—(O)$_{k3}$—, $CW^1$=CH—CO—NH—, $CH_2$=$CW^1$—CO—NH—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, $CH_2$=$CW^1$—CO—NH—, $CH_2$=CH—(COO)$_{k1}$—Phe—(O)$_{k2}$—, $CH_2$=CH—(CO)$_{k1}$-Phe-(O)$_{k2}$— and $W^4W^5W^6Si$—, in which $W^1$ denotes H, F, Cl, CN, $CF_3$, phenyl or alkyl having 1 to 5 C atoms, $W^2$ and $W^3$ each, independently of one another, denote H or alkyl having 1 to 5 C atoms, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, and $k_4$ denotes an integer from 1 to 10.

10. A liquid crystal medium according to claim 9, in which component B) comprises one or more compounds selected from the formulae CY, PY and ZK

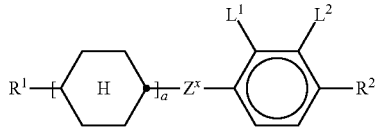

CY

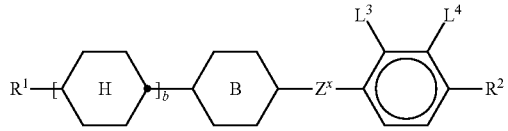

PY

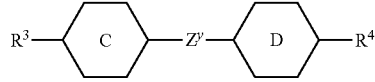

ZK in which the individual radicals have the following meanings:
a denotes 1 or 2,
b denotes 0 or 1,

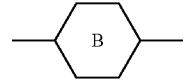

denotes

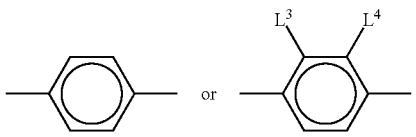

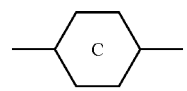

denotes

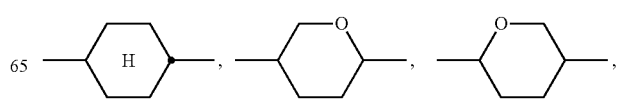

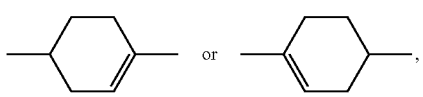

or

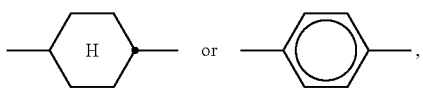

denotes

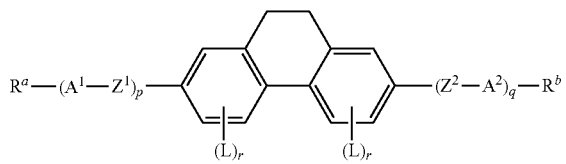

R$^1$ R$^4$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another, Z$^x$ and Z$^y$ denote —CH=CH—, —CH$_2$O—, —OCH$_2$—, —CF$_2$O—, —OCF$_2$—, —O—, —CH$_2$—, —CH$_2$CH$_2$— or a single bond, L$^{1-4}$ each, independently of one another, denote F, Cl, OCF$_3$, CF$_3$, CH$_3$, CH$_2$F or CHF$_2$.

11. A liquid crystal medium comprising
a polymerisable component A) comprising one or more polymerisable compounds, and
a liquid-crystalline component B) comprising one or more low-molecular-weight compounds,
characterised in that component A) comprises one or more polymerisable compounds of the formula I1 according to claim 9 or compounds of the formulae I2 and I3:

I2

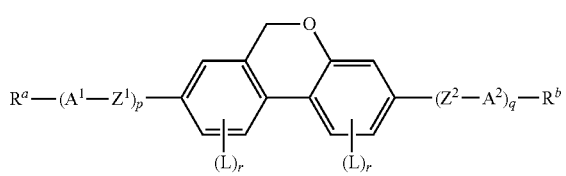

I3

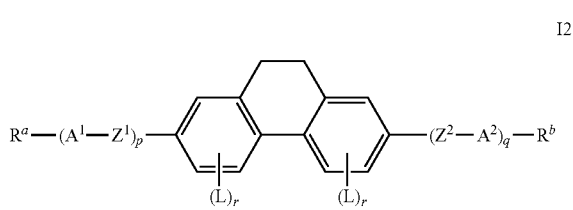

R$^a$, R$^b$ each, independently of one another, denote P-Sp-, H, F, Cl, Br, I, —CN, —NO$_2$, —NCO, —NCS, —OCN, —SCN, SF$_5$, straight-chain or branched alkyl having 1 to 25 C atoms, in which, in addition, one or more non-adjacent CH$_2$ groups may each be replaced, independently of one another, by arylene, —C(R$^0$)=C(R$^{00}$)—, —C≡C—, —N(R$^0$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, or aryl or heteroaryl, preferably having 2 to 25 C atoms, which may also contain two or more fused rings and which is optionally mono- or polysubstituted by L, where at least one of the radicals R$^a$ and R$^b$ denotes or contains a group P-Sp-, P on each occurrence, identically or differently, denotes a polymerisable group, Sp on each occurrence, identically or differently, denotes a spacer group or a single bond, A$^1$, A$^2$ each, independently of one another, denote an aromatic, hetero-aromatic, alicyclic or heterocyclic group, preferably having 4 to 25 C atoms, which may also contain fused rings and which is optionally mono- or polysubstituted by L, L on each occurrence, identically or differently, denotes P-Sp-, H, OH, CH$_2$OH, halogen, SF$_S$, NO$_2$, a carbon group or hydrocarbon group, Z$^1$, Z$^2$ each, independently of one another, denote —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_n$—, —CF$_2$CH$_2$—, —CH$_2$CF$_2$—, —(CF$_2$)$_n$—, —CH=CH—, —CF=CF—, —CH=CF—, —CF=CH—, —C≡C—, —CH=CH—COO—, —O—CO—CH=CH—, —CH$_2$—CH$_2$—CO—O—, —O—CO—CH$_2$—CH$_2$—, —C(R$^0$R$^{00}$)—, —C(R$^y$R$^z$)— or a single bond, R$^0$, R$^{00}$ each, independently of one another and identically or differently on each occurrence, denote H or alkyl having 1 to 12 C atoms, R$^y$, R$^z$ each, independently of one another, denote H, F, CH$_3$ or CF$_3$, n on each occurrence, identically or differently, denotes 1, 2, 3 or 4, p, q each, independently of one another, denote 0, 1, 2 or 3, r on each occurrence, identically or differently, denotes 0, 1, 2 or 3.

12. Compounds of the formulae I2 and I3:

I2

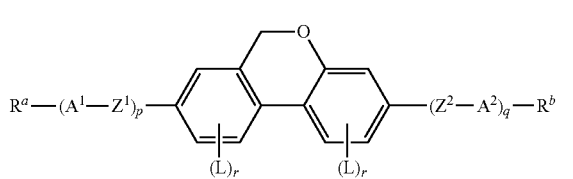

I3

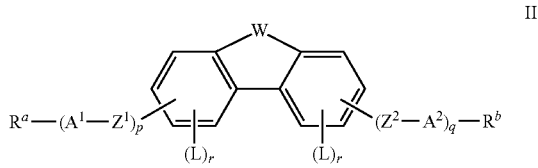

in which the individual radicals have the meanings indicated in claim 1.

13. Compounds of the formula II

II

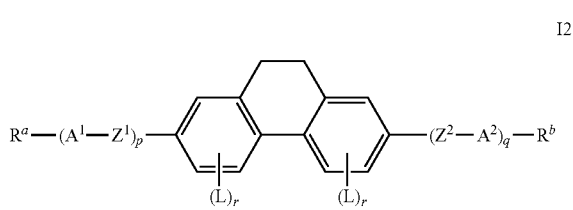

in which the individual radicals have the meanings indicated in claim 1, with the proviso that both radicals R$^a$ and R$^b$ denote -Sp-O-Sg, where Sg denotes an H atom or a protecting group.

14. Compounds according to claim 13, selected from the group consisting of the following sub-formulae:

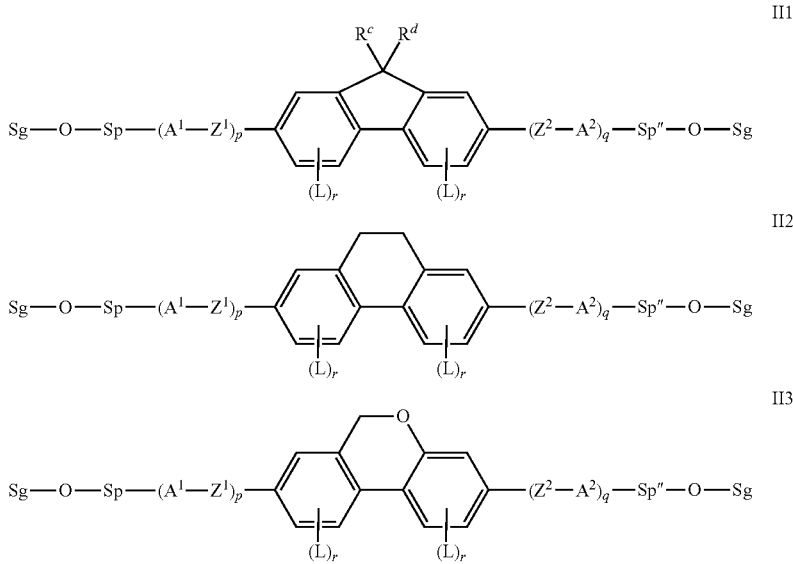

in which $R^{c,d}$, $A^{1,2}$, $Z^{1,2}$, L, p, q, r, Sp, Sp" and Sg have the meanings indicated in claim 13, where, in formula II1, Sp denotes a single bond and Sp" is other than a single bond.

15. Compounds of the formula III

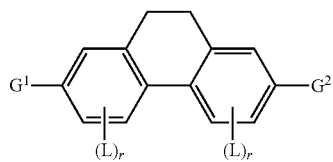

in which L and r have the meanings indicated in claim 1, and $G^1$ and $G^2$ denote identical or different radicals selected from Cl, Br, I and OH.

16. Process for the preparation of a compound according to claim 9, in which a compound of formula II,

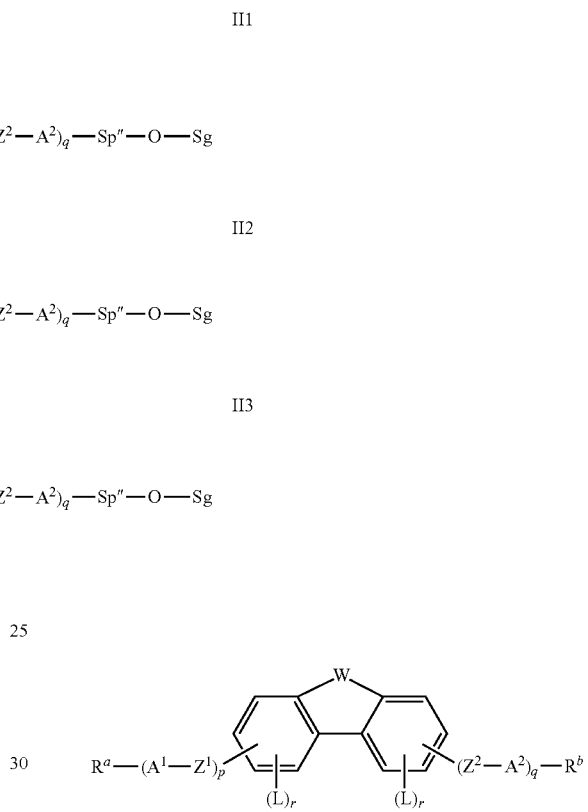

is esterified or etherified using corresponding acids, acid derivatives or halogenated compounds containing a group P, in the presence of a dehydrating reagent.

17. A process for the production of a PS or PSA liquid crystal display in which an LC medium according to claim 11 is introduced into an LC cell having two substrates, where at least one substrate is transparent to light and at least one substrate has one or two electrodes, and the polymerisable compounds are polymerised with application of an electrical voltage to the electrodes.

* * * * *